(12) United States Patent
Haynes et al.

(10) Patent No.: US 8,722,661 B2
(45) Date of Patent: May 13, 2014

(54) PYRROLOPYRIMIDONE AND PYRROLOPYRIDONE INHIBITORS OF TANKYRASE

(71) Applicant: Genentech, Inc., South San Francisco, CA (US)

(72) Inventors: Nancy-Ellen Haynes, Cranford, NJ (US); Johannes Hermann, Jersey City, NJ (US); Kyungjin Kim, Livingston, NJ (US); Nathan Robert Scott, Livingston, NJ (US); Lin Yi, Basking Ridge, NJ (US); Mark Zak, San Mateo, CA (US)

(73) Assignees: Hoffmann-La Roche Inc., Nutley, NJ (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/911,601

(22) Filed: Jun. 6, 2013

(65) Prior Publication Data

US 2013/0331375 A1    Dec. 12, 2013

Related U.S. Application Data

(60) Provisional application No. 61/656,650, filed on Jun. 7, 2012.

(51) Int. Cl.
*A61K 31/00* (2006.01)
*C07D 401/00* (2006.01)
*C07D 487/00* (2006.01)
*C07D 471/02* (2006.01)

(52) U.S. Cl.
USPC ....... 514/210.21; 544/362; 544/280; 546/116

(58) Field of Classification Search
USPC ............... 514/210.21; 544/280, 362; 546/113
See application file for complete search history.

(56) References Cited

U.S. PATENT DOCUMENTS 6,878,716 B1    4/2005    Castelhano et al.
2009/0181941 A1    7/2009    Leblanc et al.

FOREIGN PATENT DOCUMENTS

WO    WO 0139777 A1 *    6/2001
WO    2006/003148 A1    1/2006
WO    2009/153261 A1    12/2009

OTHER PUBLICATIONS

West et al. "Journal of Organic Chemistry (1961), 26, 3809-12".*
Database Caplus [online] Chemical Abstracts Service, Columbus, Ohio, US; XP002701050, Database Accession No. 2011:950648.
Huang et al., "Tankyrase inhibition stabilizes axin and antagonizes Wnt signalling" Nature 461 (7264):614-620 (Sep. 16, 2009).

* cited by examiner

*Primary Examiner* — Jeffrey H Murray
*Assistant Examiner* — Oluwafemi Masha
(74) *Attorney, Agent, or Firm* — Brian L. Buckwalter

(57) ABSTRACT

There are provided compounds of the formula (I)

(I)

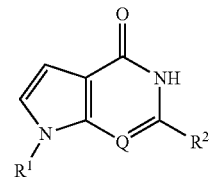

wherein Q, $R_1$ and $R_2$ are defined herein. The compounds have activity as anticancer agents.

11 Claims, No Drawings

PYRROLOPYRIMIDONE AND PYRROLOPYRIDONE INHIBITORS OF TANKYRASE

CROSS REFERENCE TO PRIOR APPLICATIONS

This application claims the benefit of priority to U.S. 61/656,650 filed Jun. 7, 2012 the contents of which is hereby incorporated by reference in its entirety.

FIELD OF THE INVENTION

The present invention relates to pyrrolopyrimidones and pyrrolopyridones which act as inhibitors of tankyrase and are useful in the amelioration or treatment of cancer.

BACKGROUND OF THE INVENTION

Cancer is a disease characterized by the loss of appropriate control for cell growth. The American Cancer Society has estimated that there were in excess of 1.5 million new cases of cancer within the United Stated of America in 2010 and approximately 570,000 deaths that year estimated to be attributable to cancer. The World Health Organization has estimated that cancer was the leading cause of death globally in 2010, with the number of deaths caused by cancer growing to 12 million per year by 2030.

It has been suggested that there are 6 capabilities which need to be developed by cells in order to lead to the formation of cancerous lesions. These traits are self-sufficiency in growth signals, insensitivity to anti-growth signals, tissue invasion and metastasis, limitless replication potential, sustained angiogenesis and evasion of apoptosis. Growth signaling is required for cells to transition from a quiescent state into an active proliferative state. These signals are typically transmitted from transmembrane receptors, through signal transduction cascades involving numerous intracellular kinases, eventually resulting in changes in gene expression at the nuclear level within the cell. In recent years there has been much interest in the area of signal transduction inhibitors, particularly kinase inhibitors, and their use for the treatment of cancer. Several examples from this class of compounds have been successfully evaluated in clinical settings and are now commercially available and marketed for the treatment of specific forms of cancer e.g. imatinib tosylate (marketed as Gleevec® by Novartis for the treatment of Philadelphia chromosome-positive chronic myeloid leukemia), lapatinib ditosylate (marketed as Tykerb® by GlaxoSmithKline for the treatment of HER2 positive breast cancer in combination with other chemotherapeutic agents), sunitinib malate (marketed as Sutent® by Pfizer and approved for the treatment of renal cancer) and sorafenib (marketed as Nexavar by Bayer for the treatment of renal cancer).

In addition to the growth factor associated signaling pathways, which predominantly utilize kinase catalyzed transfer of phosphate groups as the key component of the signaling pathway, numerous other signaling pathways also exist within cells and their proper regulation is critical for maintaining correct levels of cell growth and replication. In the emerging area of cancer stem cell inhibition the Wnt, Notch and Hedgehog pathways have received much interest as potential ways in which to avoid tumor relapse and metastasis. The Wnt pathway is instrumental in embryonic development and in tissue maintenance in adults with the activity of individual components within the pathway under tight regulation. In cancer and other diseases cell signaling pathways no longer exhibit the appropriate level of control. In the case of the Wnt pathway, signal transduction is controlled by the relative stabilities of 2 proteins, axin and β-catenin. An overabundance of β-catenin leads to increased Wnt signaling and activation of associated nuclear transcription factors while excess axin results in the degradation of intracellular β-catenin and decreased signaling. Dysregulation of the canonical Wnt signaling pathway has been implicated in a range of human carcinomas such as colon cancer, hepatocellular carcinoma, endometrial ovarian cancer, pilomatricoma skin cancer, prostate cancer, melanoma and Wilms tumor.

In the canonical Wnt signaling pathway signaling is initiated by interaction of a Wnt ligand with a receptor complex containing a Frizzled family member and low-density lipoprotein receptor-related protein. This leads to the formation of a disheveled-frizzled complex and relocation of axin from the destruction complex to the cell membrane. Axin is the concentration limiting component of the destruction complex, and it is this complex which is formed with adenomatous polyposis coli proteins, casein-kinase 1α and glycogen synthase kinase 3β which is responsible for controlling intracellular levels of β-catenin. In the presence of functional destruction complex, β-catenin is sequentially phosphorylated by casein-kinase 1α and glycogen synthase kinase 3β on a conserved set of serine and threonine residues at the amino-terminus. Phosphorylation facilitates binding of β-catenin to β-transducin repeat-containing protein which then mediates ubiquitination and subsequent proteasomal degradation of β-catenin. In the absence of sufficiently elevated concentrations of the destruction complex, un-phosphorylated β-catenin is able to migrate to the cell nucleus and interact with T-cell factor proteins and convert them into potent transcriptional activators through the recruitment of co-activator proteins.

It has recently been reported that intracellular axin levels are influenced by the poly(ADP-ribose) polymerase enzyme family members tankyrase-1 and tankyrase-2 (also known as PARP5a and PARP5b) (*Nature Chemical Biology* 2009, 5, 100 and *Nature* 2009, 461, 614). Tankyrase enzymes are able to poly-ADP ribosylate (PARsylate) axin, which marks this protein for subsequent ubiquitination and proteasomal degradation. Thus, it would be expected that in the presence of an inhibitor of tankyrase catalytic activity, axin protein concentration would be increased, resulting in higher concentration of the destruction complex and decreased concentrations of unphosphorylated intracellular β-catenin and decreased Wnt signaling. An inhibitor of tankyrase-1 and -2 would also be expected to have an effect on other biological functions of the tankyrase proteins e.g. chromosome end protection (telomeres), insulin responsiveness and spindle assembly during mitosis (*Biochimie* 2009, 5, 100).

Therapeutics which are directed at and can correct dysregulation of the Wnt signaling pathway have been implicated in conditions such as bone density defects, coronary disease, late onset Alzheimer's disease, familial exudative vitreoretinopathy, retinal angiogenesis, tetra-amelia, Mullerian-duct regression and virilization, SERKAL syndrome, type 2 diabetes, Fuhrmann syndrome, skeletal dysplasia, focal dermal hypoplasia and neural tube defects. Although the above introduction has focused on the relevance of Wnt signaling in cancer, the Wnt signaling pathway is of fundamental importance and has potential implication in a broad range of human diseases, not necessarily limited to the examples provided above for illustrative purposes.

SUMMARY OF THE INVENTION

There is a continuing need for new and novel therapeutic agents that can be used for cancer and hyperproliferative conditions. The PAK family are important signaling proteins frequently over-expressed and/or overactive in many cancerous tissues. Design and development of new pharmaceutical compounds that inhibit or modulate their activity is essential. In one aspect of the present invention there is provided a compound according to formula I

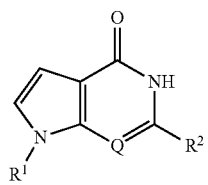

wherein:

Q and X are independently in each occurrence N or CH;

$R_1$ is selected from the group consisting of hydrogen, $C_{1-6}$ alkyl, $C_{1-6}$ alkenyl, $C_{1-6}$ hydroxyalkyl, $C_{1-6}$-dihydroxyalkyl, $C_{3-7}$ cycloalkyl;

$R_2$ is

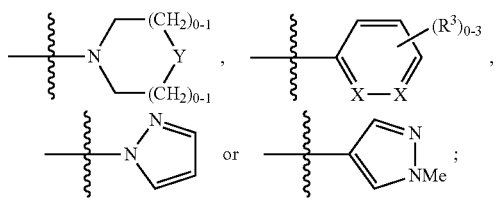

Y is selected from the group consisting of $CR^4R^5$, $NR^4$ or —O— wherein $R^5$ is hydrogen, $C_{1-6}$ alkyl;

$R_4$ is $C_{1-6}$ alkyl, $C_{1-6}$ alkylsulfonyl, $C_{1-6}$ acyl, phenyl or heteroaryl said heteroaryl selected from pyridinyl, pyrazinyl or pyrimidinyl and said phenyl and said heteroaryl optionally substituted by one to three substituents independently selected from the group consisting of halogen, CN, $C_{1-6}$ alkylsulfonyl, $C_{1-6}$ haloalkyl, $C_{1-6}$ hydroxyalkyl, $C_{1-3}$ alkoxy-$C_{1-3}$ alkyl, $C_{1-6}$ alkoxycarbonyl, carboxy, $CONR_{4b}R_{4c}$ wherein $R_{4b}$ and $R_{4c}$ are independently in each occurrence hydrogen or $C_{1-3}$ alkyl and $OR_{4a}$ wherein $R_{4a}$ is selected from the group consisting of (i) hydrogen, (ii) $C_{1-6}$ alkyl, (iii) $C_{1-3}$ alkoxy-$C_{1-3}$ alkyl, (iv) $C_{1-6}$ hydroxyalkyl and (v) $C_{1-6}$ dihydroxyalkyl;

$R_6$ is halogen or hydrogen, $R_3$ is selected from the group consisting of hydrogen, $C_{1-6}$ alkyl, substituted alkyl, $C_{1-6}$ haloalkyl, $C_{1-6}$ hydroxyalkyl, $C_{1-6}$ dihydroxyalkyl, $C_{1-3}$ alkoxy-$C_{1-3}$ alkyl, halogen, CN, trifluoromethyl, $C_{1-6}$ alkoxycarbonyl, $C_{1-6}$ alkylsulfonyl, $CONR_{4b}R_{4c}$ wherein $R_{4b}$ and $R_{4c}$ are independently in each occurrence hydrogen or $C_{1-3}$ alkyl, and $OR_{3a}$ wherein $R_{3a}$ is selected from the group consisting of (i) hydrogen, (ii) $C_{1-6}$ alkyl, (iii) $C_{1-3}$ alkoxy-$C_{1-3}$ alkyl, (iv) $C_{1-6}$ hydroxyalkyl and (v) $C_{1-6}$ dihydroxyalkyl; or, a pharmaceutically acceptable salt thereof.

There are provided compounds of the formula

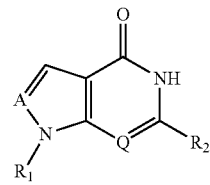

or a pharmaceutically acceptable salt thereof, wherein A, Q, $R_1$ and $R_2$ are as defined below.

The present invention additionally relates to pharmaceutical compositions comprising one or more compounds of the invention, or a pharmaceutically acceptable salt, and a pharmaceutically acceptable carrier or excipient.

The present invention further relates to a method of treating, ameliorating or preventing cancer in a mammal, preferably a human, comprising administering to said mammal a therapeutically effective amount of a compound according to the invention or a pharmaceutically acceptable salt thereof.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such combinations result in stable compounds.

A ⁀⁀⁀⁀ drawn through a bond indicates the point of attachment of a functional group or other chemical moiety to the rest of the molecule of which it is a part. Thus, for example: $MeC(=O)OR^4$ wherein $R^4$ is

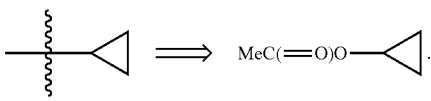

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In one embodiment of the present invention there is provided a compound according to formula Ia:

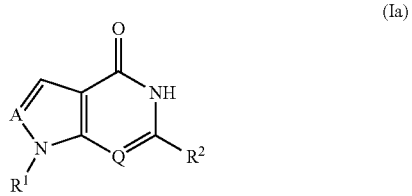

wherein Q is N or CH; A is CH, $R_1$ is selected from the group consisting of hydrogen, alkyl, cycloalkyl, hydroxylalkyl, dihydroxyalkyl and alkenyl, $R_2$ is

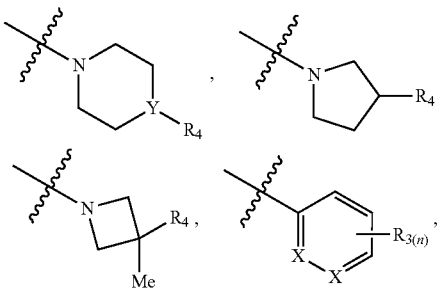

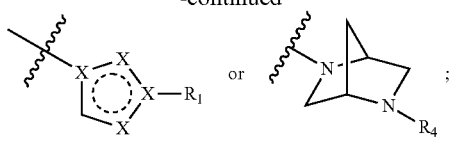

$R_4$ is alkyl, alkylsulfonyl, alkyl ketone or

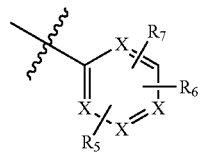

X is CH or N; Y is selected from the group consisting of nitrogen, oxygen or carbon; $R_5$ is halogen, CN, alkylsulfonyl or haloalkyl; $R_6$ is halogen or hydrogen, $R_3$ and $R_7$ is selected from the group consisting of hydrogen, alkyl, substituted alkyl, haloalkyl, halogen, O-alkyl, O-substituted alkyl, CN, trifluoromethyl, carboxyalkyl, alkylsulfonyl and carboxamide; and n is 0 to 3; or a pharmaceutically acceptable salt thereof.

In another embodiment of the present invention there is provided a compound according to formula I wherein $R_1$ is selected from hydrogen or alkyl, $R_2$ is:

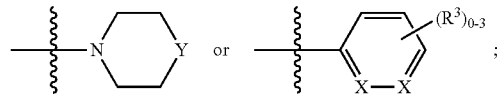

$R_4$ is phenyl or heteroaryl said heteroaryl selected from pyridinyl, pyrazinyl or pyrimidinyl and said phenyl and said heteroaryl optionally substituted by one to three substituents independently selected from the group consisting of halogen, CN, $C_{1-6}$ alkylsulfonyl, $C_{1-6}$ haloalkyl, $C_{1-6}$ hydroxyalkyl, $C_{1-3}$ alkoxy-$C_{1-3}$ alkyl, $C_{1-6}$ alkoxycarbonyl, carboxy, $CONR_{4b}R_{4c}$ wherein $R_{4b}$ and $R_{4c}$ are independently in each occurrence hydrogen or $C_{1-3}$ alkyl and $OR_{4a}$ wherein $R_{4a}$ is selected from the group consisting of (i) $C_{1-6}$ alkyl, (ii) $C_{1-3}$ alkoxy-$C_{1-3}$ alkyl, (iii) $C_{1-6}$ hydroxyalkyl and (iv) $C_{1-6}$ dihydroxyalkyl;

In another embodiment of the present invention there is provided a compound according to formula I which compound is:

7-Methyl-2-(4-pyridin-4-yl-piperazin-1-yl)-3,7-dihydro-pyrrolo[2,3-d]pyrimidin-4-one, 4-[4-(7-Methyl-4-oxo-4,7-dihydro-3H-pyrrolo[2,3-d]pyrimidin-2-yl)-piperazin-1-yl]-benzoic acid ethyl ester, 2-[4-(4-Chloro-phenyl)-piperazin-1-yl]-7-methyl-3,7-dihydro-pyrrolo[2,3-d]pyrimidin-4-one, 7-Methyl-2-(4-pyridin-2-yl-piperazin-1-yl)-3,7-dihydro-pyrrolo[2,3-d]pyrimidin-4-one, 2-[4-(4-Fluoro-2-methanesulfonyl-phenyl)-piperazin-1-yl]-7-methyl-3,7-dihydro-pyrrolo[2,3-d]pyrimidin-4-one, 7-Methyl-2-[4-(3-trifluoromethyl-pyridin-2-yl)-piperazin-1-yl]-3,7-dihydro-pyrrolo[2,3-d]pyrimidin-4-one, 2-[4-(3,5-Dichloro-phenyl)-piperazin-1-yl]-7-methyl-3,7-dihydro-pyrrolo[2,3-d]pyrimidin-4-one, 7-Methyl-2-(4-pyrimidin-2-yl-piperazin-1-yl)-3,7-dihydro-pyrrolo[2,3-d]pyrimidin-4-one, 2-[4-(7-Methyl-4-oxo-4,7-dihydro-3H-pyrrolo[2,3-d]pyrimidin-2-yl)-piperazin-1-yl]-nicotinonitrile, 4-(7-Methyl-4-oxo-4,7-dihydro-3H-pyrrolo[2,3-d]pyrimidin-2-yl)-3,4,5,6-tetrahydro-2H-[1,2']bipyrazinyl-3'-carbonitrile, 7-Methyl-2-(4-methyl-piperazin-1-yl)-3,7-dihydro-pyrrolo[2,3-d]pyrimidin-4-one, 7-Methyl-2-morpholin-4-yl-3,7-dihydro-pyrrolo[2,3-d]pyrimidin-4-one, 2-(4-Methanesulfonyl-piperazin-1-yl)-7-methyl-3,7-dihydro-pyrrolo[2,3-d]pyrimidin-4-one, 2-(4-Acetyl-piperazin-1-yl)-7-methyl-3,7-dihydro-pyrrolo[2,3-d]pyrimidin-4-one, 2-[3-(4-Bromo-phenyl)-3-methyl-azetidin-1-yl]-7-methyl-3,7-dihydro-pyrrolo[2,3-d]pyrimidin-4-one, 7-Methyl-2-(3-phenyl-pyrrolidin-1-yl)-3,7-dihydro-pyrrolo[2,3-d]pyrimidin-4-one, 2-[4-(4-Fluoro-phenyl)-piperazin-1-yl]-7-methyl-3,7-dihydro-pyrrolo[2,3-d]pyrimidin-4-one, 2-[4-(3-Fluoro-phenyl)-piperazin-1-yl]-7-methyl-3,7-dihydro-pyrrolo[2,3-d]pyrimidin-4-one, 2-[4-(7-Methyl-4-oxo-4,7-dihydro-3H-pyrrolo[2,3-d]pyrimidin-2-yl)-piperazin-1-yl]-benzonitrile, 2-[4-(2,4-Difluoro-phenyl)-piperazin-1-yl]-7-methyl-3,7-dihydro-pyrrolo[2,3-d]pyrimidin-4-one, 3-[4-(7-Methyl-4-oxo-4,7-dihydro-3H-pyrrolo[2,3-d]pyrimidin-2-yl)-piperazin-1-yl]-benzonitrile, 4-[4-(7-Methyl-4-oxo-4,7-dihydro-3H-pyrrolo[2,3-d]pyrimidin-2-yl)-piperazin-1-yl]-benzonitrile, 7-Methyl-2-[4-(2-trifluoromethyl-phenyl)-piperazin-1-yl]-3,7-dihydro-pyrrolo[2,3-d]pyrimidin-4-one, 2-[4-(2-Fluoro-4-methanesulfonyl-phenyl)-piperazin-1-yl]-7-methyl-3,7-dihydro-pyrrolo[2,3-d]pyrimidin-4-one, 7-Methyl-2-[4-(4-trifluoromethyl-pyridin-2-yl)-piperazin-1-yl]-3,7-dihydro-pyrrolo one, 2-[4-(3,4-Dichloro-phenyl)-piperazin-1-yl]-7-methyl-3,7-dihydro-pyrrolo[2,3-d]pyrimidin-4-one, 7-But-3-enyl-2-[4-(2-chloro-phenyl)-piperazin-1-yl]-3,7-dihydro-pyrrolo[2,3-d]pyrimidin-4-one, 2-[4-(2-Fluoro-phenyl)-piperazin-1-yl]-7-methyl-3,7-dihydro-pyrrolo[2,3-d]pyrimidin-4-one, 7-Methyl-2-(4-phenyl-piperazin-1-yl)-3,7-dihydro-pyrrolo[2,3-d]pyrimidin-4-one, 2-[4-(2-Chloro-phenyl)-piperazin-1-yl]-7-methyl-3,7-dihydro-pyrrolo[2,3-d]pyrimidin-4-one, 7-Methyl-2-(2,3,5,6-tetrahydro-[1,2']bipyrazinyl-4-yl)-3,7-dihydro-pyrrolo[2,3-d]pyrimidin-4-one, 6-[4-(7-Methyl-4-oxo-4,7-dihydro-3H-pyrrolo[2,3-d]pyrimidin-2-yl)-piperazin-1-yl]-nicotinonitrile, 2-[(1S,4S)-5-(3-Fluoro-phenyl)-2,5-diaza-bicyclo[2.2.1]hept-2-yl]-7-methyl-3,7-dihydro-pyrrolo[2,3-d]pyrimidin-4-one, 2-[4-(3,5-Dichloro-pyridin-4-yl)-piperazin-1-yl]-7-methyl-3,7-dihydro-pyrrolo[2,3-d]pyrimidin-4-one, 6-[4-(2-Fluoro-phenyl)-piperazin-1-yl]-1-methyl-1,5-dihydro-pyrrolo[3,2-c]pyridin-4-one, 1-Ethyl-6-[4-(2-fluoro-phenyl)-piperazin-1-yl]-1,5-dihydro-pyrrolo[3,2-c]pyridin-4-one, 2-(4-Trifluoromethyl-phenyl)-3,7-dihydro-pyrrolo[2,3-d]pyrimidin-4-one, 7-Methyl-2-(4-trifluoromethyl-phenyl)-3,7-dihydro-pyrrolo[2,3-d]pyrimidin-4-one, 2-(4-Methoxy-phenyl)-7-methyl-3,7-dihydro-pyrrolo[2,3-d]pyrimidin-4-one, 2-(6-Ethoxy-pyridin-3-yl)-7-methyl-3,7-dihydro-pyrrolo[2,3-d]pyrimidin-4-one, 7-Methyl-2-pyridin-3-yl-3,7-dihydro-pyrrolo[2,3-d]pyrimidin-4-one, 7-Methyl-2-(6-methyl-pyridin-3-yl)-3,7-dihydro-pyrrolo[2,3-d]pyrimidin-4-one, 4-(7-Methyl-4-oxo-4,7-dihydro-3H-pyrrolo[2,3-d]pyrimidin-2-yl)-benzonitrile, 7-Methyl-2-(6-trifluoromethyl-pyridin-3-yl)-3,7-dihydro-pyrrolo[2,3-d]pyrimidin-4-one, 1-Methyl-6-(4-trifluoromethyl-phenyl)-1,5-dihydro-pyrrolo[3,2-c]pyridin-4-one, 1-Ethyl-6-(4-trifluoromethyl-phenyl)-1,5-dihydro-pyrrolo[3,2-c]pyridin-4-one, 1-Methyl-6-(1-methyl-1H-pyrazol-4-yl)-1,5-dihydro-pyrrolo[3,2-c]pyridin-4-one, 2-[4-(4-Fluoro-phenyl)-piperidin-1-yl]-7-methyl-3,7-dihydro-pyrrolo[2,3-d]pyrimidin-4-one, 7-But-3-enyl-2-(4-trifluoromethyl-phenyl)-3,7-dihydro-pyrrolo[2,3-d]pyrimidin-4-one, 7-Ethyl-2-(4-trifluoromethyl-phenyl)-3,7-dihydro-pyrrolo[2,3-d]pyrimidin-4-one, 7-Propyl-2-(4-trifluoromethyl-phenyl)-3,7-dihydro-pyrrolo[2,3-d]pyrimidin-4-one, 7-Allyl-2-(4-trifluoromethyl-phenyl)-3,7-dihydro-pyrrolo[2,3-d]pyrimidin-4-one, 7-(3,4-Dihydroxy-butyl)-2-(4-trifluoromethyl-phenyl)-3,7-dihydro-pyrrolo[2,3-d]pyrimidin-4-one, 7-(2,3-Dihydroxy-propyl)-2-(4-trifluoromethyl-phenyl)-3,7-dihydro-pyrrolo[2,3-d]pyrimidin-4-one, N-Ethyl-4-[4-(7-methyl-4-oxo-4,7-dihydro-3H-pyrrolo[2,3-d]pyrimidin-2-yl)-piperazin-1-yl]-benzamide, 7-Methyl-2-pyrazol-1-yl-3,7-dihydro-pyrrolo[2,3-d]pyrimidin-4-one, 7-Hydroxymethyl-2-(4-trifluoromethyl-phenyl)-3,7-dihydro-pyrrolo[2,3-d]pyrimidin-4-one, 7-Methyl-2-(3-methyl-3-phenyl-azetidin-1-yl)-3,7-dihydro-pyrrolo[2,3-d]pyrimidin-4-one, 7-Cyclopropyl-2-(4-trifluoromethyl-phenyl)-3,7-dihydro-pyrrolo[2,3-d]pyrimidin-4-one, 2-[4-(2-Fluoro-phenyl)-piperazin-1-yl]-7-hydroxymethyl-3,7-dihydro-pyrrolo[2,3-d]pyrimidin-4-one, 2-[4-(2,6-Difluoro-phenyl)-piperazin-1-yl]-7-(2,3-dihydroxy-propyl)-3,7-dihydro-pyrrolo[2,3-d]pyrimidin-4-one and 7-Methyl-2-phenyl-3,7-dihydro-pyrrolo[2,3-d]pyrimidin-4-one.

In another embodiment of the present invention there is provided a compound according to formula I which compound is 2-[4-[2 6-difluoro-4-(2-methoxyethoxy)phenyl]piperazin-1-yl]-7-(2-hydroxyethyl)-3H-pyrrolo[2,3-d]pyrimidin-4-one.

In another embodiment of the present invention there is provided a method of inhibiting tankyrase 1 and/or tankyrase 2 by contacting either or both with a compound of formula I wherein $R_1$, $R_2$ and Q are as defined hereinabove.

In another embodiment of the present invention there is provided a method of treating cancer by administering to a patient in need thereof a therapeutically active amount of a compound of formula I wherein $R_1$, $R_2$ and Q are as defined hereinabove.

In another embodiment of the present invention there is provided a method of treating colorectal by administering to a patient in need thereof a therapeutically active amount of a compound of formula I wherein $R_1$, $R_2$ and Q are as defined hereinabove.

In another embodiment of the present invention there is provided a compound of formula I wherein $R_1$, $R_2$ and Q are as defined hereinabove for use in the preparation of a medicament for the treatment of cancer.

In another embodiment of the present invention there is provided a pharmaceutical composition comprising a compound of formula I wherein $R_1$, $R_2$ and Q are as defined hereinabove and at least one pharmaceutically acceptable carrier, diluent and/or excipient.

Definitions

As used herein, the following terms shall have the following definitions.

The term "alkyl" refers to straight- or branched-chain saturated hydrocarbon groups having from 1 to about 12 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, preferably from 1 to 4 carbon atoms. Examples of alkyl groups include, but are not limited to, methyl, ethyl, n-propyl, i-propyl, n-butyl, s-butyl, t-butyl, n-pentyl, and s-pentyl.

The term "alkenyl" as used herein means an unsaturated straight-chain or branched aliphatic hydrocarbon group containing at least one double bond and having 2 to 6, preferably 2 to 4 carbon atoms. Examples of such an "alkenyl group" are vinyl, ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkoxy" as used herein means an —O-alkyl group which is attached to the remainder of the molecule by an oxygen atom, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

Amino means the group —$NH_2$.

The term "aryl" as used herein denotes a monovalent aromatic carbocyclic radical containing 6 to 10 carbon atoms consisting of one individual ring, or one or more fused rings wherein the fused rings may be aromatic, partially unsaturated or saturated and wherein the aryl is attached to the remainder of the molecule at the aromatic ring. An aryl group can optionally be substituted with one or more, preferably one to three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, dialkylaminoalkyl, alkylsulfonyl, arylsulfinyl, alkylaminosulfonyl, arylaminosulfonyl, alkylsulfonylamido, arylsulfonylamido, carbamoyl, alkylcarbamoyl dialkylcarbamoyl, arylcarbamoyl, alkylcarbonylamino and arylcarbonylamino, unless otherwise indicated. Alternatively two adjacent atoms of the aryl ring may be substituted with a methylenedioxy or ethylenedioxy group. Examples of aryl radicals include phenyl, naphthyl, indanyl, 3,4-methylenedioxyphenyl, 1,2,3,4-tetrahydroquinolin-7-yl, 1,2,3,4-tetrahydroisoquinoline-7-yl, and the like.

Carboxyl or carboxy means the monovalent group C(=O)OH.

The terms "alkoxycarbonyl" and "aryloxycarbonyl" as used herein denotes a group of —C(=O)OR wherein R is alkyl or aryl respectively and alkyl and aryl are as defined herein.

Carbonyl means the group R'C(=O)R" where R' and R" independently can be any of a number of chemical groups including alkyl. The term "acyl", "alkanoyl" or "alkylcarbonyl" as used herein denotes a group of formula —C(=O)R wherein R is hydrogen or lower alkyl as defined herein. The term $C_{1-6}$ acyl [or "alkanoyl"] refers to a group —C(=O)R contain 1 to 6 carbon atoms. The $C_1$ acyl or "alkanoyl" group is the formyl group wherein R=H. The term "arylcarbonyl" or "aroyl" as used herein means a group of formula C(=O)R wherein R is an aryl group; the term "benzoyl" as used herein an "arylcarbonyl" or "aroyl" group wherein R is phenyl.

The term "cycloalkyl" as used herein means any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "halogen" as used herein means fluorine, chlorine, bromine, or iodine, preferably fluorine and chlorine.

"Heteroaryl" means an aromatic heterocyclic ring system containing up to two rings. In one embodiment of the invention heteroaryl groups include, but are not limited to, thienyl, furyl, indolyl, pyrrolyl, pyridinyl, pyrazinyl, oxazolyl, thiaxolyl, quinolinyl, pyrimidinyl, imidazole substituted or unsubstituted triazolyl and substituted or unsubstituted tetrazolyl.

"Hetero atom" means an atom selected from N, O and S.

"Heterocycle" or "heterocyclic ring" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. When the heterocycle is bicyclic one ring can lack a heteroatom and be aromatic, partially unsaturated or saturated but heterocycle is attached to the remainder of the molecule at the heterocyclic ring. Examples include pyrrolidin-2-yl; pyrrolidin-3-yl; piperidinyl; morpholin-4-yl and the like which in turn can be substituted.

Hydroxy or hydroxyl is a prefix indicating the presence of a monovalent OH group.

"Lower" as in "lower alkenyl" means a group having 1 to 6 carbon atoms.

"Nitro" means —$NO_2$.

"Oxo" means the group =O.

The terms "alkylsulfonyl" and "arylsulfonyl" as used herein denotes a group of formula —$S(=O)_2R$ wherein R is alkyl or aryl respectively and alkyl and aryl are as defined herein. The terms $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl refer to a compound, $S(=O)_2R$ wherein R is $C_{1-6}$ haloalkyl, $C_{3-7}$ cycloalkyl, $C_{3-7}$ cycloalkyl-$C_{1-3}$ alkyl and $C_{1-6}$ alkoxy-$C_{1-6}$ alkyl, respectively.

The terms "hydroxyalkyl" and "alkoxyalkyl" as used herein denotes alkyl radical as herein defined wherein one hydrogen atom is replaced by a hydroxyl. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom. "Dihydroxyalkyl" as used herein denotes alkyl radical as herein defined wherein two hydrogen atoms on different carbon atoms are replaced by hydroxyl.

The term "haloalkyl" as used herein denotes an alkyl group as defined above wherein at least one hydrogen atom is substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 2-fluoroethyl, 2-chloroethyl, 2-bromoethyl, 2,2-dichloroethyl, 3-bromopropyl or 2,2,2-trifluoroethyl.

The term "haloalkyl" as used herein denotes an alkyl group as defined above wherein at least one hydrogen atom is substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 2-fluoroethyl, 2-chloroethyl, 2-bromoethyl, 2,2-dichloroethyl, 3-bromopropyl or 2,2,2-trifluoroethyl The term "alkoxyalkyl" as used herein refers to the radical R'R"—, wherein R' is an alkoxy radical as defined herein, and R" is an alkylene radical as defined ith the understanding that the attachment point of the alkoxyalkyl moiety will be on the alkylene radical. $C_{1-6}$ alkoxyalkyl denotes a group wherein the alkyl portion is comprised of 1-6 carbon atoms exclusive of carbon atoms in the alkoxy portion of the group. $C_{1-3}$ alkoxy-$C_{1-6}$ alkyl denotes a group wherein the alkyl portion is comprised of 1-6 carbon atoms and the alkoxy group is 1-3 carbons. Examples include, but are not limited to, methoxymethyl, methoxyethyl, methoxypropyl, ethoxyethyl, ethoxypropyl, propyloxypropyl, methoxybutyl, ethoxybutyl, butyloxybutyl, t-butyloxybutyl ethoxypentyl, propyloxypentyl including their isomers.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —$CH_2CH$(i-Pr)$CH_2$—), unless otherwise indicated. $C_{0-4}$ alkylene or (alkylene)$_{0-4}$ refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Another embodiment includes a pharmaceutical composition comprising a compound of Formula I for use in the treatment of a hyperproliferative disease. Another embodiment includes a pharmaceutical composition comprising a compound of Formula I for use in the treatment of cancer.

"Substituted," as in substituted alkyl, means that the substitution can occur at one or more positions and, unless otherwise indicated, that the substituents at each substitution site are independently selected from the specified options. The term "optionally substituted" refers to the fact that one or more hydrogen atoms of a chemical group (with one or more hydrogen atoms) can be, but does not necessarily have to be, substituted with another substituent. In the specification where indicated the various groups may be substituted by preferably, 1-3 substituents independently selected from the group consisting of H, carboxyl, amido, hydroxyl, alkoxy, substituted alkoxy, sulfide, sulfone, sulfonamide, sulfoxide, halogen, nitro, amino, substituted amino, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle or substituted heterocycle.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

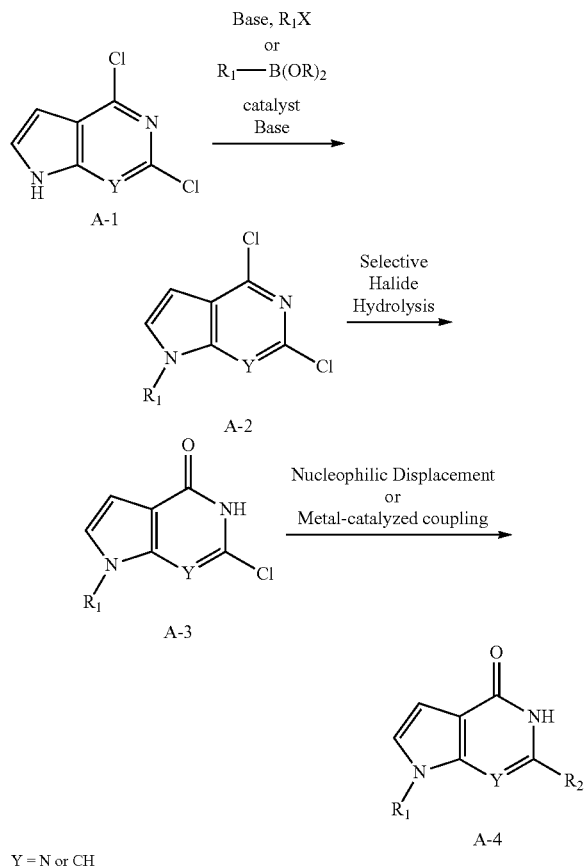

Y = N or CH

The compounds of formula A-2 where $R_1$ is hydrogen and Y is nitrogen or carbon can be purchased from commercial sources.

The compound of formula A-2 where $R_1$ is lower alkyl or alkenyl and where Y is nitrogen or carbon can be prepared by reacting the appropriate heterocyclic starting material with a commercially available or a synthetically prepared halide of the corresponding lower alkyl or alkenyl derivative under basic conditions (see for example, Chuaqui, C. E.; Huang, S.; Ioannidis, S.; Shi, J.; Su, M.; Su, Q., WO2010/038060 A1; Bursavich, M. G.; Nowak, P. W.; Malwitz, D.; Lombardi, S.; Gilbert, A. M.; Zhang, N.; Ayral-Kaloustian, S.; Anderson, J. T.; Brooijmans, N., US2010/0015141A1). The lower alkyl or alkenyl derivative may be in a protected form that may be deprotected at some point in the synthesis. The lower alkyl or alkenyl derivative could also be transformed through standard chemical manipulation.

The compound of formula A-2 where $R_1$ is cycloalkyl and where Y is nitrogen or carbon can be prepared by reacting the appropriate amine compound with a commercially available or a synthetically prepared boronic acid or boronate ester of the corresponding cycloalkyl derivative under metal catalyzed coupling conditions (see for example, Dillon, M. P., Du Bois, D. J., Lai, Y., Hawley, R. C., Wang, B., US 2010/0144758). The cycloalkyl group may be in a protected form that may be deprotected at some point in the synthesis.

The compound of formula A-3 where $R_1$ is hydrogen and where Y is nitrogen can be prepared from the compound of formula A-2 where $R_1$ is hydrogen by heating under basic aqueous conditions (Zhang, Z., Wallace, M. B., Feng, J., Stafford, J. A., Skene, R. J., Shi, L., Lee, B., Aertgeerts, K., Jennings, A., Xu, R., Kassel, D. B., Kaldor, S. W., Navre, M., Webb, D. R., Gwaltney, S. L, II, J. Med. Chem., 2011, 54(2), 510-524).

The compound of formula A-3 where $R_1$ is lower alkyl, alkenyl or cycloalkyl and where Y is nitrogen or carbon can be prepared from the compound of formula A-2 where $R_1$ is lower alkyl, alkenyl or cycloalkyl, Y is nitrogen or carbon by heating under basic aqueous condition (see for example, Zhang, Z., Wallace, M. B., Feng, J., Stafford, J. A., Skene, R. J., Shi, L., Lee, B., Aertgeerts, K., Jennings, A., Xu, R., Kassel, D. B., Kaldor, S. W., Navre, M., Webb, D. R., Gwaltney, S. L, II, J. Med. Chem., 2011, 54(2), 510-524). The lower alkyl, alkenyl or cycloalkyl group may be in a protected form that may be deprotected at some point in the synthesis. The lower alkyl or alkenyl derivative could also be transformed through standard chemical manipulation.

The compound of formula A-4 where $R_1$ is lower alkyl, alkenyl or cycloalkyl and where Y is nitrogen or carbon and $R_2$ is an appropriately substituted secondary or tertiary amino group can be prepared from the compound of formula A-3 where $R_1$ is lower alkyl, alkenyl or cycloalkyl and where Y is nitrogen or carbon through nucleophilic displacement of the chloro of the compound of formula A-3 with an appropriately substituted primary or secondary amino group (see for example, Ram, V. J., Farhanullah, Tripathi, B. K., Srivastava, A. K., Bioorg. Med. Chem., 2003, 11, 2439-2444). The amine reagent may be appropriately protected or functionalized such that upon displacement of the chloro the protecting group could be removed and/or the various functionalities could be further elaborated. The amine reagent may be commercially available or may be prepared through standard synthetic manipulation. The lower alkyl, alkenyl or cycloalkyl derivative of $R_1$ may be in a protected form that may be deprotected at some point in the synthesis. The lower alkyl, alkenyl or cycloalkyl derivative of $R_1$ derivative could also be transformed through standard chemical manipulation.

The compound of formula A-4 where $R_1$ is lower alkyl, alkenyl or cycloalkyl and where Y is nitrogen or carbon and $R_2$ is aryl, substituted aryl, heteroaryl or substituted heteroaryl can be prepared from the compound of formula A-3 where $R_1$ is lower alkyl, alkenyl or cycloalkyl and where Y is nitrogen or carbon through a metal catalyzed coupling reaction using a reagent containing a boronic acid or boronate ester of a aryl, substituted aryl, heteroaryl or substituted heteroaryl (see for example, Denny, W. A., Baguley, B. C., Marshall, E. S., Sutherland, H. S., WO2007/117161 A1). The lower alkyl, alkenyl or cycloalkyl derivative of $R_1$ may be in a protected form that may be deprotected at some point in the synthesis. The lower alkyl, alkenyl or cycloalkyl derivative of $R_1$ derivative could also be transformed through standard chemical manipulation.

The compound of formula A-4 where $R_1$ is hydrogen and where Y is nitrogen and $R_2$ is aryl, substituted aryl, heteroaryl or substituted heteroaryl can be prepared from the compound of formula A-3 where $R_1$ is hydrogen and where Y is nitrogen or carbon through a metal catalyzed coupling reaction using a reagent containing a boronic acid or boronate ester of a aryl, substituted aryl, heteroaryl or substituted heteroaryl (see for example, Denny, W. A., Baguley, B. C., Marshall, E. S., Sutherland, H. S., WO2007/117161 A1).

The following preparations and examples are given to enable those skilled in the art to more clearly understand and to practice the present invention. They should not be considered as limiting the scope of the invention, but merely as being illustrative and representative thereof.

| Abbreviations | |
|---|---|
| Ac₂O | Acetic anhydride |
| AcOH | Acetic acid |
| DBU | 1,8-Diazabicyclo[5.4.0]undec-7-ene |
| DCE | 1,2-Dichloroethane |
| DCM | Dichloromethane/Methylene chloride |
| DIPEA | Diisopropylethylamine |
| DMF | N,N-dimethylformamide |
| DMSO | Dimethyl sulfoxide |
| EDCI | 1-(3-Dimethylaminopropyl)-3-ethylcarbodiimide |
| Et₂O | Diethyl ether |
| EtOH | Ethanol/Ethyl alcohol |
| EtOAc | Ethyl acetate |
| IWR2 | 4-((1S,2R,6S,7R)-3,5-Dioxo-4-aza-tricyclo[5.2.1.0*2,6*]dec-8-en-4-yl)-N-(4-methyl-quinolin-8-yl)-benzamide |
| HOBt | 1-Hydroxybenzotriazole |
| LDA | Lithium diisopropylamide |
| LiHMDS | Lithium bis(trimethylsilyl)amide |
| m-CPBA | 3-Chloroperoxybenzoic acid |
| MeOH | Methanol/Methyl alcohol |
| MW | Molecular Weight |
| NMP | 1-Methyl-2-pyrrolidinone |
| PMB | 4-Methoxy benzyl |
| RT | Room temperature |
| TBME | tert-Butyl methyl ether |
| TFA | Trifluoroacetic acid |
| Tf₂O | Trifluoromethanesulfonic anhydride |
| THF | Tetrahydrofuran |
| TLC | Thin layer chromatography |
| TNKS | Tankyrase |
| Tris | 2-amino-2-hydroxymethyl-propane-1,3-diol |
| XAV939 | 2-(4-Trifluoromethyl-phenyl)-3,5,7,8-tetrahydro-thiopyrano[4,3-d]pyrimidin-4-one |

General Conditions

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991;

Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Preparative reverse-phase high-pressure liquid chromatography (RP HPLC) was performed using one of the following systems: (A). a Waters Delta prep 4000 pump/controller, a 486 detector set at 215 nm, and a LKB Ultrorac fraction collector; or (B). a Sciex LC/MS system with a 150 EX single quad mass spec, a Shimadzu LC system, a LEAP autoinjector, and a Gilson fraction collector. The sample was dissolved in a mixture of acetonitrile/20 mM aqueous ammonium acetate or acetonitrile/water/TFA, applied on a Pursuit C-18 20×100 mm column and eluted at 20 mL/min with a linear gradient of 10%-90% B, where (A): 20 mM aqueous ammonium acetate (pH 7.0) and (B): acetonitrile or (A): water with 0.05% TFA and (B): acetonitrile with 0.05% TFA.

Flash chromatography was performed using standard silica gel chromatography, pre-packed silica columns (Analogix) with an Analogix BSR pump system or Analogix IntelliFlash Automated systems. Reactions heated in a microwave were performed using the Biotage Initiator 60 microwave or the CEM Explore microwave.

PREPARATIVE EXAMPLES

Intermediate A

2-Chloro-7-methyl-3,7-dihydro-pyrrolo[2,3-d]pyrimidin-4-one

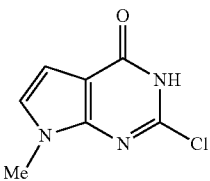 [SMILES: Cn1ccc2c(=O)[nH]c(Cl)nc21]

Step 1: A solution of 2,4-dichloro-7H-pyrrolo[2,3-d]pyrimidine (3.00 g, 16.0 mmol) in anhydrous tetrahydrofuran (45 mL) was cooled to 0° C. and treated with a 60% dispersion of sodium hydride in mineral oil (0.83 g, 20.8 mmol). The reaction was stirred at 0° C. for 20-30 min. The reaction was then treated with iodomethane (3.65 g, 1.6 mL, 25.7 mmol), and the reaction stirred at room temperature overnight. The reaction was diluted with a saturated aqueous ammonium chloride solution (50 mL) and water (50 mL) and was extracted with a 10% methanol in methylene chloride solution (4×50 mL). The combined organic layers were dried over magnesium sulfate, filtered and rinsed with methylene chloride, and concentrated in vacuo onto Celite®. Flash chromatography (80 g silica gel column, 0-15% ethyl acetate/hexanes) afforded 2,4-dichloro-7-methyl-7H-pyrrolo[2,3-d]pyrimidine as a light yellow solid (2.39 g, 74.1%). $^1$H NMR (400 MHz, DMSO-d$_6$) δ ppm 3.81 (s, 3H) 6.70 (d, J=3.51 Hz, 1H) 7.76 (d, J=3.51 Hz, 1H). LC-MS calcd. for C$_7$H$_6$Cl$_2$N$_3$ [(M+H)$^+$] 202, obsd. 202.0.

Step 2: 2,4-dichloro-7-methyl-7H-pyrrolo[2,3-d]pyrimidine (2.39 g, 11.8 mmol) was treated with a 2M aqueous potassium hydroxide solution (70 mL, 140 mmol). The reaction was warmed to 100° C., where it was stirred overnight. The reaction was allowed to cool down to room temperature gradually, where it stirred for an additional 2 nights. The reaction was brought to pH ~7-8 with a 3N aqueous hydrochloric acid solution. The resulting light yellow mixture was cooled in an ice/water bath and filtered, rinsing twice with a small amount of water. The filtrate was brought to pH ~2-3 with additional 3N aqueous hydrochloric acid solution. The resulting opaque light yellow mixture was filtered through the original filter cake. The solids were dried in vacuo to afford 2-chloro-7-methyl-3,7-dihydro-pyrrolo[2,3-d]pyrimidin-4-one as an off-white solid (2.18 g, 100%). NMR (300 MHz, DMSO-d$_6$) δ ppm 3.67 (s, 3H) 6.46 (d, J=3.39 Hz, 1H) 7.11 (d, J=3.39 Hz, 1H) 12.83 (br. s., 1H). LC-MS calcd. for C$_7$H$_7$ClN$_3$O [(M+H)$^+$] 184, obsd, 183.9.

In an analogous manner to the stepwise sequence outlined for the synthesis of Intermediate A, the following compounds were prepared as follows:

Intermediate B

7-But-3-enyl-2-chloro-3,7-dihydro-pyrrolo[2,3-d]pyrimidin-4-one

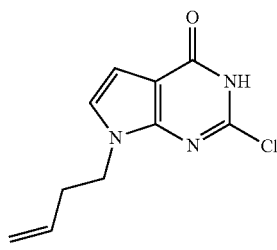

From 2,4-dichloro-7H-pyrrolo[2,3-d]pyrimidine and 4-bromobut-1-ene: crude 7-(but-3-enyl)-2,4-dichloro-7H-pyrrolo[2,3-d]pyrimidine was obtained as a light brown solid (0.66 g, 85.4%). $^1$H NMR (300 MHz, DMSO-d$_6$) δ ppm 2.47-2.68 (m, 2H) 4.31 (t, J=6.97 Hz, 2H) 4.80-5.16 (m, 2H) 5.59-5.93 (m, 1H) 6.70 (d, J=3.58 Hz, 1H) 7.82 (d, J=3.58 Hz, 1H).

From crude 7-(but-3-enyl)-2,4-dichloro-7H-pyrrolo[2,3-d]pyrimidine: 7-but-3-enyl-2-chloro-3,7-dihydro-pyrrolo[2,3-d]pyrimidin-4-one was obtained as a light yellow solid (184.3 mg, 30.2%). NMR (300 MHz, DMSO-d$_6$) δ ppm 2.43-2.56 (m, 2H) 4.14 (t, J=7.06 Hz, 2H) 4.81-5.16 (m, 2H) 5.75 (ddt, J=17.10, 10.31, 6.64, 6.64 Hz, 1H) 6.46 (d, J=3.39 Hz, 1H) 7.17 (d, J=3.39 Hz, 1H) 12.84 (br. s., 1H). LC-MS calcd. for C$_{10}$H$_{11}$ClN$_3$O [(M+H)$^+$] 224, obsd. 224.0.

Intermediate C

2-Chloro-7-ethyl-3,7-dihydro-pyrrolo[2,3-d]pyrimidin-4-one

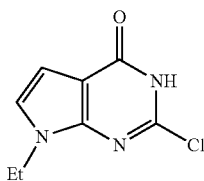 [SMILES: CCn1ccc2c(=O)[nH]c(Cl)nc21]

From 2,4-dichloro-7H-pyrrolo[2,3-d]pyrimidine and iodoethane: 2,4-dichloro-7-ethyl-7H-pyrrolo[2,3-d]pyrimidine was obtained as a white solid (129.1 mg, 74.9%). $^1$H NMR (300 MHz, DMSO-d$_6$) δ ppm 1.38 (t, J=7.35 Hz, 3H) 4.26 (q, J=7.22 Hz, 2H) 6.71 (d, J=3.58 Hz, 1H) 7.85 (d, J=3.58 Hz, 1H). LC-MS calcd. for C$_8$H$_8$Cl$_2$N$_3$ [(M+H)$^+$] 216, obsd. 215.8.

From 2,4-dichloro-7-ethyl-7H-pyrrolo[2,3-d]pyrimidine: 2-chloro-7-ethyl-3,7-dihydro-pyrrolo[2,3-d]pyrimidin-4-one was obtained as an off-white solid (96.4 mg, 84.3%). $^1$H NMR (300 MHz, DMSO-d$_6$) δ ppm 1.32 (t, J=7.25 Hz, 3H) 4.10 (q, J=7.22 Hz, 2H) 6.47 (d, J=3.39 Hz, 1H) 7.19 (br. s., 1H) 12.83 (br. s., 1H). LC-MS calcd. for C$_8$H$_9$ClN$_3$O [(M+H)$^+$] 198, obsd. 197.9.

Intermediate D

2-Chloro-7-propyl-3,7-dihydro-pyrrolo[2,3-d]pyrimidin-4-one

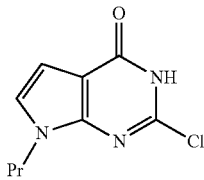

From 2,4-dichloro-7H-pyrrolo[2,3-d]pyrimidine and 1-iodopropane: 2,4-dichloro-7-propyl-7H-pyrrolo[2,3-d]pyrimidine was obtained as a light yellow semi-solid (122.4 mg, 50%). $^1$H NMR (300 MHz, DMSO-d$_6$) δ ppm 0.83 (br. s., 3H) 1.80 (br. s., 2H) 4.19 (br. s., 2H) 6.71 (br. s., 1H) 7.83 (br. s., 1H). LC-MS calcd. for C$_9$H$_{10}$Cl$_2$N$_3$ [(M+H)$^+$] 230, obsd. 229.87.

From 2,4-dichloro-7-propyl-7H-pyrrolo[2,3-d]pyrimidine: 2-chloro-7-propyl-3,7-dihydro-pyrrolo[2,3-d]pyrimidin-4-one was obtained as a light yellow solid (104.3 mg, 94.5%). NMR (400 MHz, DMSO-d$_6$) δ ppm 0.81 (t, J=7.42 Hz, 3H) 1.73 (sxt, J=7.27 Hz, 2H) 4.01 (t, J=7.23 Hz, 2H) 6.46

(d, J=3.52 Hz, 1H) 7.15 (br. s., 1H) 12.82 (br. s., 1H). LC-MS calcd. for $C_9H_{11}ClN_3O$ $[(M+H)^+]$ 212, obsd. 212.0.

Intermediate E

7-Allyl-2-chloro-3,7-dihydro-pyrrolo[2,3-d]pyrimidin-4-one

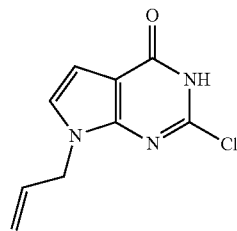

From 2,4-dichloro-7H-pyrrolo[2,3-d]pyrimidine and 3-iodoprop-1-ene: 7-allyl-2,4-dichloro-7H-pyrrolo[2,3-d]pyrimidine was obtained as a light yellow solid (130.1 mg, 53.6%). $^1$H NMR (400 MHz, DMSO-$d_6$) δ ppm 4.88 (dt, J=5.37, 1.61 Hz, 2H) 4.99 (dq, J=17.09, 1.46 Hz, 1H) 5.20 (dq, J=10.30, 1.38 Hz, 1H) 6.04 (ddt, J=17.09, 10.45, 5.37, 5.37 Hz, 1H) 6.75 (d, J=3.52 Hz, 1H) 7.76 (d, J=3.91 Hz, 1H). LC-MS calcd. for $C_9H_8Cl_2N_3$ $[(M+H)^+]$ 228, obsd. 227.9.

From 7-allyl-2,4-dichloro-7H-pyrrolo[2,3-d]pyrimidine: 7-allyl-2-chloro-3,7-dihydro-pyrrolo[2,3-d]pyrimidin-4-one was obtained as a light yellow solid (104.4 mg, 88.7%). $^1$H NMR (400 MHz, DMSO-$d_6$) δ ppm 4.72 (d, J=5.47 Hz, 2H) 4.97 (dd, J=17.19, 1.56 Hz, 1H) 5.17 (dd, J=10.16, 1.56 Hz, 1H) 5.92-6.11 (m, 1H) 6.52 (d, J=3.13 Hz, 1H) 7.12 (br. s., 1H) 12.89 (br. s., 1H). LC-MS calcd. for $C_9H_9ClN_3O$ $[(M+H)^+]$ 210, obsd. 209.9.

Intermediate F

2-Chloro-3,7-dihydro-pyrrolo[2,3-d]pyrimidin-4-one

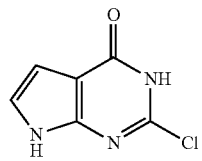 [SMILES: O=c1[nH]c(Cl)nc2[nH]ccc12]

A solution of 2,4-dichloro-7H-pyrrolo[2,3-d]pyrimidine (400 mg, 2.13 mmol) in a 2M aqueous potassium hydroxide solution (12 mL) was heated to 100° C. for 4 h. At this time, the resulting mixture was poured onto iced water and then acidified to pH 6.5 with a 6M aqueous hydrochloric acid solution. The acidic solution was extracted with ethyl acetate. The combined organics were washed with a saturated aqueous sodium chloride solution, dried over sodium sulfate, filtered and concentrated in vacuo. The resulting residue was triturated with acetonitrile and ether to afford 2-chloro-3,7-dihydro-pyrrolo[2,3-d]pyrimidin-4-one. $^1$HNMR (400 MHz, DMSO-$d_6$) δ ppm 6.40-6.48 (m, 1H) 7.01-7.10 (m, 1H) 12.0 (s, 1H) 12.8 (s, 1H).

Intermediate G

6-Chloro-1-methyl-1,5-dihydro-pyrrolo[3,2-c]pyridine-4-one

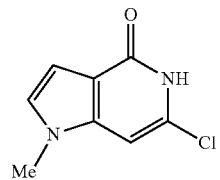 [SMILES: Cn1ccc2c(=O)[nH]c(Cl)cc21]

Step 1: A solution of 4,6-dichloro-1H-pyrrolo[3,2-c]pyridine (270 mg, 1.44 mmol) in tetrahydrofuran (4 mL) at 0° C. was treated with a 60% dispersion of sodium hydride in mineral oil (69.3 mg, 2.89 mmol) followed by iodomethane (225 mg, 1.59 mmol). After stirring at 0° C. for 0.5 h, the reaction mixture was allowed to warm to room temperature and was stirred at room temperature for 5 h. At this time, the resulting mixture was quenched with a saturated aqueous sodium bicarbonate solution. The reaction mixture was extracted with ethyl acetate. The combined organics were washed with a saturated aqueous sodium chloride solution, dried over sodium sulfate, filtered and concentrated in vacuo. Flash chromatography (30% ethyl acetate/hexanes) afforded 4,6-dichloro-1-methyl-1H-pyrrolo[3,2-c]pyridine (278 mg, 95.8%). LC-MS calcd. for $C_8H_6Cl_2N_2$ $[(M+H)^+]$ 201, obsd. 200.8.

Step 2: A microwave reaction vial was charged with 4,6-dichloro-1-methyl-1H-pyrrolo[3,2-c]pyridine (60 mg, 0.29 mmol), a 2M aqueous sodium hydroxide solution (10 mL) and 1,4-dioxane (1 mL). The vial was sealed and then heated in the microwave at 160° C. for 30 min. At this time, the resulting mixture was acidified to pH 6.5 with a 4M aqueous hydrochloric acid solution and then concentrated in vacuo. The residue was diluted with ethanol. The solids were removed by filtration, and the filtrate was concentrated in vacuo. Flash chromatography (10/1 methylene chloride/methanol) afforded 6-chloro-1-methyl-1,5-dihydro-pyrrolo[3,2-c]pyridine-4-one (51 mg, 93.6%). LC-MS calcd. for $C_8H_7ClN_2O_2$ $[(M+H)^+]$ 183, obsd. 182.9.

Intermediate H

6-Chloro-1-ethyl-1,5-dihydro-pyrrolo[3,2-c]pyridine-4-one

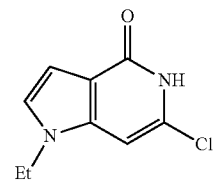 [SMILES: CCn1ccc2c(=O)[nH]c(Cl)cc21]

Step 1: A solution of 4,6-dichloro-1H-pyrrolo[3,2-c]pyridine (250 mg, 1.34 mmol) in tetrahydrofuran (4 mL) at 0° C. was treated with a 60% dispersion of sodium hydride in mineral oil (64.2 mg, 2.67 mmol) followed by iodoethane (229 mg, 1.47 mmol). After stirring at 0° C. for 0.5 h, the reaction mixture was allowed to warm to room temperature and was stirred at room temperature overnight. At this time, the resulting mixture was quenched with a saturated aqueous sodium bicarbonate solution. The reaction mixture was extracted with ethyl acetate. The combined organics were washed with a saturated aqueous sodium chloride solution, dried over sodium sulfate, filtered and concentrated in vacuo. Flash chromatography (30% ethyl acetate/hexane) afforded 4,6-dichloro-1-ethyl-1H-pyrrolo[3,2-c]pyridine (200 mg, 69.6%). LC-MS calcd. for $C_9H_8Cl_2N_2$ [(M)$^+$] 214, obsd. 214.9.

Step 2: A microwave reaction vial was charged with 4,6-dichloro-1-ethyl-1H-pyrrolo[3,2-c]pyridine (200 mg, 0.930 mmol), a 2M aqueous sodium hydroxide solution (10 mL) and 1,4-dioxane (3 mL). The vial was sealed and then heated in the microwave at 160° C. for 30 min. At this time, the resulting mixture was acidified to pH 6.5 with a 4M aqueous hydrochloric acid solution and then concentrated in vacuo. The residue was diluted with ethanol. The solids were removed by filtration, and the filtrate was concentrated in vacuo. Flash chromatography (10/1 methylene chloride/methanol) afforded 6-chloro-1-ethyl-1,5-dihydro-pyrrolo[3,2-c]pyridine-4-one (60 mg, 32.8%). LC-MS calcd. for $C_9H_9ClN_2O$ [(M)$^+$] 196, obsd. 196.9.

Intermediate I 3-(4-Bromo-phenyl)-3-methyl-azetidine

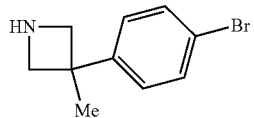

Step 1: To a stirred solution of 2-(4-bromo phenyl) acetonitrile (20 g, 102.04 mmol) in dry tetrahydrofuran (200 mL) was added sodium bis(trimethylsilyl)amide (18.71 g, 102.04 mmol) at 0° C. under a nitrogen atmosphere. After stirring for 20 minutes at room temperature, methyl iodide (14.48 g, 102 mmol) was added and then stirred for 1 h at room temperature. The reaction mixture was quenched with an aqueous ammonium chloride solution and extracted with ethyl acetate (2×150 mL). The combined organic layers were washed with water (2×100 mL), a saturated aqueous sodium chloride solution (2×25 mL), dried over anhydrous sodium sulfate, filtered and concentrated in vacuo. Flash chromatography (3-4% ethyl acetate/hexanes) afforded 2-(4-bromo-phenyl)-propionitrile as a light yellow liquid (11.5 g, 53.6%).

Step 2: To a stirred solution of 2-(4-bromo-phenyl)-propionitrile (27 g, 128.5 mmol) in pyridine (225 mL) was added paraformaldehyde (15.7 g, 514.3 mmol) and a 40% Triton-B solution (in methanol) (14.4 mL). Then the reaction mixture stirred at room temperature for 16 h. At this time, the reaction mixture was diluted with water (10 mL) and extracted with ethyl acetate (300 mL). The organic layer was washed with a 2N aqueous hydrochloric acid solution (2×200 mL), water (2×100 mL), sodium bicarbonate (2×50 mL), a saturated aqueous sodium chloride solution (50 mL), dried over anhydrous sodium sulfate, and concentrated in vacuo. Flash chromatography afforded 2-(4-bromo-phenyl)-3-hydroxy-2-methyl-propionitrile as colorless oil (25.9 g, 84%).

Step 3: To a stirred solution of 2-(4-bromo-phenyl)-3-hydroxy-2-methyl-propionitrile (25 g, 104.17 mmol) in pyridine (225 mL) was added para-toluene sulphonyl chloride (29.79 g, 156.25 mmol) and the reaction stirred at room temperature for 16 h. The reaction mixture was diluted with ethyl acetate (300 mL), washed with a 2N aqueous hydrochloric acid solution (2×50 mL), water (2×100 mL), a saturated aqueous sodium bicarbonate solution (2×50 mL), dried over sodium sulfate, and concentrated in vacuo. Flash chromatography (10% ethyl acetate/hexanes) afforded toluene-4-sulfonic acid 2-(4-bromo-phenyl)-2-cyano-2-methyl-ethyl ester as a colorless liquid (35 g, 73%).

Step 4: To a stirred solution of toluene-4-sulfonic acid 2-(4-bromo-phenyl)-2-cyano-2-methyl-ethyl ester (10 g, 25.38 mmol) in dry tetrahydrofuran (100 mL) was added 1M lithium aluminum hydride (25.3 mL diluted with 25.3 mL of dry tetrahydrofuran) via syringe pump at −10° C. for 1 h and stirring was continued for 30 min at 10° C. The reaction mixture was quenched with water (1 mL), diluted with tetrahydrofuran (3 mL) followed by a 15% aqueous sodium hydroxide solution (1 mL) and water (3 mL), and filtered through a Celite® pad. The filtrate was concentrated in vacuo. Flash chromatography (8% methanol/methylene chloride) afforded 3-(4-bromo-phenyl)-3-methyl-azetidine as an off-white solid (4.0 g, 70%). $^1$H NMR (400 MHz, DMSO-d$_6$) δ ppm 1.52 (s, 3H) 2.42-2.57 (m, 1H) 3.40 (d, J=7.34 Hz, 2H) 3.72 (d, J=7.34 Hz, 2H) 7.15 (d, J=8.80 Hz, 2H) 7.39-7.61 (m, 2H). LC-MS calcd. for $C_{10}H_{12}BrN$ [M$^+$] 226, obsd. 226.0/228.2.

Example 1

7-Methyl-2-(4-pyridin-4-yl-piperazin-1-yl)-3,7-dihydro-pyrrolo[2,3-d]pyrimidin-4-one

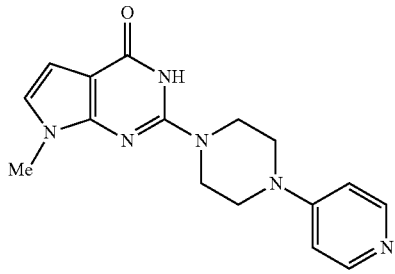 [SMILES: Cn1ccc2c(=O)[nH]c(N3CCN(c4ccncc4)CC3)nc21]

A solution of 2-chloro-7-methyl-3,7-dihydro-pyrrolo[2,3-d]pyrimidin-4-one (Intermediate A) (50.1 mg, 273 μmol) in ethanol (730 μL) was treated with 1-(pyridin-4-yl)piperazine (51.8 mg, 317 μmol) and N,N-diisopropylethylamine (46.7 mg, 63.10 μL, 361 μmol). The reaction stirred at 100° C. overnight. At this time, the reaction was diluted with methanol and methylene chloride and concentrated in vacuo onto Celite®. Flash chromatography (4 g silica gel column, 10% methanol/methylene chloride) afforded 7-methyl-2-(4-pyridin-4-yl-piperazin-1-yl)-3,7-dihydro-pyrrolo[2,3-d]pyrimidin-4-one (43 mg, 50.8%) as a white solid. $^1$H NMR (300 MHz, DMSO-d$_6$) δ ppm 3.48 (d, J=4.33 Hz, 4H) 3.57 (s, 3H) 3.69 (d, J=6.03 Hz, 4H) 6.25 (d, J=3.39 Hz, 1H) 6.78 (d, J=3.20 Hz, 1H) 6.91 (d, J=6.97 Hz, 2H) 8.19 (d, J=6.40 Hz, 2H) 10.90 (s, 1H). LC-MS calcd. for $C_{16}H_{19}N_6O$ [(M+H)$^+$] 311, obsd. 311.1.

In an analogous manner the following compounds were synthesized following the above procedure:

Example 2

Ethyl 4-(4-(7-methyl-4-oxo-4,7-dihydro-3H-pyrrolo[2,3-d]pyrimidin-2-yl)piperazin-1-yl)benzoate

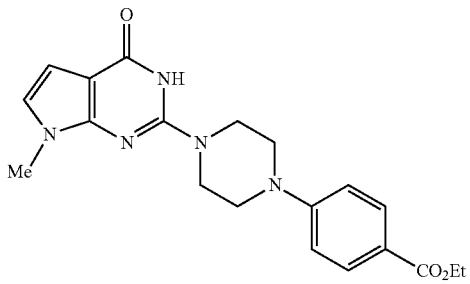 [SMILES: CCOC(=O)c1ccc(N2CCN(c3nc4c(ccn4C)c(=O)[nH]3)CC2)cc1]

From 2-chloro-7-methyl-3,7-dihydro-pyrrolo[2,3-d]pyrimidin-4-one (Intermediate A) and ethyl 4-(piperazin-1-yl)benzoate: 4-[4-(7-methyl-4-oxo-4,7-dihydro-3H-pyrrolo[2,3-d]pyrimidin-2-yl)-piperazin-1-yl]-benzoic acid ethyl ester was obtained as a white solid (173 mg, 55.2%). NMR (300 MHz, DMSO-$d_6$) δ ppm 1.21-1.37 (m, 3H) 3.42 (d, J=5.27 Hz, 4H) 3.57 (s, 3H) 3.71 (br. s., 4H) 4.24 (q, J=7.28 Hz, 2H) 6.25 (d, J=3.39 Hz, 1H) 6.78 (d, J=3.58 Hz, 1H) 7.03 (d, J=9.23 Hz, 2H) 7.80 (d, J=9.04 Hz, 2H) 10.89 (s, 1H). LC-MS calcd. for $C_{20}H_{24}N_5O_3$ [(M+H)$^+$] 382, obsd. 381.96.

Example 3

2-[4-(4-Chloro-phenyl)-piperazin-1-yl]-7-methyl-3,7-dihydro-pyrrolo[2,3-d]pyrimidin-4-one

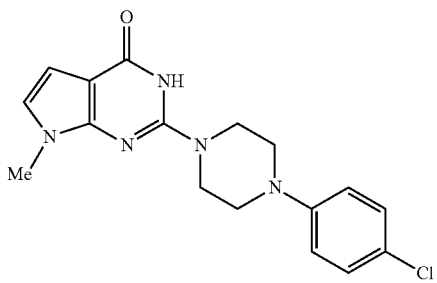 [SMILES: Cn1ccc2c(=O)[nH]c(N3CCN(c4ccc(Cl)cc4)CC3)nc21]

From 2-chloro-7-methyl-3,7-dihydro-pyrrolo[2,3-d]pyrimidin-4-one (Intermediate A) and 1-(4-chlorophenyl)piperazine: 2-[4-(4-chloro-phenyl)-piperazin-1-yl]-7-methyl-3,7-dihydro-pyrrolo[2,3-d]pyrimidin-4-one was obtained as a white solid (34 mg, 35.7%). $^1$H NMR (300 MHz, DMSO-$d_6$) δ ppm 3.22 (d, J=6.03 Hz, 4H) 3.57 (s, 3H) 3.69 (s, 4H) 6.25 (d, J=3.39 Hz, 1H) 6.78 (d, J=3.20 Hz, 1H) 7.00 (d, J=9.04 Hz, 2H) 7.25 (d, J=8.85 Hz, 2H) 10.87 (s, 1H).). LC-MS calcd. for $C_{17}H_{19}ClN_5O$ [(M+H)$^+$] 344, obsd. 343.91.

Example 4

7-Methyl-2-(4-pyridin-2-yl-piperazin-1-yl)-3,7-dihydro-pyrrolo[2,3-d]pyrimidin-4-one

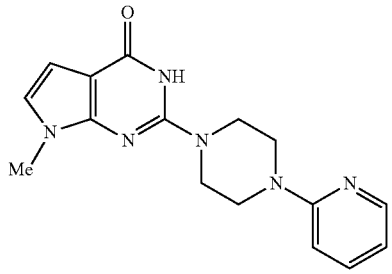 [SMILES: Cn1ccc2c(=O)[nH]c(N3CCN(c4ccccn4)CC3)nc21]

From 2-chloro-7-methyl-3,7-dihydro-pyrrolo[2,3-d]pyrimidin-4-one (Intermediate A) and 1-(pyridin-2-yl)piperazine: 7-methyl-2-(4-pyridin-2-yl-piperazin-1-yl)-3,7-dihydro-pyrrolo[2,3-d]pyrimidin-4-one was obtained as an off-white solid (47 mg, 53.8%). $^1$H NMR (300 MHz, DMSO-$d_6$) δ ppm 3.57 (s, 7H) 3.66 (d, J=5.65 Hz, 4H) 6.25 (d, J=3.39 Hz, 1H) 6.59-6.73 (m, 1H) 6.77 (d, J=3.20 Hz, 1H) 6.89 (d, J=8.48 Hz, 1H) 7.56 (t, J=6.59 Hz, 1H) 8.14 (d, J=3.39 Hz, 1H) 10.85 (s, 1H). LC-MS calcd. for $C_{16}H_{19}N_6O$ [(M+H)$^+$] 311, obsd. 311.1.

Example 5

2-[4-(4-Fluoro-2-methanesulfonyl-phenyl)-piperazin-1-yl]-7-methyl-3,7-dihydro-pyrrolo[2,3-d]pyrimidin-4-one

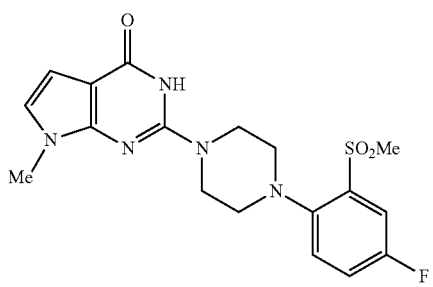 [SMILES: Cn1ccc2c(=O)[nH]c(N3CCN(c4ccc(F)cc4S(C)(=O)=O)CC3)nc21]

From 2-chloro-7-methyl-3,7-dihydro-pyrrolo[2,3-d]pyrimidin-4-one (Intermediate A) and 1-(4-fluoro-2-(methylsulfonyl)phenyl)piperazine: 2-[4-(4-fluoro-2-methanesulfonylphenyl)-piperazin-1-yl]-7-methyl-3,7-dihydro-pyrrolo[2,3-d]pyrimidin-4-one was obtained as a light yellow solid (68.8 mg, 60.4%). $^1$H NMR (300 MHz, DMSO-$d_6$) δ ppm 3.03 (br. s., 4H) 3.46 (s, 3H) 3.57 (s, 3H) 3.61-3.89 (m, 4H) 6.26 (d, J=3.39 Hz, 1H) 6.79 (d, J=3.20 Hz, 1H) 7.52-7.82 (m, 3H) 10.86 (s, 1H). LC-MS calcd. for $C_{18}H_{21}FN_5O_3S$ [(M+H)$^+$] 406, obsd. 406.0.

Example 6

7-Methyl-2-[4-(3-trifluoromethyl-pyridin-2-yl)-piperazin-1-yl]-3,7-dihydro-pyrrolo[2,3-d]pyrimidin-4-one

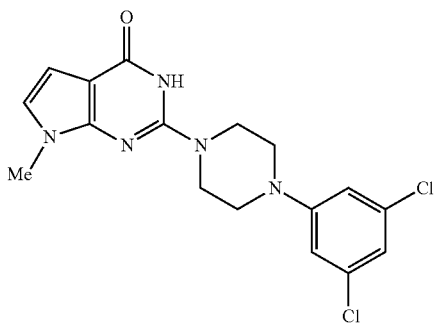 [SMILES: Cn1ccc2c(=O)[nH]c(N3CCN(c4cc(Cl)cc(Cl)c4)CC3)nc21]

From 2-chloro-7-methyl-3,7-dihydro-pyrrolo[2,3-d]pyrimidin-4-one (Intermediate A) and 1-(3-(trifluoromethyl)pyridin-2-yl)piperazine: 7-methyl-2-[4-(3-trifluoromethyl-pyridin-2-yl)-piperazin-1-yl]-3,7-dihydro-pyrrolo[2,3-d]pyrimidin-4-one was obtained as a light yellow solid (42.3 mg, 40.7%). $^1$H NMR (300 MHz, DMSO-$d_6$) δ ppm 3.25 (d, J=6.03 Hz, 4H) 3.55 (s, 3H) 3.68 (br. s., 4H) 6.24 (d, J=3.20 Hz, 1H) 6.77 (d, J=3.58 Hz, 1H) 7.22 (d, J=7.91 Hz, 1H) 8.09 (d, J=7.54 Hz, 1H) 8.53 (s, 1H) 10.83 (s, 1H). LC-MS calcd. for $C_{17}H_{18}F_3N_6O$ [(M+H)$^+$] 379, obsd. 379.0.

Example 7

2-[4-(3,5-Dichloro-phenyl)-piperazin-1-yl]-7-methyl-3,7-dihydro-pyrrolo[2,3-d]pyrimidin-4-one

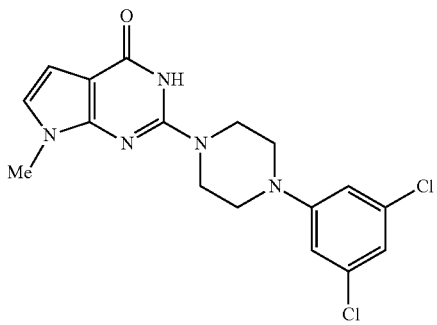 [SMILES: Cn1ccc2c(=O)[nH]c(N3CCN(c4cc(Cl)cc(Cl)c4)CC3)nc21]

From 2-chloro-7-methyl-3,7-dihydro-pyrrolo[2,3-d]pyrimidin-4-one (Intermediate A) and 1-(3,5-dichlorophenyl) piperazine: 2-[4-(3,5-dichloro-phenyl)-piperazin-1-yl]-7-methyl-3,7-dihydro-pyrrolo[2,3-d]pyrimidin-4-one was obtained as a white solid (65.2 mg, 62.9%). $^1$H NMR (300 MHz, DMSO-$d_6$) δ ppm 3.32 (s, 4H) 3.57 (s, 3H) 3.67 (br. s., 4H) 6.25 (d, J=3.39 Hz, 1H) 6.78 (d, J=3.20 Hz, 1H) 6.89 (s, 1H) 7.00 (d, J=1.70 Hz, 2H) 10.89 (s, 1H). LC-MS calcd. for $C_{17}H_{18}Cl_2N_5O$ [(M+H)$^+$] 378, obsd. 378.0.

Example 8

7-Methyl-2-(4-pyrimidin-2-yl-piperazin-1-yl)-3,7-dihydro-pyrrolo[2,3-d]pyrimidin-4-one

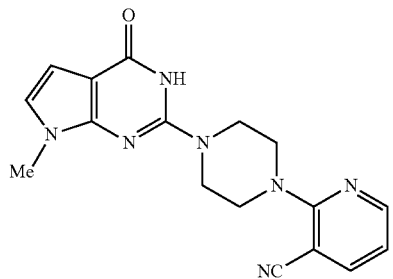 [SMILES: Cn1ccc2c(=O)[nH]c(N3CCN(c4ncccc4C#N)CC3)nc21]

From 2-chloro-7-methyl-3,7-dihydro-pyrrolo[2,3-d]pyrimidin-4-one (Intermediate A) and 2-(piperazin-1-yl)pyrimidine dihydrochloride: 7-methyl-2-(4-pyrimidin-2-yl-piperazin-1-yl)-3,7-dihydro-pyrrolo[2,3-d]pyrimidin-4-one was obtained as an off-white solid (53.3 mg, 63.4%). $^1$H NMR (300 MHz, DMSO-$d_6$) δ ppm 3.57 (s, 3H) 3.65 (d, J=6.40 Hz, 4H) 3.77-3.86 (m, 4H) 6.25 (d, J=3.39 Hz, 1H) 6.67 (t, J=4.71 Hz, 1H) 6.77 (d, J=3.39 Hz, 1H) 8.40 (d, J=4.71 Hz, 2H) 10.83 (s, 1H). LC-MS calcd. for $C_{15}H_{18}N_7O$ [(M+H)$^+$] 312, obsd. 312.0.

Example 9

2-[4-(7-Methyl-4-oxo-4,7-dihydro-3H-pyrrolo[2,3-d]pyrimidin-2-yl)-piperazin-1-yl]-nicotinonitrile

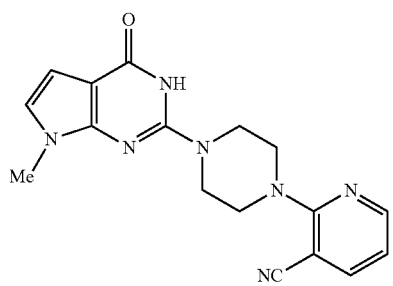 [SMILES: Cn1ccc2c(=O)[nH]c(N3CCN(c4ncccc4C#N)CC3)nc21]

From 2-chloro-7-methyl-3,7-dihydro-pyrrolo[2,3-d]pyrimidin-4-one (Intermediate A) and 2-(piperazin-1-yl)nicotinonitrile: 2-[4-(7-methyl-4-oxo-4,7-dihydro-3H-pyrrolo[2,3-d]pyrimidin-2-yl)-piperazin-1-yl]-nicotinonitrile was obtained as a white solid (55.3 mg, 60.9%). $^1$H NMR (300 MHz, DMSO-$d_6$) δ ppm 3.57 (s, 3H) 3.71 (s, 8H) 6.25 (d, J=3.58 Hz, 1H) 6.78 (d, J=3.39 Hz, 1H) 6.97 (dd, J=7.72, 4.71 Hz, 1H) 8.11 (dd, J=7.72, 1.88 Hz, 1H) 8.44 (dd, J=4.71, 2.07 Hz, 1H) 10.85 (s, 1H). LC-MS calcd. for $C_{17}H_{18}N_7O$ [(M+H)$^+$] 336, obsd. 336.0.

Example 10

4-(7-Methyl-4-oxo-4,7-dihydro-3H-pyrrolo[2,3-d]pyrimidin-2-yl)-3,4,5,6-tetrahydro-2H-[1,2']bipyrazinyl-3'-carbonitrile

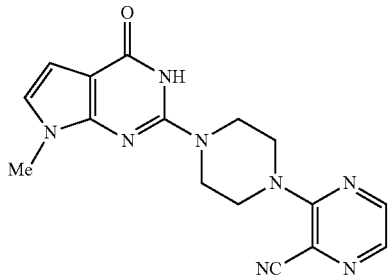 [SMILES: Cn1ccc2c(=O)[nH]c(N3CCN(c4nccnc4C#N)CC3)nc21]

From 2-chloro-7-methyl-3,7-dihydro-pyrrolo[2,3-d]pyrimidin-4-one (Intermediate A) and 3-(piperazin-1-yl)pyrazine-2-carbonitrile: 4-(7-methyl-4-oxo-4,7-dihydro-3H-pyrrolo[2,3-d]pyrimidin-2-yl)-3,4,5,6-tetrahydro-2H-[1,2']bipyrazinyl-3'-carbonitrile was obtained as an off-white solid (60.7 mg, 66.3%). $^1$H NMR (300 MHz, DMSO-$d_6$) δ ppm 3.57 (s, 3H) 3.74 (br. s., 4H) 3.84 (br. s., 4H) 6.26 (d, J=3.39 Hz, 1H) 6.78 (d, J=3.39 Hz, 1H) 8.15 (d, J=2.26 Hz, 1H) 8.48 (d, J=2.26 Hz, 1H) 10.85 (s, 1H). LC-MS calcd. for $C_{16}H_{17}N_8O$ [(M+H)$^+$] 337, obsd. 337.0.

Example 11

7-Methyl-2-(4-methyl-piperazin-1-yl)-3,7-dihydro-pyrrolo[2,3-d]pyrimidin-4-one

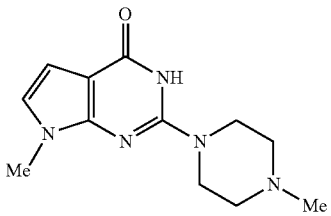

From 2-chloro-7-methyl-3,7-dihydro-pyrrolo[2,3-d]pyrimidin-4-one (Intermediate A) and 1-methylpiperazine: 7-methyl-2-(4-methyl-piperazin-1-yl)-3,7-dihydro-pyrrolo[2,3-d]pyrimidin-4-one was obtained as an off-white solid (29.9 mg, 67.9%). $^1$H NMR (300 MHz, DMSO-$d_6$) δ ppm 2.18 (s, 3H) 2.29-2.40 (m, 4H) 3.46-3.58 (m, 7H) 6.22 (d, J=3.39 Hz, 1H) 6.74 (d, J=3.39 Hz, 1H) 10.71 (s, 1H). LC-MS calcd. for $C_{12}H_{18}N_5O$ [(M+H)$^+$] 248, obsd. 248.2.

Example 12

7-Methyl-2-morpholin-4-yl-3,7-dihydro-pyrrolo[2,3-d]pyrimidin-4-one

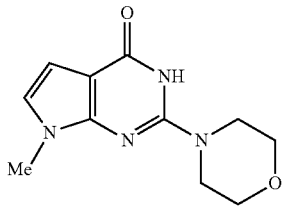 [SMILES: Cn1ccc2c(=O)[nH]c(N3CCOCC3)nc21]

From 2-chloro-7-methyl-3,7-dihydro-pyrrolo[2,3-d]pyrimidin-4-one (Intermediate A) and morpholine: 7-methyl-2-morpholin-4-yl-3,7-dihydro-pyrrolo[2,3-d]pyrimidin-4-one was obtained as an off-white solid (26.2 mg, 73.9%). $^1$H NMR (300 MHz, DMSO-$d_6$) δ ppm 3.53 (d, J=6.78 Hz, 7H) 3.65 (br. s., 4H) 6.25 (br. s., 1H) 6.77 (br. s., 1H) 10.77 (br. s., 1H). LC-MS calcd. for $C_{11}H_{15}N_4O_2$ [(M+H)$^+$] 235, obsd. 235.0.

Example 13

2-(4-Methanesulfonyl-piperazin-1-yl)-7-methyl-3,7-dihydro-pyrrolo[2,3-d]pyrimidin-4-one

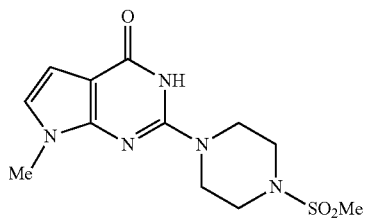 [SMILES: Cn1ccc2c(=O)[nH]c(N3CCN(S(C)(=O)=O)CC3)nc21]

From 2-chloro-7-methyl-3,7-dihydro-pyrrolo[2,3-d]pyrimidin-4-one (Intermediate A) and 1-(methylsulfonyl)piperazine: 2-(4-methanesulfonyl-piperazin-1-yl)-7-methyl-3,7-dihydro-pyrrolo[2,3-d]pyrimidin-4-one was obtained as a white solid (103.7 mg, 60.2%). $^1$H NMR (300 MHz, DMSO-$d_6$) δ ppm 2.91 (s, 3H) 3.13-3.24 (m, 4H) 3.56 (s, 3H) 3.62-3.74 (m, 4H) 6.25 (d, J=3.39 Hz, 1H) 6.79 (d, J=3.39 Hz, 1H) 10.93 (br. s., 1H). LC-MS calcd. for $C_{12}H_{18}N_5O_3S$ [(M+H)$^+$] 312, obsd. 312.0.

Example 14

2-(4-Acetyl-piperazin-1-yl)-7-methyl-3,7-dihydro-pyrrolo[2,3-d]pyrimidin-4-one

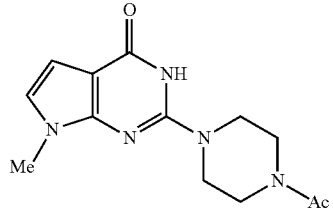

From 2-chloro-7-methyl-3,7-dihydro-pyrrolo[2,3-d]pyrimidin-4-one (Intermediate A) and 1-(piperazin-1-yl)ethanone: 2-(4-acetyl-piperazin-1-yl)-7-methyl-3,7-dihydro-pyrrolo[2,3-d]pyrimidin-4-one was obtained as a white solid (53.7 mg, 71.6%). ¹H NMR (300 MHz, DMSO-d₆) δ ppm 2.03 (s, 3H) 3.44-3.70 (m, 11H) 6.25 (d, J=3.39 Hz, 1H) 6.77 (d, J=3.39 Hz, 1H) 10.84 (br. s., 1H). LC-MS calcd. for $C_{13}H_{18}N_5O_2$ [(M+H)⁺] 276, obsd. 276.1.

Example 15

2-[3-(4-Bromo-phenyl)-3-methyl-azetidin-1-yl]-7-methyl-3,7-dihydro-pyrrolo[2,3-d]pyrimidin-4-one

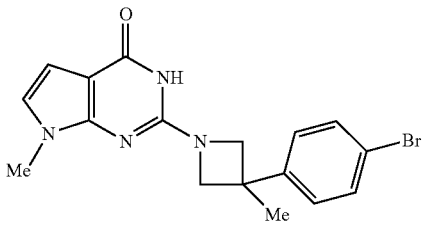 [SMILES: Cn1ccc2c(=O)[nH]c(N3CC(C)(c4ccc(Br)cc4)C3)nc21]

From 2-chloro-7-methyl-3,7-dihydro-pyrrolo[2,3-d]pyrimidin-4-one (Intermediate A) and 3-(4-bromophenyl)-3-methylazetidine (Intermediate I): 2-[3-(4-bromo-phenyl)-3-methyl-azetidin-1-yl]-7-methyl-3,7-dihydro-pyrrolo[2,3-d]pyrimidin-4-one was obtained as an off-white solid (190.5 mg, 70.3%). ¹H NMR (300 MHz, DMSO-d₆) δ ppm 1.59 (s, 3H) 3.53 (s, 3H) 4.02-4.14 (m, 2H) 4.15-4.28 (m, 2H) 6.23 (d, J=3.39 Hz, 1H) 6.73 (d, J=3.58 Hz, 1H) 7.30 (d, J=8.48 Hz, 2H) 7.55 (d, J=8.29 Hz, 2H) 10.91 (s, 1H). LC-MS calcd. for $C_{17}H_{18}BrN_4O$ [(M+H)⁺] 373, obsd. 373.0/375.0.

Example 16

7-Methyl-2-(3-phenyl-pyrrolidin-1-yl)-3,7-dihydro-pyrrolo[2,3-d]pyrimidin-4-one

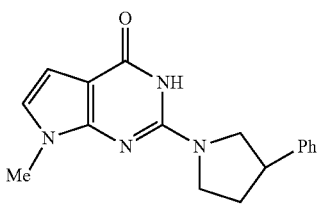 [SMILES: Cn1ccc2c(=O)[nH]c(N3CCC(c4ccccc4)C3)nc21]

From 2-chloro-7-methyl-3,7-dihydro-pyrrolo[2,3-d]pyrimidin-4-one (Intermediate A) and 3-phenylpyrrolidine: 7-methyl-2-(3-phenyl-pyrrolidin-1-yl)-3,7-dihydro-pyrrolo[2,3-d]pyrimidin-4-one was obtained as a white solid (52.8 mg, 32.1%). ¹H NMR (300 MHz, DMSO-d₆) δ ppm 1.92-2.41 (m, 2H) 3.36-3.80 (m, 7H) 3.91-4.05 (m, 1H) 6.22 (d, J=3.39 Hz, 1H) 6.69 (d, J=3.58 Hz, 1H) 7.17-7.39 (m, 5H) 10.42 (s, 1H). LC-MS calcd. for $C_{17}H_{19}N_4O$ [(M+H)⁺] 295, obsd. 295.1.

Example 17

2-[4-(4-Fluoro-phenyl)-piperazin-1-yl]-7-methyl-3,7-dihydro-pyrrolo[2,3-d]pyrimidin-4-one

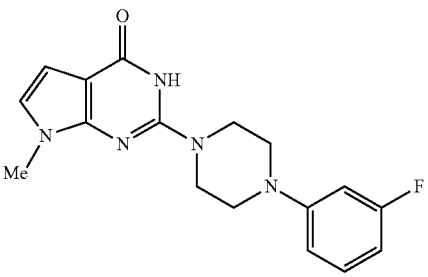 [SMILES: Cn1ccc2c(=O)[nH]c(N3CCN(c4cccc(F)c4)CC3)nc21]

From 2-chloro-7-methyl-3,7-dihydro-pyrrolo[2,3-d]pyrimidin-4-one (Intermediate A) and 1-(4-fluorophenyl)piperazine: 2-[4-(4-fluoro-phenyl)-piperazin-1-yl]-7-methyl-3,7-dihydro-pyrrolo[2,3-d]pyrimidin-4-one was obtained as a white solid (55.6 mg, 60.5%). ¹H NMR (300 MHz, DMSO-d₆) δ ppm 3.08-3.22 (m, 4H) 3.57 (s, 3H) 3.69 (d, J=5.46 Hz, 4H) 6.25 (d, J=3.39 Hz, 1H) 6.78 (d, J=3.20 Hz, 1H) 6.93-7.19 (m, 4H) 10.87 (s, 1H). LC-MS calcd. for $C_{17}H_{19}FN_5O$ [(M+H)⁺] 328, obsd. 328.1.

Example 18

2-[4-(3-Fluoro-phenyl)-piperazin-1-yl]-7-methyl-3,7-dihydro-pyrrolo[2,3-d]pyrimidin-4-one

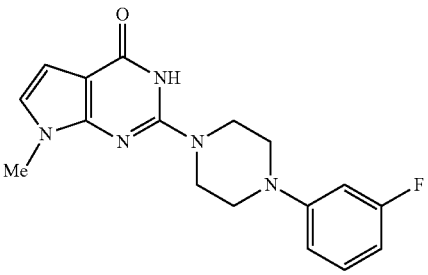 [SMILES: Cn1ccc2c(=O)[nH]c(N3CCN(c4cccc(F)c4)CC3)nc21]

From 2-chloro-7-methyl-3,7-dihydro-pyrrolo[2,3-d]pyrimidin-4-one (Intermediate A) and 1-(3-fluorophenyl)piperazine: 2-[4-(3-fluoro-phenyl)-piperazin-1-yl]-7-methyl-3,7-dihydro-pyrrolo[2,3-d]pyrimidin-4-one was obtained as an off-white solid (34.1 mg, 64.6%). ¹H NMR (300 MHz, DMSO-d₆) δ ppm 3.20-3.30 (m, 4H) 3.57 (s, 3H) 3.70 (d, J=4.90 Hz, 4H) 6.25 (d, J=3.39 Hz, 1H) 6.48-6.66 (m, 1H) 6.70-6.93 (m, 3H) 7.12-7.35 (m, 1H) 10.88 (s, 1H). LC-MS calcd. for $C_{17}H_{19}FN_5O$ [(M+H)⁺] 328, obsd. 327.85.

Example 19

2-[4-(7-Methyl-4-oxo-4,7-dihydro-3H-pyrrolo[2,3-d]pyrimidin-2-yl)-piperazin-1-yl]-benzonitrile

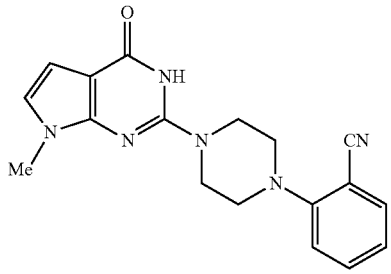

From 2-chloro-7-methyl-3,7-dihydro-pyrrolo[2,3-d]pyrimidin-4-one (Intermediate A) and 2-(piperazin-1-yl)benzonitrile: 2-[4-(7-methyl-4-oxo-4,7-dihydro-3H-pyrrolo[2,3-d]pyrimidin-2-yl)-piperazin-1-yl]-benzonitrile was obtained as a white solid (55.6 mg, 61.3%). $^1$H NMR (300 MHz, DMSO-$d_6$) δ ppm 3.23 (br. s., 4H) 3.58 (s, 3H) 3.75 (br. s., 4H) 6.26 (d, J=3.20 Hz, 1H) 6.78 (d, J=3.58 Hz, 1H) 7.13 (t, J=7.54 Hz, 1H) 7.22 (d, J=8.29 Hz, 1H) 7.62 (t, J=7.25 Hz, 1H) 7.74 (d, J=7.72 Hz, 1H) 10.88 (s, 1H). LC-MS calcd. for $C_{18}H_{19}N_6O$ [(M+H)$^+$] 335, obsd. 335.0.

Example 20

2-[4-(2,4-Difluoro-phenyl)-piperazin-1-yl]-7-methyl-3,7-dihydro-pyrrolo[2,3-d]pyrimidin-4-one

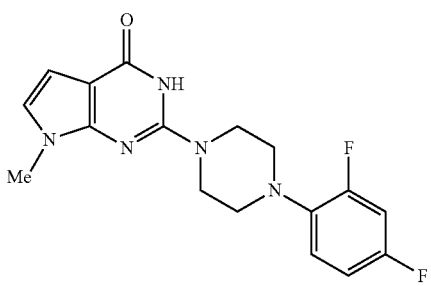 [SMILES: Cn1ccc2c(=O)[nH]c(N3CCN(c4ccc(F)cc4F)CC3)nc21]

From 2-chloro-7-methyl-3,7-dihydro-pyrrolo[2,3-d]pyrimidin-4-one (Intermediate A) and 1-(2,4-difluorophenyl)piperazine: 2-[4-(2,4-difluoro-phenyl)-piperazin-1-yl]-7-methyl-3,7-dihydro-pyrrolo[2,3-d]pyrimidin-4-one was obtained as a white solid (43.4 mg, 46.3%). $^1$H NMR (300 MHz, DMSO-$d_6$) δ ppm 2.94-3.10 (m, 4H) 3.56 (s, 3H) 3.70 (d, J=4.52 Hz, 4H) 6.25 (d, J=3.39 Hz, 1H) 6.78 (d, J=3.39 Hz, 1H) 6.93-7.31 (m, 3H) 10.85 (s, 1H). LC-MS calcd. for $C_{17}H_{18}F_2N_5O$ [(M+H)$^+$] 346, obsd. 346.0.

Example 21

3-[4-(7-Methyl-4-oxo-4,7-dihydro-3H-pyrrolo[2,3-d]pyrimidin-2-yl)-piperazin-1-yl]-benzonitrile

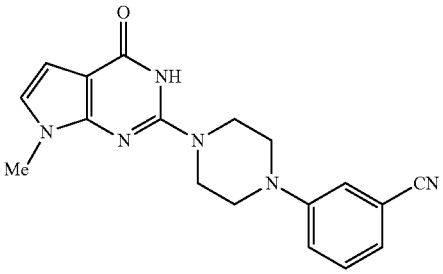 [SMILES: Cn1ccc2c(=O)[nH]c(N3CCN(c4cccc(C#N)c4)CC3)nc21]

From 2-chloro-7-methyl-3,7-dihydro-pyrrolo[2,3-d]pyrimidin-4-one (Intermediate A) and 3-(piperazin-1-yl)benzonitrile: 3-[4-(7-methyl-4-oxo-4,7-dihydro-3H-pyrrolo[2,3-d]pyrimidin-2-yl)-piperazin-1-yl]-benzonitrile was obtained as a white solid (47.4 mg, 51.9%). $^1$H NMR (300 MHz, DMSO-$d_6$) δ ppm 2.50 (br. s, 4H) 2.75 (s, 3H) 2.89 (br. s., 4H) 5.44 (d, J=3.20 Hz, 1H) 5.96 (d, J=3.20 Hz, 1H) 6.37 (d, J=7.16 Hz, 1H) 6.47-6.64 (m, 3H) 10.07 (s, 1H). LC-MS calcd. for $C_{18}H_{19}N_6O$ [(M+H)$^+$] 335, obsd. 335.0.

Example 22

4-[4-(7-Methyl-4-oxo-4,7-dihydro-3H-pyrrolo[2,3-d]pyrimidin-2-yl)-piperazin-1-yl]-benzonitrile

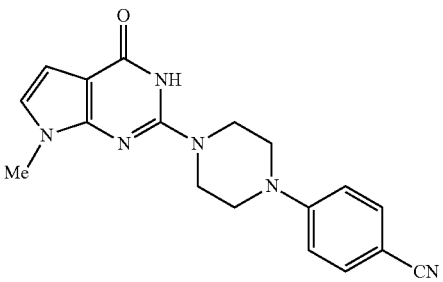 [SMILES: Cn1ccc2c(=O)[nH]c(N3CCN(c4ccc(C#N)cc4)CC3)nc21]

From 2-chloro-7-methyl-3,7-dihydro-pyrrolo[2,3-d]pyrimidin-4-one (Intermediate A) and 4-(piperazin-1-yl)benzonitrile: 4-[4-(7-methyl-4-oxo-4,7-dihydro-3H-pyrrolo[2,3-d]pyrimidin-2-yl)-piperazin-1-yl]-benzonitrile was obtained as a white solid (47.4 mg, 52.1%). NMR (300 MHz, DMSO-$d_6$) δ ppm 3.40-3.51 (m, 4H) 3.57 (s, 3H) 3.70 (d, J=5.46 Hz, 4H) 6.25 (d, J=3.39 Hz, 1H) 6.78 (d, J=3.39 Hz, 1H) 7.07 (d, J=9.04 Hz, 2H) 7.61 (d, J=9.04 Hz, 2H) 10.88 (s, 1H). LC-MS calcd. for $C_{18}H_{19}N_6O$ [(M+H)$^+$] 335, obsd. 335.0.

Example 23

7-Methyl-2-[4-(2-trifluoromethyl-phenyl)-piperazin-1-yl]-3,7-dihydro-pyrrolo[2,3-d]pyrimidin-4-one

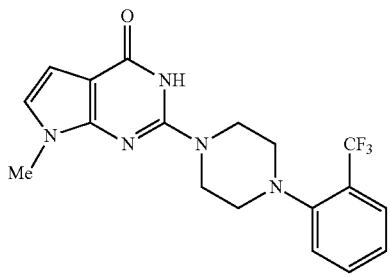 [SMILES: Cn1ccc2c(=O)[nH]c(N3CCN(c4ccccc4C(F)(F)F)CC3)nc21]

From 2-chloro-7-methyl-3,7-dihydro-pyrrolo[2,3-d]pyrimidin-4-one (Intermediate A) and 1-(2-(trifluoromethyl)phenyl)piperazine: 7-methyl-2-[4-(2-trifluoromethyl-phenyl)-piperazin-1-yl]-3,7-dihydro-pyrrolo[2,3-d]pyrimidin-4-one was obtained as a white solid (33.5 mg, 54.5%). $^1$H NMR (300 MHz, DMSO-$d_6$) δ ppm 2.85-2.99 (m, 4H) 3.56 (s, 3H) 3.68 (br. s., 4H) 6.25 (d, J=3.39 Hz, 1H) 6.78 (d, J=3.58 Hz, 1H) 7.37 (t, J=7.16 Hz, 1H) 7.54-7.77 (m, 3H) 10.83 (s, 1H). LC-MS calcd. for $C_{18}H_{19}F_3N_5O$ [(M+H)$^+$] 378, obsd. 378.1.

Example 24

2-[4-(2-Fluoro-4-methanesulfonyl-phenyl)-piperazin-1-yl]-7-methyl-3,7-dihydro-pyrrolo[2,3-d]pyrimidin-4-one

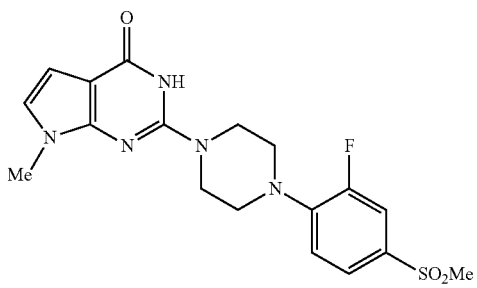 [SMILES: Cn1ccc2c(=O)[nH]c(N3CCN(c4ccc(S(C)(=O)=O)cc4F)CC3)nc21]

From 2-chloro-7-methyl-3,7-dihydro-pyrrolo[2,3-d]pyrimidin-4-one (Intermediate A) and 1-(2-fluoro-4-(methylsulfonyl)phenyl)piperazine: 2-[4-(2-fluoro-4-methanesulfonyl-phenyl)-piperazin-1-yl]-7-methyl-3,7-dihydro-pyrrolo[2,3-d]pyrimidin-4-one was obtained as a white solid (33.4 mg, 49.6%). $^1$H NMR (300 MHz, DMSO-$d_6$) δ ppm 3.20 (s, 3H) 3.27 (br. s., 4H) 3.57 (s, 3H) 3.73 (br. s., 4H) 6.26 (d, J=3.39 Hz, 1H) 6.79 (d, J=3.01 Hz, 1H) 7.27 (t, J=8.67 Hz, 1H) 7.58-7.78 (m, 2H) 10.89 (s, 1H). LC-MS calcd. for $C_{18}H_{21}FN_5O_3S$ [(M+H)$^+$] 406, obsd. 406.0.

Example 25

7-Methyl-2-[4-(4-trifluoromethyl-pyridin-2-yl)-piperazin-1-yl]-3,7-dihydro-pyrrolo[2,3-d]pyrimidin-4-one

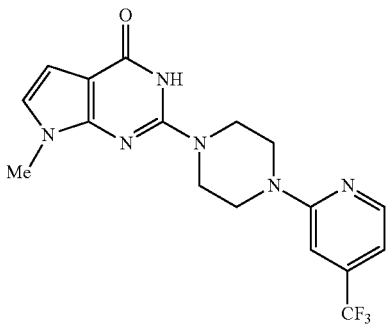 [SMILES: Cn1ccc2c(=O)[nH]c(N3CCN(c4cc(C(F)(F)F)ccn4)CC3)nc21]

From 2-chloro-7-methyl-3,7-dihydro-pyrrolo[2,3-d]pyrimidin-4-one (Intermediate A) and 1-(4-(trifluoromethyl)pyridin-2-yl)piperazine: 7-methyl-2-[4-(4-trifluoromethyl-pyridin-2-yl)-piperazin-1-yl]-3,7-dihydro-pyrrolo[2,3-d]pyrimidin-4-one was obtained as a white solid (26.3 mg, 42.1%). $^1$H NMR (300 MHz, DMSO-$d_6$) δ ppm 3.57 (s, 3H) 3.71 (d, J=7.91 Hz, 8H) 6.25 (d, J=3.39 Hz, 1H) 6.78 (d, J=3.39 Hz, 1H) 7.02 (d, J=9.23 Hz, 1H) 7.83 (d, J=11.68 Hz, 1H) 8.44 (s, 1H) 10.87 (br. s., 1H). LC-MS calcd. for $C_{17}H_{18}F_3N_6O$ [(M+H)$^+$] 379, obsd. 379.1.

Example 26

2-[4-(3,4-Dichloro-phenyl)-piperazin-1-yl]-7-methyl-3,7-dihydro-pyrrolo[2,3-d]pyrimidin-4-one

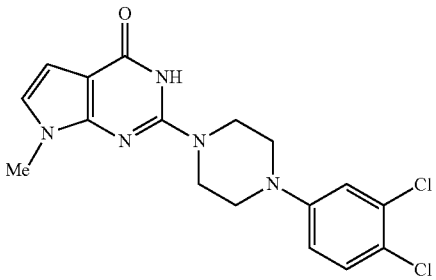 [SMILES: Cn1ccc2c(=O)[nH]c(N3CCN(c4ccc(Cl)c(Cl)c4)CC3)nc21]

From 2-chloro-7-methyl-3,7-dihydro-pyrrolo[2,3-d]pyrimidin-4-one (Intermediate A) and 1-(3,4-dichlorophenyl)piperazine: 2-[4-(3,4-dichloro-phenyl)-piperazin-1-yl]-7-methyl-3,7-dihydro-pyrrolo[2,3-d]pyrimidin-4-one was obtained as a white solid (28.5 mg, 44.9%). $^1$H NMR (300 MHz, DMSO-$d_6$) δ ppm 3.28 (br. s., 4H) 3.57 (s, 3H) 3.68 (br. s., 4H) 6.25 (d, J=3.39 Hz, 1H) 6.78 (d, J=3.39 Hz, 1H) 7.00 (d, J=8.85 Hz, 1H) 7.20 (d, J=2.83 Hz, 1H) 7.42 (d, J=8.85 Hz, 1H) 10.89 (s, 1H). LC-MS calcd. for $C_{17}H_{18}Cl_2N_5O$ [(M+H)$^+$] 378, obsd. 378.0.

Example 27

7-But-3-enyl-2-[4-(2-chloro-phenyl)-piperazin-1-yl]-3,7-dihydro-pyrrolo[2,3-d]pyrimidin-4-one

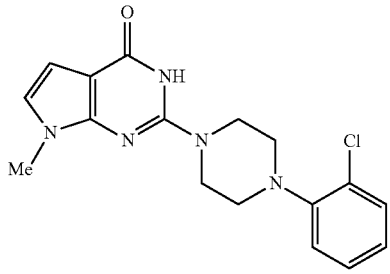 [SMILES: Cn1ccc2c(=O)[nH]c(N3CCN(c4ccccc4Cl)CC3)nc21]

From 7-but-3-enyl-2-chloro-3,7-dihydro-pyrrolo[2,3-d]pyrimidin-4-one (Intermediate B) and 1-(2-chlorophenyl)piperazine dihydrochloride: 7-but-3-enyl-2-[4-(2-chlorophenyl)-piperazin-1-yl]-3,7-dihydro-pyrrolo[2,3-d]pyrimidin-4-one was obtained as a light yellow solid (275.2 mg, 87.0%). $^1$H NMR (300 MHz, DMSO-d$_6$) δ ppm 2.42-2.58 (m, 2H) 3.05 (br. s., 4H) 3.71 (br. s., 4H) 4.05 (t, J=6.97 Hz, 2H) 4.91-5.13 (m, 2H) 5.65-5.89 (m, 1H) 6.24 (d, J=3.39 Hz, 1H) 6.83 (d, J=3.39 Hz, 1H) 7.07 (t, J=6.88 Hz, 1H) 7.15-7.24 (m, 1H) 7.26-7.37 (m, 1H) 7.44 (dd, J=7.82, 1.41 Hz, 1H) 10.85 (s, 1H). LC-MS calcd. for C$_{20}$H$_{23}$ClN$_5$O [(M+H)$^+$] 384, obsd. 383.9.

Example 28

2-[4-(2-Fluoro-phenyl)-piperazin-1-yl]-7-methyl-3,7-dihydro-pyrrolo[2,3-d]pyrimidin-4-one

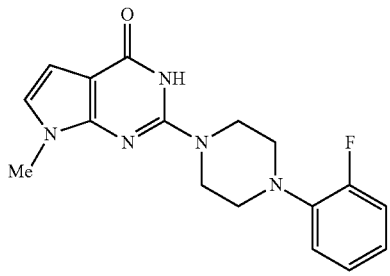

From 2-chloro-7-methyl-3,7-dihydro-pyrrolo[2,3-d]pyrimidin-4-one (Intermediate A) and 1-(2-fluorophenyl)piperazine: 2-[4-(2-fluoro-phenyl)-piperazin-1-yl]-7-methyl-3,7-dihydro-pyrrolo[2,3-d]pyrimidin-4-one was obtained as a white solid (38.4 mg, 67.3%). $^1$H NMR (400 MHz, DMSO-d$_6$) δ ppm 3.01-3.14 (m, 4H) 3.57 (s, 3H) 3.62-3.84 (m, 4H) 6.25 (d, J=3.52 Hz, 1H) 6.78 (d, J=3.52 Hz, 1H) 6.90-7.28 (m, 4H) 10.85 (s, 1H). LC-MS calcd. for C$_{17}$H$_{19}$FN$_5$O [(M+H)$^+$] 328, obsd. 327.9.

Example 29

7-Methyl-2-(4-phenyl-piperazin-1-yl)-3,7-dihydro-pyrrolo[2,3-d]pyrimidin-4-one

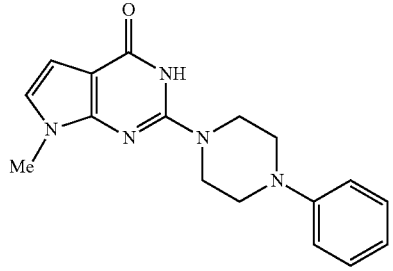 [SMILES: Cn1ccc2c(=O)[nH]c(N3CCN(c4ccccc4)CC3)nc21]

From 2-chloro-7-methyl-3,7-dihydro-pyrrolo[2,3-d]pyrimidin-4-one (Intermediate A) and 1-phenylpiperazine: 7-methyl-2-(4-phenyl-piperazin-1-yl)-3,7-dihydro-pyrrolo[2,3-d]pyrimidin-4-one was obtained as a light yellow solid (30 mg, 59.3%). $^1$H NMR (400 MHz, DMSO-d$_6$) δ ppm 3.13-3.27 (m, 4H) 3.57 (s, 3H) 3.62-3.78 (m, 4H) 6.25 (d, J=3.13 Hz, 1H) 6.68-6.88 (m, 2H) 6.99 (d, J=7.81 Hz, 2H) 7.16-7.31 (m, 2H) 10.87 (s, 1H). LC-MS calcd. for C$_{17}$H$_{20}$N$_5$O [(M+H)$^+$] 310, obsd. 310.1.

Example 30

2-[4-(2-Chloro-phenyl)-piperazin-1-yl]-7-methyl-3,7-dihydro-pyrrolo[2,3-d]pyrimidin-4-one

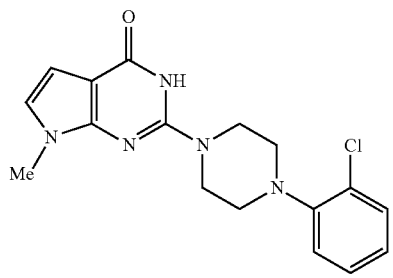 [SMILES: Cn1ccc2c(=O)[nH]c(N3CCN(c4ccccc4Cl)CC3)nc21]

From 2-chloro-7-methyl-3,7-dihydro-pyrrolo[2,3-d]pyrimidin-4-one (Intermediate A) and 1-(2-chlorophenyl)piperazine dihydrochloride salt: 2-[4-(2-chloro-phenyl)-piperazin-1-yl]-7-methyl-3,7-dihydro-pyrrolo[2,3-d]pyrimidin-4-one was obtained as a white solid (13.3 mg, 23.7%). $^1$H NMR (400 MHz, DMSO-d$_6$) δ ppm 2.96-3.13 (m, 4H) 3.57 (s, 3H) 3.65-3.78 (m, 4H) 6.25 (d, J=3.52 Hz, 1H) 6.78 (d, J=3.52 Hz, 1H) 7.07 (td, J=7.62, 1.56 Hz, 1H) 7.20 (dd, J=7.81, 1.56 Hz, 1H) 7.26-7.36 (m, 1H) 7.44 (dd, J=8.01, 1.37 Hz, 1H) 10.85 (s, 1H). LC-MS calcd. for C$_{17}$H$_{19}$ClN$_5$O [(M+H)$^+$] 344, obsd. 344.1.

Example 31

7-Methyl-2-(2,3,5,6-tetrahydro-[1,2']bipyrazinyl-4-yl)-3,7-dihydro-pyrrolo[2,3-d]pyrimidin-4-one

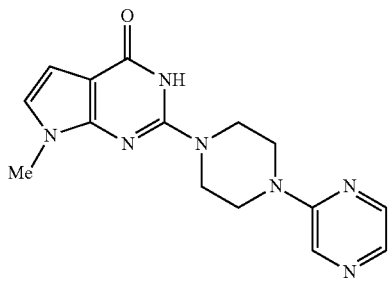 [SMILES: Cn1ccc2c(=O)[nH]c(N3CCN(c4cnccn4)CC3)nc21]

From 2-chloro-7-methyl-3,7-dihydro-pyrrolo[2,3-d]pyrimidin-4-one (Intermediate A) and 1-(2-pyrazinyl)-piperazine: 7-methyl-2-(2,3,5,6-tetrahydro-[1,2']bipyrazinyl-4-yl)-3,7-dihydro-pyrrolo[2,3-d]pyrimidin-4-one was obtained as an off-white solid (37 mg, 72.7%). $^1$H NMR (300 MHz, DMSO-$d_6$) δ ppm 3.57 (s, 3H) 3.68 (br. s., 8H) 6.25 (d, J=3.39 Hz, 1H) 6.78 (d, J=3.20 Hz, 1H) 7.87 (d, J=2.64 Hz, 1H) 8.11 (s, 1H) 8.38 (d, J=1.32 Hz, 1H) 10.88 (s, 1H). LC-MS calcd. for $C_{15}H_{18}N_7O$ [(M+H)$^+$] 312, obsd. 312.1.

Example 32

6-[4-(7-Methyl-4-oxo-4,7-dihydro-3H-pyrrolo[2,3-d]pyrimidin-2-yl)-piperazin-1-yl]-nicotinonitrile

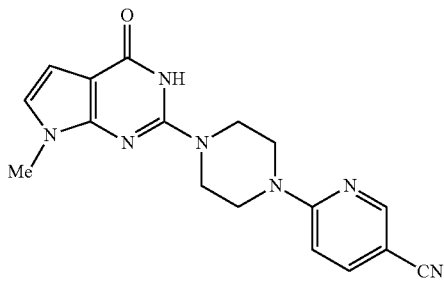 [SMILES: Cn1ccc2c(=O)[nH]c(N3CCN(c4ccc(C#N)cn4)CC3)nc21]

From 2-chloro-7-methyl-3,7-dihydro-pyrrolo[2,3-d]pyrimidin-4-one (Intermediate A) and 6-piperazinonicotinonitrile: 6-[4-(7-methyl-4-oxo-4,7-dihydro-3H-pyrrolo[2,3-d]pyrimidin-2-yl)-piperazin-1-yl]-nicotinonitrile was obtained as a white solid (36.2 mg, 66.1%). $^1$H NMR (300 MHz, DMSO-$d_6$) δ ppm 3.57 (s, 3H) 3.67 (br. s., 4H) 3.75 (br. s., 4H) 6.25 (d, J=3.39 Hz, 1H) 6.78 (d, J=3.20 Hz, 1H) 6.99 (d, J=8.67 Hz, 1H) 7.77-7.98 (m, 1H) 8.51 (s, 1H) 10.86 (s, 1H). LC-MS calcd. for $C_{17}H_{18}N_7O$ [(M+H)$^+$] 336, obsd. 336.1.

Example 33

2-[(1S,4S)-5-(3-Fluoro-phenyl)-2,5-diaza-bicyclo[2.2.1]hept-2-yl]-7-methyl-3,7-dihydro-pyrrolo[2,3-d]pyrimidin-4-one

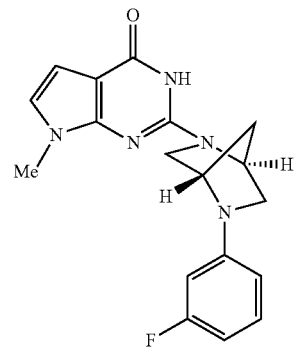 [SMILES: Cn1ccc2c(=O)[nH]c(N3C[C@@H]4C[C@H]3CN4c3cccc(F)c3)nc21]

From 2-chloro-7-methyl-3,7-dihydro-pyrrolo[2,3-d]pyrimidin-4-one (Intermediate A) and (1S,4S)-2-(3-fluorophenyl)-2,5-diazabicyclo[2.2.1]heptane: 2-[(1S,4S)-5-(3-fluoro-phenyl)-2,5-diaza-bicyclo[2.2.1]hept-2-yl]-7-methyl-3,7-dihydro-pyrrolo[2,3-d]pyrimidin-4-one was obtained as an off-white solid (29.3 mg, 52.8%). $^1$H NMR (400 MHz, DMSO-$d_6$) δ ppm 1.93-2.09 (m, 2H) 3.08 (d, J=9.37 Hz, 1H) 3.40-3.48 (m, 1H) 3.50 (s, 3H) 3.52-3.62 (m, 2H) 4.65 (s, 1H) 5.02 (s, 1H) 6.19 (d, J=3.52 Hz, 1H) 6.26-6.55 (m, 3H) 6.68 (d, J=3.52 Hz, 1H) 7.13 (q, J=7.94 Hz, 1H) 10.62 (br. s., 1H). LC-MS calcd. for $C_{18}H_{19}FN_5O$ [(M+H)$^+$] 340, obsd. 340.1.

Example 34

2-[4-(3,5-Dichloro-pyridin-4-yl)-piperazin-1-yl]-7-methyl-3,7-dihydro-pyrrolo[2,3-d]pyrimidin-4-one

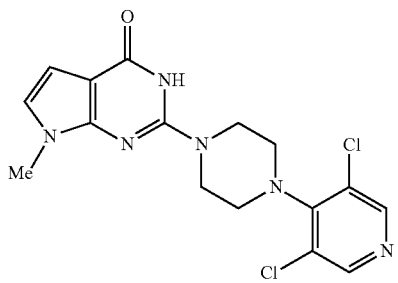 [SMILES: Cn1ccc2c(=O)[nH]c(N3CCN(c4c(Cl)cncc4Cl)CC3)nc21]

From 2-chloro-7-methyl-3,7-dihydro-pyrrolo[2,3-d]pyrimidin-4-one (Intermediate A) and 1-(3,5-dichloro-4-pyridyl)piperazine: 2-[4-(3,5-dichloro-pyridin-4-yl)-piperazin-1-yl]-7-methyl-3,7-dihydro-pyrrolo[2,3-d]pyrimidin-4-one was obtained as an off-white solid (40.8 mg, 62.1%). $^1$H NMR (400 MHz, DMSO-$d_6$) δ ppm 3.34-3.41 (m, 4H) 3.57 (s, 3H) 3.71 (br. s., 4H) 6.27 (d, J=3.52 Hz, 1H) 6.79 (d, J=3.52 Hz, 1H) 8.49 (s, 2H) 10.90 (s, 1H). LC-MS calcd. for $C_{16}H_{17}Cl_2N_6O$ [(M+H)$^+$] 379, obsd. 379.0.

Example 35

6-[4-(2-Fluoro-phenyl)-piperazin-1-yl]-1-methyl-1,5-dihydro-pyrrolo[3,2-c]pyridin-4-one

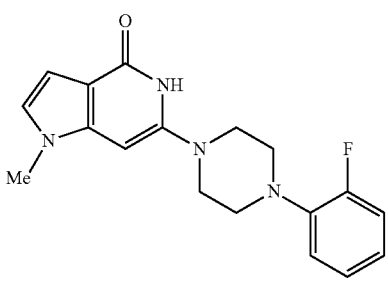 [SMILES: Cn1ccc2c(=O)[nH]c(N3CCN(c4ccccc4F)CC3)cc21]

A mixture of 6-chloro-1-methyl-1,5-dihydro-pyrrolo[3,2-c]pyridine-4-one (Intermediate G) (17 mg, 0.09 mmol) and 1-(2-fluorophenyl)piperazine (140 mg, 0.77 mmol) was heated at 140° C. in a sealed tube overnight. Flash chromatography (20/1 methylene chloride/methanol) afforded 6-[4-(2-fluoro-phenyl)-piperazin-1-yl]-1-methyl-1,5-dihydro-pyrrolo[3,2-c]pyridin-4-one (20 mg, 65.8%) as a white solid. $^1$H NMR (400 MHz, DMSO-$d_6$) δ ppm 3.1 (d, J=4.77 Hz, 4H) 3.2-3.3 (m, 4H) 3.6 (s, 3H) 5.8 (s, 1H) 6.3 (d, J=3.01 Hz, 1H) 6.9 (d, J=3.01 Hz, 1H) 7.0-7.0 (m, 1H) 7.1-7.2 (m, 3H) 10.6 (s, 1H). LC-MS calcd. for $C_{18}H_{20}FN_4O$ [(M+H)$^+$] 327, obsd. 327.1.

Example 36

1-Ethyl-6-[4-(2-fluoro-phenyl)-piperazin-1-yl]-1,5-dihydro-pyrrolo[3,2-c]pyridin-4-one

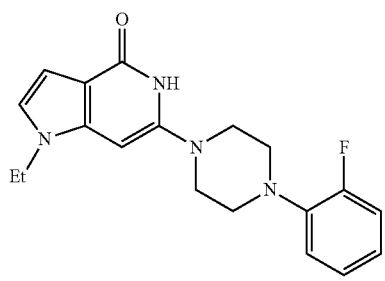 [SMILES: CCn1ccc2c(=O)[nH]c(N3CCN(c4ccccc4F)CC3)cc21]

A mixture of 6-chloro-1-ethyl-1,5-dihydro-pyrrolo[3,2-c]pyridine-4-one (Intermediate G) (16 mg, 0.081 mmol) and 1-(2-fluorophenyl)piperazine (160 mg, 0.888 mmol) was heated at 140° C. in a sealed tube for 5 h. Flash chromatography (20/1 methylene chloride/methanol) afforded 1-ethyl-6-[4-(2-fluoro-phenyl)-piperazin-1-yl]-1,5-dihydro-pyrrolo[3,2-c]pyridin-4-one (18 mg, 65%) as a white solid. $^1$H NMR (400 MHz, DMSO-$d_6$) δ ppm 1.3 (t, J=7.28 Hz, 3H) 3.1 (d, J=4.77 Hz, 4H) 3.2 (d, J=4.77 Hz, 4H) 4.0 (q, J=7.19 Hz, 2H) 5.8 (s, 1H) 6.3 (d, J=3.01 Hz, 1H) 6.9 (d, J=3.01 Hz, 1H) 7.1-7.2 (m, 3H) 10.6 (s, 1H). LC-MS calcd. for $C_{19}H_{22}FN_4O$ [(M+H)$^+$] 341, obsd. 341.1.

Example 37

2-(4-Trifluoromethyl-phenyl)-3,7-dihydro-pyrrolo[2,3-d]pyrimidin-4-one

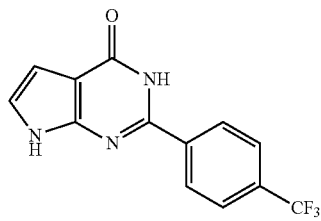 [SMILES: O=c1[nH]c(-c2ccc(C(F)(F)F)cc2)nc2[nH]ccc12]

A microwave reaction vial was charged with 2-chloro-3,7-dihydro-pyrrolo[2,3-d]pyrimidin-4-one (Intermediate F) (80 mg, 0.32 mmol), 4,4,5,5-tetramethyl-2-(4-(trifluoromethyl)phenyl)-1,3,2-dioxaborolane (154 mg, 0.56 mmol), tetrakis(triphenylphosphine)palladium(0) (27.3 mg, 0.024 mmol) and a 2M aqueous sodium carbonate solution (0.75 mL) in ethanol (3 mL). The vial was sealed and the reaction was heated in the microwave at 150° C. for 10 min. At this time, the resulting mixture was filtered through a pad of Celite® and concentrated in vacuo. Flash chromatography (30/1 methylene chloride/methanol) afforded 2-(4-trifluoromethyl-phenyl)-3,7-dihydro-pyrrolo[2,3-d]pyrimidin-4-one (5.0 mg, 3.8%) as a white solid. $^1$HNMR (400 MHz, DMSO-$d_6$) δ ppm 6.50-6.59 (m, 1H) 7.9 (d, 2H) 7.11-7.19 (m, 1H) 8.3 (d, 2H) 12.1 (s, 1H) 12.3 (s, 1H). LC-MS calcd. for $C_{13}H_9F_3N_3O$ [(M+H)$^+$] 280, obsd. 279.9.

Example 38

7-Methyl-2-(4-trifluoromethyl-phenyl)-3,7-dihydro-pyrrolo[2,3-d]pyrimidin-4-one

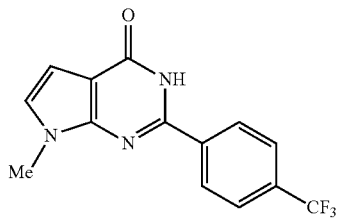

A microwave reaction vial was charged with 2-chloro-7-methyl-3,7-dihydro-pyrrolo[2,3-d]pyrimidin-4-one (Intermediate A) (60 mg, 0.32 mmol), 4,4,5,5-tetramethyl-2-(4-(trifluoromethyl)phenyl)-1,3,2-dioxaborolane (107 mg, 0.39 mmol), tetrakis(triphenylphosphine)palladium(0) (18.9 mg, 0.01 mmol), and a 2M aqueous sodium carbonate solution (0.49 mL) in ethanol (2 mL). The vial was capped and heated in the microwave at 150° C. for 8 min. The resulting mixture was filtered through a pad of Celite® and concentrated in vacuo. Flash chromatography (30/1 methylene chloride/methanol) afforded 7-methyl-2-(4-trifluoromethyl-phenyl)-3,7-dihydro-pyrrolo[2,3,-d]pyrimidin-4-one (29 mg, 30%) as a white solid. LC-MS calcd. for $C_{14}H_{11}F_3N_3O$ [(M+H)$^+$] 294, obsd. 294.0.

In an analogous manner the following compounds were synthesized following the above procedure:

Example 39

2-(4-Methoxy-phenyl)-7-methyl-3,7-dihydro-pyrrolo[2,3-d]pyrimidin-4-one

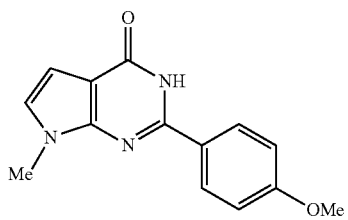 [SMILES: COc1ccc(-c2nc3c(ccn3C)c(=O)[nH]2)cc1]

From 2-chloro-7-methyl-3,7-dihydro-pyrrolo[2,3-d]pyrimidin-4-one (Intermediate A) and 4-methoxyphenylboronic acid: 2-(4-methoxy-phenyl)-7-methyl-3,7-dihydro-pyrrolo[2,3-d]pyrimidin-4-one was obtained as a white solid. LC-MS calcd. for $C_{14}H_{14}N_3O_2$ [(M+H)$^+$] 256, obsd. 256.0.

Example 40

2-(6-Ethoxy-pyridin-3-yl)-7-methyl-3,7-dihydro-pyrrolo[2,3-d]pyrimidin-4-one

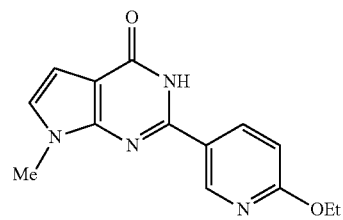 [SMILES: CCOc1ccc(-c2nc3c(ccn3C)c(=O)[nH]2)cn1]

From 2-chloro-7-methyl-3,7-dihydro-pyrrolo[2,3-d]pyrimidin-4-one (Intermediate A) and 2-ethoxy-5-(4,4,5,5-tetramethyl-1,3,2-dioxaborolan-2-yl)pyridine: 2-(6-ethoxy-pyridin-3-yl)-7-methyl-3,7-dihydro-pyrrolo[2,3-d]pyrimidin-4-one was obtained as a white solid (10 mg, 13.6%). $^1$H NMR (400 MHz, DMSO-d$_6$) δ ppm 1.3 (t, J=7.15 Hz, 3H) 3.8 (s, 3H) 4.4 (q, J=7.03 Hz, 2H) 6.5 (d, J=3.51 Hz, 1H) 6.9 (d, J=8.78 Hz, 1H) 7.1 (d, J=3.26 Hz, 1H) 8.4 (dd, J=8.78, 2.51 Hz, 1H) 8.9 (d, J=2.51 Hz, 1H) 12.1 (br. s., 1H). LC-MS calcd. for $C_{14}H_{15}N_4O_2$ [(M+H)$^+$] 271, obsd. 271.0.

Example 41

7-Methyl-2-pyridin-3-yl-3,7-dihydro-pyrrolo[2,3-d]pyrimidin-4-one

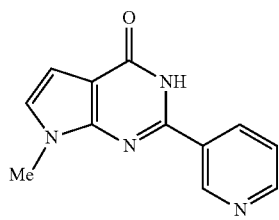 [SMILES: Cn1ccc2c(=O)[nH]c(-c3cccnc3)nc21]

From 2-chloro-7-methyl-3,7-dihydro-pyrrolo[2,3-d]pyrimidin-4-one (Intermediate A) and 3-(4,4,5,5-tetramethyl-1,3,2-dioxaborolan-2-yl)pyridine: 7-methyl-2-pyridin-3-yl-3,7-dihydro-pyrrolo[2,3-d]pyrimidin-4-one was obtained as a white solid (57 mg, 80.2%). $^1$HNMR (400 MHz, DMSO-d$_6$) δ ppm 3.79 (s, 3H) 6.52 (d, J=3.26 Hz, 1H) 7.18 (d, J=3.26 Hz, 1H) 7.56 (dd, J=8.03, 4.77 Hz, 1H) 8.47 (dt, J=8.16, 1.82 Hz, 1H) 8.71 (dd, J=4.77, 1.51 Hz, 1H) 9.29 (d, J=1.76 Hz, 1H) 12.31 (br. s., 1H). LC-MS calcd. for $C_{12}H_{11}N_4O$ [(M+H)$^+$] 227, obsd. 227.0.

Example 42

7-Methyl-2-(6-methyl-pyridin-3-yl)-3,7-dihydro-pyrrolo[2,3-d]pyrimidin-4-one

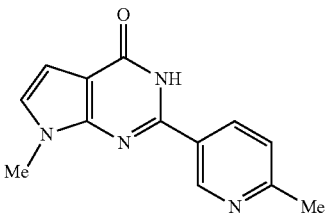 [SMILES: Cc1ccc(-c2nc3c(ccn3C)c(=O)[nH]2)cn1]

From 2-chloro-7-methyl-3,7-dihydro-pyrrolo[2,3-d]pyrimidin-4-one (Intermediate A) and 2-methyl-5-(4,4,5,5-tetramethyl-1,3,2-dioxaborolan-2-yl)pyridine: 7-methyl-2-(6-methyl-pyridin-3-yl)-3,7-dihydro-pyrrolo[2,3-d]pyrimidin-4-one was obtained as a white solid (45 mg, 59.6%). $^1$H NMR (400 MHz, DMSO-d$_6$) δ ppm 2.5 (s, 3H) 3.8 (s, 3H) 6.5 (d, J=3.26 Hz, 1H) 7.2 (d, J=3.26 Hz, 1H) 7.4 (d, J=8.28 Hz, 1H) 8.4 (dd, J=8.16, 2.38 Hz, 1H) 9.2 (d, J=2.01 Hz, 1H) 12.2 (br. s., 1H). LC-MS calcd. for $C_{13}H_{13}N_4O$ [(M+H)$^+$] 241, obsd. 241.0.

Example 43

4-(7-Methyl-4-oxo-4,7-dihydro-3H-pyrrolo[2,3-d]pyrimidin-2-yl)-benzonitrile

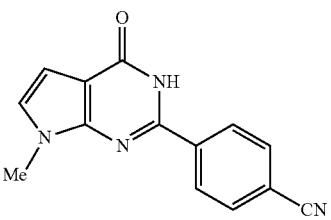 [SMILES: Cn1ccc2c(=O)[nH]c(-c3ccc(C#N)cc3)nc21]

From 2-chloro-7-methyl-3,7-dihydro-pyrrolo[2,3-d]pyrimidin-4-one (Intermediate A) and 4-cyanophenylboronic acid: 4-(7-methyl-4-oxo-4,7-dihydro-3H-pyrrolo[2,3-d]pyrimidin-2-yl)-benzonitrile was obtained as a white solid. LC-MS calcd. for $C_{14}H_{11}N_4O$ [(M+H)$^+$] 251, obsd. 250.9.

Example 44

7-Methyl-2-(6-trifluoromethyl-pyridin-3-yl)-3,7-dihydro-pyrrolo[2,3-d]pyrimidin-4-one

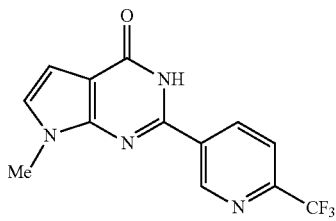 [SMILES: Cn1ccc2c(=O)[nH]c(-c3ccc(C(F)(F)F)nc3)nc21]

A high pressure microwave reaction vial was charged with 2-chloro-7-methyl-3,7-dihydro-pyrrolo[2,3-d]pyrimidin-4-one (Intermediate A) (55 mg, 0.3 mmol), 6-(trifluoromethyl)pyridin-3-ylboronic acid (68.6 mg, 0.36 mmol), [1,1'-bis(diphenylphosphino)ferrocene]dichloropalladium(II) complex with dichloromethane (21.9 mg, 0.03 mmol), a 2M aqueous sodium carbonate solution (0.45 mL, 0.9 mmol), and ethanol (2 mL). The vessel was sealed, degassed and flushed with nitrogen three times. The reaction was then heated at 150° C. for 10 min in a Biotage microwave reactor. At this time, the resulting black mixture was concentrated in vacuo. The residue was treated with ethyl acetate (20 mL), stirred and filtered. The filtrate was concentrated in vacuo. Reverse phase chromatography (10-100% acetonitrile/water) and lyophilization afforded 7-methyl-2-(6-trifluoromethyl-pyridin-3-yl)-3,7-dihydro-pyrrolo[2,3-d]pyrimidin-4-one (6 mg, 6.81%) as a white solid. LC-MS calcd. for $C_{13}H_{10}F_3N_4O$ [(M+H)$^+$] 295, obsd. 294.8.

Example 45

1-Methyl-6-(4-trifluoromethyl-phenyl)-1,5-dihydro-pyrrolo[3,2-c]pyridin-4-one

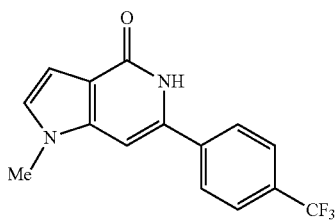 [SMILES: Cn1ccc2c(=O)[nH]c(-c3ccc(C(F)(F)F)cc3)cc21]

A microwave reaction vial was charged with 6-chloro-1-methyl-1,5-dihydro-pyrrolo[3,2-c]pyridine-4-one (Intermediate G) (16 mg, 0.08 mmol), 4-(trifluoromethyl)phenylboronic acid (20 mg, 0.10 mmol), tetrakis(triphenylphosphine)palladium(0) (5.06 mg, 0.004 mmol), and 2M aqueous sodium carbonate solution (0.13 mL) in ethanol (2 mL). The vial was sealed and then heated in a microwave at 140° C. for 10 min. At this time, the resulting mixture was filtered through a pad of Celite® and concentrated in vacuo. Flash chromatography (20/1 methylene chloride/methanol) afforded 1-methyl-6-(4-trifluoromethyl-phenyl)-1,5-dihydro-pyrrolo[3,2-c]pyridin-4-one (25.6 mg, 39.1%) as a white solid. $^1$H NMR (400 MHz, DMSO-d$_6$) δ ppm 3.8 (s, 3H) 6.5 (d, J=3.01 Hz, 1H) 7.0 (s, 1H) 7.1 (d, J=3.01 Hz, 1H) 7.8 (d, J=8.28 Hz, 2H) 8.0 (d, J=8.28 Hz, 2H) 11.1 (br. s., 1H). LC-MS calcd. for $C_{15}H_{12}F_3N_2O$ [(M+H)$^+$] 293, obsd. 293.0.

In an analogous manner the following compounds were synthesized following the above procedure:

Example 46

1-Ethyl-6-(4-trifluoromethyl-phenyl)-1,5-dihydro-pyrrolo[3,2-c]pyridin-4-one

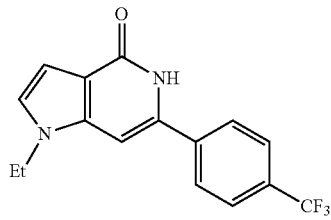 [SMILES: CCn1ccc2c(=O)[nH]c(-c3ccc(C(F)(F)F)cc3)cc21]

From 6-chloro-1-ethyl-1,5-dihydro-pyrrolo[3,2-c]pyridine-4-one (40 mg, 0.203 mmol) (Intermediate H) and 4-(trifluoromethyl)phenylboronic acid (46.4 mg, 0.244 mmol): 1-ethyl-6-(4-trifluoromethyl-phenyl)-1,5-dihydro-pyrrolo[3,2-c]pyridin-4-one was obtained as a white solid (49 mg, 78.6%). $^1$H NMR (400 MHz, DMSO-d$_6$) δ ppm 1.35 (t, J=7.15 Hz, 3H) 4.20 (q, J=7.28 Hz, 2H) 6.55 (d, J=3.01 Hz, 1H) 7.06 (s, 1H) 7.22 (d, J=3.01 Hz, 1H) 7.81 (d, J=8.53 Hz, 2H) 8.00 (d, J=8.28 Hz, 2H) 11.14 (s, 1H). LC-MS calcd. for $C_{16}H_{13}F_3N_2O$ [(M)$^+$] 306, obsd. 306.8.

Example 47

1-Methyl-6-(1-methyl-1H-pyrazol-4-yl)-1,5-dihydro-pyrrolo[3,2-c]pyridin-4-one

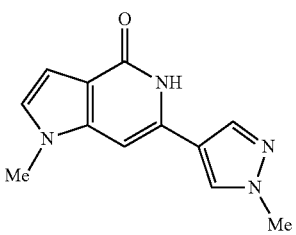 [SMILES: Cn1cc(-c2cc3c(ccn3C)c(=O)[nH]2)cn1]

From 6-chloro-1-methyl-1,5-dihydro-pyrrolo[3,2-c]pyridine-4-one (Intermediate G) and 1-methyl-4-(4,4,5,5-tetramethyl-1,3,2-dioxaborolan-2-yl)-1H-pyrazole: 2-(4-methoxyphenyl)-7-methyl-3,7-dihydro-pyrrolo[2,3-d]pyrimidin-4-one was obtained as a white solid (21 mg, 56%). $^1$H NMR (400 MHz, DMSO-d$_6$) δ ppm 3.72 (s, 3H) 3.86 (s, 3H) 6.46 (dd, J=3.01, 0.75 Hz, 1H) 6.83 (s, 1H) 7.03 (d, J=3.01 Hz, 1H) 8.04 (d, J=0.75 Hz, 1H) 8.30 (s, 1H) 10.86 (s, 1H). LC-MS calcd. for $C_{12}H_{13}N_4O$ [(M+H)$^+$] 229, obsd. 229.0.

Example 48

2-[4-(4-Fluoro-phenyl)-piperidin-1-yl]-7-methyl-3,7-dihydro-pyrrolo[2,3-d]pyrimidin-4-one

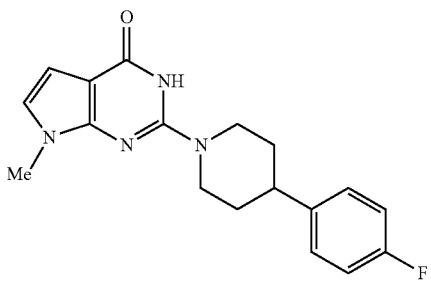 [SMILES: Cn1ccc2c(=O)[nH]c(N3CCC(c4ccc(F)cc4)CC3)nc21]

A microwave reaction vial was charged with 2-chloro-7-methyl-3,7-dihydro-pyrrolo[2,3-d]pyrimidin-4-one (Intermediate A) (25 mg, 0.13 mmol), 4-(4-fluorophenyl)piperidine hydrochloride (35.2 mg, 0.16 mmol), and N,N-diisopropylethylamine (52.8 mg, 0.41 mmol) in ethanol (1.5 mL). The vial was sealed and then heated in the microwave at 140° C. for 15 min. At this time, the resulting mixture was concentrated in vacuo. Flash chromatography (20/1 methylene chloride/methanol) afforded 2-[4-(4-fluoro-phenyl)-piperidin-1-yl]-7-methyl-3,7-dihydro-pyrrolo[2,3-d]pyrimidin-4-one (44.4 mg, 36%) as a white solid. $^1$H NMR (400 MHz, DMSO-$d_6$) δ ppm 1.5-1.7 (m, 2H) 1.8 (d, J=11.55 Hz, 2H) 2.8 (br. s., 1H) 2.9 (t, J=12.05 Hz, 2H) 3.5 (s, 3H) 4.5 (d, J=13.05 Hz, 2H) 6.2 (d, J=3.51 Hz, 1H) 6.7 (d, J=3.26 Hz, 1H) 7.1 (t, J=8.78 Hz, 2H) 7.3 (dd, J=8.53, 5.52 Hz, 2H) 10.7 (s, 1H). LC-MS calcd. for $C_{18}H_{20}FN_4O$ [(M+H)$^+$] 327, obsd. 327.0.

Example 49

7-But-3-enyl-2-(4-trifluoromethyl-phenyl)-3,7-dihydro-pyrrolo[2,3-d]pyrimidin-4-one

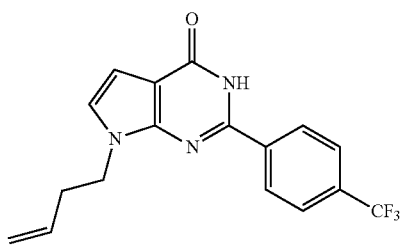 [SMILES: C=CCCn1ccc2c(=O)[nH]c(-c3ccc(C(F)(F)F)cc3)nc21]

A microwave reaction vial was charged with 7-but-3-enyl-2-chloro-3,7-dihydro-pyrrolo[2,3-d]pyrimidin-4-one (Intermediate B) (96.1 mg, 430 µmol,), ethanol (1.6 mL), a 2M aqueous sodium carbonate solution (645 µL, 1.29 mmol), 4-(trifluoromethyl)phenylboronic acid (98.2 mg, 517 µmol), and tetrakis(triphenylphosphine)palladium(0) (27.2 mg, 23.5 µmol). The reaction was heated in a microwave at 150° C. for 68 min. The reaction was filtered through a pad of Celite®, rinsing with ethanol. The filtrate was concentrated in vacuo onto Celite®. Flash chromatography (12 g silica gel column, 10-30% ethyl acetate/hexanes) afforded 7-but-3-enyl-2-(4-trifluoromethyl-phenyl)-3,7-dihydro-pyrrolo[2,3-d]pyrimidin-4-one (98.9 mg, 69.1%) as an off-white solid. $^1$H NMR (300 MHz, DMSO-$d_6$) δ ppm 2.59 (q, J=6.66 Hz, 2H) 4.29 (t, J=6.88 Hz, 2H) 4.84-5.21 (m, 2H) 5.58-5.95 (m, 1H) 6.52 (d, J=3.20 Hz, 1H) 7.25 (d, J=3.20 Hz, 1H) 7.90 (d, J=8.29 Hz, 2H) 8.34 (d, J=7.91 Hz, 2H) 12.32 (s, 1H). LC-MS calcd. for $C_{17}H_{15}F_3N_3O$ [(M+H)$^+$] 334, obsd. 334.1.

In an analogous manner the following compounds were synthesized following the above procedure:

Example 50

7-Ethyl-2-(4-trifluoromethyl-phenyl)-3,7-dihydro-pyrrolo[2,3-d]pyrimidin-4-one

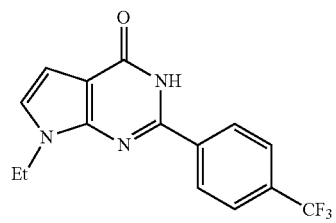

From 2-chloro-7-ethyl-3,7-dihydro-pyrrolo[2,3-d]pyrimidin-4-one (Intermediate C) and 4-(trifluoromethyl)phenylboronic acid: 7-ethyl-2-(4-trifluoromethyl-phenyl)-3,7-dihydro-pyrrolo[2,3-d]pyrimidin-4-one was obtained as a white solid (51.3 mg, 73.3%). $^1$H NMR (300 MHz, DMSO-$d_6$) δ ppm 1.40 (t, J=7.35 Hz, 3H) 4.24 (q, J=6.84 Hz, 2H) 6.53 (d, J=3.58 Hz, 1H) 7.26 (d, J=3.01 Hz, 1H) 7.90 (d, J=7.91 Hz, 2H) 8.34 (d, J=7.91 Hz, 2H) 12.31 (br. s., 1H). LC-MS calcd. for $C_{15}H_{13}F_3N_3O$ [(M+H)$^+$] 308, obsd. 307.9.

Example 51

7-Propyl-2-(4-trifluoromethyl-phenyl)-3,7-dihydro-pyrrolo[2,3-d]pyrimidin-4-one

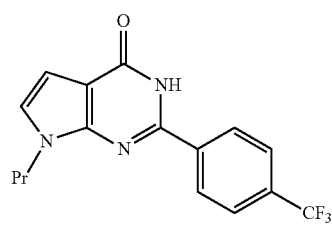

From 2-chloro-7-propyl-3,7-dihydro-pyrrolo[2,3-d]pyrimidin-4-one (Intermediate D) and 4-(trifluoromethyl)phenylboronic acid: 7-propyl-2-(4-trifluoromethyl-phenyl)-3,7-dihydro-pyrrolo[2,3-d]pyrimidin-4-one was obtained as a light yellow solid (46.5 mg, 61.3%). $^1$H NMR (400 MHz, DMSO-$d_6$) δ ppm 0.85 (t, J=7.42 Hz, 3H) 1.82 (sxt, J=7.27 Hz, 2H) 4.17 (t, J=7.03 Hz, 2H) 6.54 (d, J=3.13 Hz, 1H) 7.25 (d, J=3.52 Hz, 1H) 7.90 (d, J=8.59 Hz, 2H) 8.33 (d, J=8.20 Hz, 2H) 12.32 (br. s., 1H). LC-MS calcd. for $C_{16}H_{15}F_3N_3O$ [(M+H)$^+$] 322, obsd. 322.0.

Example 52

7-Allyl-2-(4-trifluoromethyl-phenyl)-3,7-dihydro-pyrrolo[2,3-d]pyrimidin-4-one

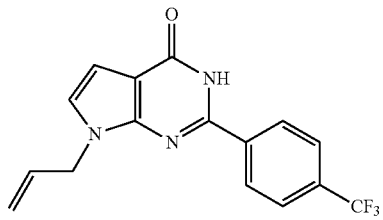 [SMILES: C=CCn1ccc2c(=O)[nH]c(-c3ccc(C(F)(F)F)cc3)nc21]

From 7-allyl-2-chloro-3,7-dihydro-pyrrolo[2,3-d]pyrimidin-4-one (Intermediate E) and 4-(trifluoromethyl)phenylboronic acid: 7-allyl-2-(4-trifluoromethyl-phenyl)-3,7-dihydro-pyrrolo[2,3-d]pyrimidin-4-one was obtained a light yellow solid (82.2 mg, 60.3%). $^1$H NMR (400 MHz, DMSO-$d_6$) δ ppm 4.85 (d, J=5.47 Hz, 2H) 5.05 (dd, J=16.80, 1.56 Hz, 1H) 5.19 (dd, J=10.35, 1.37 Hz, 1H) 5.95-6.20 (m, 1H) 6.57 (d, J=152 Hz, 1H) 7.19 (d, J=3.13 Hz, 1H) 7.90 (d, J=8.59 Hz, 2H) 8.34 (d, J=8.20 Hz, 2H) 12.37 (br. s., 1H). LC-MS calcd. for $C_{16}H_{13}F_3N_3O$ [(M+H)$^+$] 320, obsd. 320.0.

Example 53

7-(3,4-Dihydroxy-butyl)-2-(4-trifluoromethyl-phenyl)-3,7-dihydro-pyrrolo[2,3-d]pyrimidin-4-one

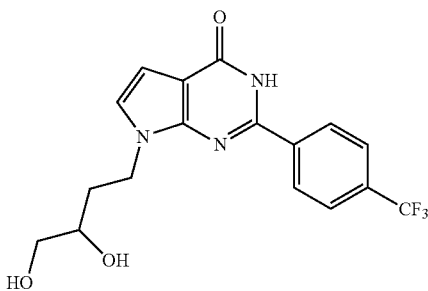 [SMILES: O=c1[nH]c(-c2ccc(C(F)(F)F)cc2)nc2c1ccn2CCC(O)CO]

A solution of 7-but-3-enyl-2-(4-trifluoromethyl-phenyl)-3,7-dihydro-pyrrolo[2,3-d]pyrimidin-4-one (50.3 mg, 151 µmol) in acetone (1.2 mL) and water (0.4 mL) was treated with potassium permanganate (46.1 mg, 292 µmol). The reaction stirred at room temperature overnight. The reaction was filtered through a coarse sintered glass frit, rinsing with ethyl acetate. The filtrate was concentrated in vacuo and then partitioned between water (25 mL) and ethyl acetate (25 mL). The aqueous layer was back extracted with ethyl acetate (25 mL), and the combined organics were washed with a saturated aqueous sodium chloride solution (25 mL), dried over magnesium sulfate, filtered and rinsed with ethyl acetate, and concentrated in vacuo. Flash chromatography (24 g silica gel column, 1-10% methanol/methylene chloride) afforded 7-(3,4-dihydroxy-butyl)-2-(4-trifluoromethyl-phenyl)-3,7-dihydro-pyrrolo[2,3-d]pyrimidin-4-one as a white solid (6.9 mg, 12.4%). $^1$H NMR (300 MHz, DMSO-$d_6$) δ ppm 1.72 (s, 1H) 1.85-2.15 (m, 1H) 3.10-3.53 (m, 3H) 4.09-4.45 (m, 2H) 4.48-4.62 (m, 1H) 4.72 (d, J=5.09 Hz, 1H) 6.53 (d, J=3.20 Hz, 1H) 7.12-7.34 (m, 1H) 7.90 (d, J=8.29 Hz, 2H) 8.34 (d, J=8.48 Hz, 2H) 12.3.1 (s, 1H). LC-MS calcd. for $C_{17}H_{17}F_3N_3O_3$ [(M+H)$^+$] 368, obsd. 368.0.

In an analogous manner the following compound was synthesized following the above procedure:

Example 54

7-(2,3-Dihydroxy-propyl)-2-(4-trifluoromethyl-phenyl)-3,7-dihydro-pyrrolo[2,3-d]pyrimidin-4-one

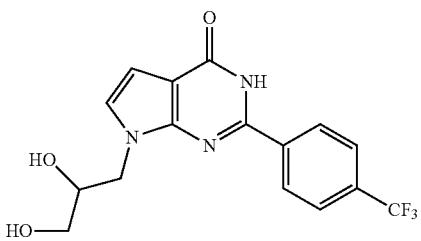 [SMILES: O=c1[nH]c(-c2ccc(C(F)(F)F)cc2)nc2c1ccn2CC(O)CO]

From 7-allyl-2-(4-trifluoromethyl-phenyl)-3,7-dihydro-pyrrolo[2,3-d]pyrimidin-4-one, 7-(2,3-dihydroxy-propyl)-2-(4-trifluoromethyl-phenyl)-3,7-dihydro-pyrrolo[2,3-d]pyrimidin-4-one was obtained as a light yellow solid (2.6 mg, 8.39%). $^1$H NMR (400 MHz, DMSO-$d_6$) δ ppm 3.87 (br. s., 1H) 4.08 (dd, J=13.87, 7.62 Hz, 1H) 4.35 (dd, J=13.87, 4.10 Hz, 1H) 4.75 (t, J=5.66 Hz, 1H) 5.01 (d, J=5.47 Hz, 1H) 6.51 (d, J=3.13 Hz, 1H) 7.21 (d, J=3.52 Hz, 1H) 7.90 (d, J=8.59 Hz, 2H) 8.33 (d, J=8.20 Hz, 2H) 12.31 (br. s., 1H). LC-MS calcd. for $C_{16}H_{15}F_3N_3O_3$ [(M+H)$^+$] 354, obsd. 354.0.

Example 55

N-Ethyl-4-[4-(7-methyl-4-oxo-4,7-dihydro-3H-pyrrolo[2,3-d]pyrimidin-2-yl)-piperazin-1-yl]-benzamide

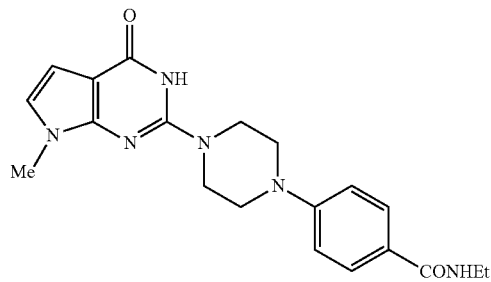

Step 1: A solution of 4-[4-(7-methyl-4-oxo-4,7-dihydro-3H-pyrrolo[2,3-d]pyrimidin-2-yl)-piperazin-1-yl]-benzoic acid ethyl ester (163 mg, 427 µmol) in tetrahydrofuran (1.6 mL) and methanol (0.8 mL) was treated with a 1N aqueous sodium hydroxide solution (748 µL, 748 µmol). The resulting yellow solution was stirred for 3 h at room temperature. At this point, another aliquot of a 1N aqueous sodium hydroxide solution (748 µL, 748 µmol) was added. At this time, the reaction was heated to 75° C. where it was stirred for 1.5 h. The reaction was then diluted with water (10 mL) and extracted with ethyl acetate (20 mL). The aqueous layer was acidified to pH 2 with a 1N aqueous hydrochloric acid solution and further extracted with ethyl acetate (20 mL). The organic layer was washed with a saturated aqueous sodium chloride solution (10 mL). Since product was not soluble in the organic layer, all of the layers were combined and concentrated in vacuo and dried to afford 4-(4-(7-methyl-4-oxo-4,7-dihydro-3H-pyrrolo[2,3-d]pyrimidin-2-yl)piperazin-1-yl)benzoic acid (193 mg, 128%) as a light grey solid. $^1$H NMR (300 MHz, DMSO-d$_6$) δ ppm 3.41 (br. s., 4H) 3.57 (s, 3H) 3.71 (br. s., 4H) 6.25 (d, J=3.39 Hz, 1H) 6.78 (d, J=3.39 Hz, 1H) 7.02 (d, J=9.23 Hz, 2H) 7.79 (d, J=8.85 Hz, 2H) 10.89 (s, 1H) 12.29 (s, 1H). LC-MS calcd. for $C_{18}H_{20}N_5O_3$ [(M+H)$^+$] 354, obsd. 354.1.

Step 2: A solution of 4-(4-(7-methyl-4-oxo-4,7-dihydro-3H-pyrrolo[2,3-d]pyrimidin-2-yl)piperazin-1-yl)benzoic acid (50.4 mg, 143 μmol) in methylene chloride (1.22 mL) was treated with N,N-diisopropylethylamine (74.1 mg, 100 μL, 570 μmol), a 2M solution of ethylamine in tetrahydrofuran (86 μL, 172 μmol), 1-[3-(dimethylamino)propyl]-3-ethylcarbodiimide hydrochloride (49.8 mg, 260 μA mol) and 1-hydroxybenzotriazole (28.9 mg, 214 μmol). The resulting white suspension was stirred at room temperature overnight. At this time, the reaction was diluted with methylene chloride (25 mL) and methanol (5 mL), and was washed with a 1N aqueous hydrochloric acid solution (25 mL), a saturated aqueous sodium bicarbonate solution (25 mL), water (25 mL), and a saturated aqueous sodium chloride solution (25 mL). The organic layer was dried over magnesium sulfate and concentrated in vacuo onto Celite®. The product remained in the aqueous layer, so it was extracted with a solution of 10% methanol/methylene chloride (6×25 mL). The combined organics were concentrated in vacuo onto Celite®. Flash chromatography (10 g silica gel column, 1-10% methanol/methylene chloride) afforded N-ethyl-4-[4-(7-methyl-4-oxo-4,7-dihydro-3H-pyrrolo[2,3-d]pyrimidin-2-yl)-piperazin-1-yl]-benzamide (5.1 mg, 9.4%) as a white solid. $^1$H NMR (300 MHz, DMSO-d$_6$) δ ppm 1.10 (t, J=7.35 Hz, 3H) 3.32 (s, 4H) 3.57 (s, 3H) 3.70 (br. s., 4H) 6.25 (d, J=3.20 Hz, 1H) 6.78 (d, J=3.39 Hz, 1H) 7.00 (d, J=8.67 Hz, 2H) 7.74 (d, J=9.23 Hz, 2H) 8.19 (s, 1H) 10.88 (s, 1H). LC-MS calcd. for $C_{20}H_{25}N_6O_2$ [(M+H)$^+$] 381, obsd. 381.1

Example 56

7-Methyl-2-pyrazol-1-yl-3,7-dihydro-pyrrolo[2,3-d]pyrimidin-4-one

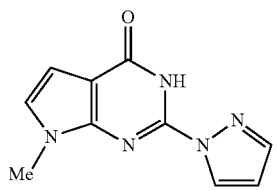 [SMILES: Cn1ccc2c(=O)[nH]c(-n3cccn3)nc21]

A high pressure microwave reaction vial was charged with 2-chloro-7-methyl-3,7-dihydro-pyrrolo[2,3-d]pyrimidin-4-one (Intermediate A) (32.7 mg, 178 μmol) and anhydrous tetrahydrofuran (0.5 mL). The reaction was then treated with 1H-pyrazole (22.3 mg, 328 μmol). The vial was tightly sealed and affixed behind a blast shield. The reaction was warmed to 100° C. where it stirred overnight. At this time, the reaction was heated at 100° C. for 30 min in a microwave. The reaction was concentrated in vacuo onto silica gel. Flash chromatography (12 g silica gel column, 1-10% methanol/methylene chloride) afforded 7-methyl-2-pyrazol-1-yl-3,7-dihydro-pyrrolo[2,3-d]pyrimidin-4-one as a white solid (9.6 mg, 25%). $^1$H NMR (300 MHz, DMSO-d$_6$) δ ppm 3.74 (s, 3H) 6.50 (d, J=3.39 Hz, 1H) 6.67 (dd, J=2.54, 1.79 Hz, 1H) 7.10 (d, J=3.20 Hz, 1H) 7.91 (d, J=1.13 Hz, 1H) 8.61 (d, J=2.45 Hz, 1H) 11.82 (br. s., 1H). LC-MS calcd. for $C_{10}H_{10}N_5O$ [(M+H)$^+$] 216, obsd. 215.9.

Example 57

7-Hydroxymethyl-2-(4-trifluoromethyl-phenyl)-3,7-dihydro-pyrrolo[2,3-d]pyrimidin-4-one

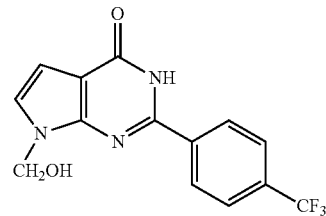 [SMILES: O=c1[nH]c(-c2ccc(C(F)(F)F)cc2)nc2c1ccn2CO]

Step 1: A solution of 2,4-dichloro-7H-pyrrolo[2,3-d]pyrimidine (0.30 g, 1.6 mmol) in anhydrous N,N-dimethylformamide (5.5 mL) cooled to 0° C. was treated with a 60% dispersion of sodium hydride in mineral oil (82.5 mg, 2.06 mmol) under nitrogen. The reaction was stirred at 0° C. for 20-25 min. At this time, the reaction was treated with (2-(chloromethoxy)ethyl)trimethylsilane (340 μL, 1.92 mmol) and was purged with nitrogen. The ice/water bath was removed, and the reaction was stirred at room temperature over 3 nights. At this time, the reaction was diluted with water (50 mL) and was extracted with ethyl acetate (2×50 mL). The combined organics were washed with water (50 mL) and a saturated aqueous sodium chloride solution (50 mL), dried over magnesium sulfate, filtered and rinsed with ethyl acetate, and concentrated in vacuo onto Celite®. Flash chromatography (12 g silica gel column, 1-30% ethyl acetate/hexanes) afforded 2,4-dichloro-7-((2-(trimethylsilyl)ethoxy)methyl)-7H-pyrrolo[2,3-d]pyrimidine as a viscous yellow oil (336.5 mg, 66.3%). $^1$H NMR (300 MHz, DMSO-d$_6$) δ ppm −0.18-−0.01 (m, 9H) 0.74-0.94 (m, 2H) 3.43-3.62 (m, 2H) 5.60 (s, 2H) 6.78 (d, J=3.77 Hz, 1H) 7.90 (d, J=3.77 Hz, 1H). LC-MS calcd. for $C_{12}H_{18}Cl_2N_3OSi$ [(M+H)$^+$] 318, obsd. 317.9.

Step 2: A solution of 2,4-dichloro-7-((2-(trimethylsilyl)ethoxy)methyl)-7H-pyrrolo[2,3-d]pyrimidine (336.5 mg, 1.06 mmol) in tetrahydrofuran (6 mL) was treated with a 2N aqueous potassium hydroxide solution (6 mL) and was warmed to 80° C., where it stirred overnight. At this time, the reaction was concentrated in vacuo and was then carefully brought to pH ~7 with a 2N aqueous hydrochloric acid solution. The material was then diluted with water (25 mL) and extracted with a 10% methanol/methylene chloride solution (2×25 mL). The combined organics were dried over magnesium sulfate, filtered and rinsed with methylene chloride, and concentrated in vacuo onto Celite®. Flash chromatography (40 g silica gel column, 1-50% ethyl acetate/hexanes) afforded 2-chloro-7-((2-(trimethylsilyl)ethoxy)methyl)-3H-pyrrolo[2,3-d]pyrimidin-4(7H)-one as an off-white solid (53.7 mg, 16.9%). $^1$H NMR (300 MHz, DMSO-d$_6$) δ ppm −0.08 (s, 9H) 0.82 (t, J=8.10 Hz, 2H) 3.50 (t, J=8.10 Hz, 2H) 5.42 (s, 2H) 6.53 (d, J=3.20 Hz, 1H) 7.26 (br. s., 1H) 12.98 (br. s., 1H). LC-MS calcd. for $C_{12}H_{19}ClN_3O_2Si$ [(M+H)$^+$] 300, obsd. 300.0.

Step 3: A microwave reaction vial was charged with 2-chloro-7-((2-(trimethylsilyl)ethoxy)methyl)-3H-pyrrolo[2,3-d]pyrimidin-4(7H)-one (53.7 mg, 179 mop and ethanol (850 μL) (650 μL+200 μL rinse). The resulting mixture was treated with a 2M aqueous sodium carbonate solution (270 μL, 540 μmol), 4-(trifluoromethyl)phenylboronic acid (42.1 mg, 222 μmol), and tetrakis(triphenylphosphine)palladium (0) (13.2 mg, 11.4 μmol). The vial was tightly sealed and heated in a microwave at 150° C. for 8 min. At this time, the reaction was filtered through a pad of Celite®, rinsing copiously with methanol, and the filtrate was concentrated in vacuo onto Celite®. Flash chromatography (12 g silica gel column, 10-40% ethyl acetate/hexanes) afforded 2-(4-(trifluoromethyl)phenyl)-7-((2-(trimethylsilyl)ethoxy)methyl)-3H-pyrrolo[2,3-d]pyrimidin-4(7H)-one as a light yellow solid (47.7 mg, 65.0%). $^1$H NMR (300 MHz, DMSO-$d_6$) δ ppm −0.13 (s, 9H) 0.85 (t, J=8.10 Hz, 2H) 3.56 (t, J=8.10 Hz, 2H) 5.58 (s, 2H) 6.59 (d, J=3.39 Hz, 1H) 7.34 (d, J=3.39 Hz, 1H) 7.90 (d, J=7.91 Hz, 2H) 8.36 (d, J=8.29 Hz, 2H) 12.45 (s, 1H). LC-MS calcd. for $C_{19}H_{23}F_3N_3O_2Si$ [(M+H)$^+$] 410, obsd. 410.1.

Step 4: A solution of 2-(4-(trifluoromethyl)phenyl)-7-((2-(trimethylsilyl)ethoxy)methyl)-3H-pyrrolo[2,3-d]pyrimidin-4(7H)-one (47.7 mg, 116 μmol) in anhydrous methylene chloride (6.0 mL) was cooled, under nitrogen, to 0° C. The solution was then treated portion-wise with trifluoroacetic acid (1.5 mL). The reaction was stirred under nitrogen at 0° C. for 30 min. At this time, the reaction was warmed to room temperature where it continued to stir for an additional 3 h. At this time, the reaction was diluted with methylene chloride and was concentrated in vacuo onto Celite® while maintaining a water bath temperature less than or equal to 30° C. Flash chromatography (12 g silica gel column, 40-70% ethyl acetate/hexanes) afforded 7-hydroxymethyl-2-(4-trifluoromethyl-phenyl)-3,7-dihydro-pyrrolo[2,3-d]pyrimidin-4-one as an off-white solid (20.9 mg, 58.0%). $^1$H NMR (300 MHz, DMSO-$d_6$) δ ppm 5.55 (d, J=7.91 Hz, 2H) 6.56 (d, J=3.39 Hz, 1H) 6.63 (t, J=7.35 Hz, 1H) 7.27 (d, J=3.39 Hz, 1H) 7.91 (d, J=8.48 Hz, 2H) 8.37 (d, J=8.10 Hz, 2H) 12.38 (s, 1H). LC-MS calcd. for $C_{14}H_{11}F_3N_3O_2$ [(M+H)$^+$] 310, obsd. 310.0.

Example 58

7-Methyl-2-(3-methyl-3-phenyl-azetidin-1-yl)-3,7-dihydro-pyrrolo[2,3-d]pyrimidin-4-one

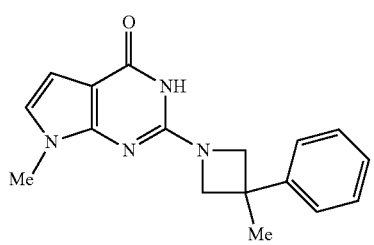 [SMILES: Cn1ccc2c(=O)[nH]c(N3CC(C)(c4ccccc4)C3)nc21]

A mixture of 2-(3-(4-bromophenyl)-3-methylazetidin-1-yl)-7-methyl-3H-pyrrolo[2,3-d]pyrimidin-4(7H)-one (100.3 mg, 269 μmol) in ethyl acetate (2.7 mL) and methanol (2.8 mL) was treated with 10% palladium on carbon (9.2 mg, ~10% weight of starting material used). The flask was capped with a rubber septum and a hydrogen balloon was attached. The reaction was stirred at room temperature overnight. At this time, the reaction was concentrated in vacuo onto Celite®. Flash chromatography (24 g silica gel column, 20-100% ethyl acetate/hexanes) afforded 7-methyl-2-(3-methyl-3-phenyl-azetidin-1-yl)-3,7-dihydro-pyrrolo[2,3-d]pyrimidin-4-one as an off-white solid (43.2 mg, 54.6%). $^1$H NMR (300 MHz, DMSO-$d_6$) δ ppm 1.61 (s, 3H) 3.53 (s, 3H) 4.10 (d, J=8.67 Hz, 2H) 4.24 (d, J=8.29 Hz, 2H) 6.23 (d, J=3.01 Hz, 1H) 6.73 (d, J=3.20 Hz, 1H) 7.13-7.50 (m, 5H) 10.90 (s, 1H). LC-MS calcd. for $C_{17}H_{19}N_4O$ [(M+H)$^+$] 295, obsd. 295.1.

Example 59

7-Cyclopropyl-2-(4-trifluoromethyl-phenyl)-3,7-dihydro-pyrrolo[2,3-d]pyrimidin-4-one

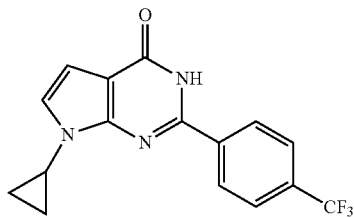 [SMILES: O=c1[nH]c(-c2ccc(C(F)(F)F)cc2)nc2c1ccn2C1CC1]

Step 1: A mixture of 2,4-dichloro-7H-pyrrolo[2,3-d]pyrimidine (210 mg, 1.12 mmol) in methylene chloride (4.86 mL) was treated with triethylamine (314 μL, 2.26 mmol), copper (II) acetate monohydrate (232 mg, 1.16 mmol) and cyclopropylboronic acid (95.9 mg, 1.12 mmol). The reaction was stirred at room temperature overnight. At this time, the reaction was warmed to 70° C. for 3 h. At this time, the reaction was treated with additional triethylamine (314 μL, 2.26 mmol), copper(II) acetate monohydrate (232 mg, 1.16 mmol) and cyclopropylboronic acid (95.9 mg, 1.12 mmol). The reaction was allowed to stir overnight at room temperature. At this time, the reaction was filtered through a plug of Celite®, washing with a 10% methanol/methylene chloride solution. The filtrate was concentrated in vacuo onto silica gel. Flash chromatography (24 g silica gel column, 2-20% ethyl acetate/hexanes) afforded 2,4-dichloro-7-cyclopropyl-7H-pyrrolo[2,3-d]pyrimidine as an off-white solid (70 mg, 27.5%). $^1$H NMR (300 MHz, DMSO-$d_6$) δ ppm 0.82-1.28 (m, 4H) 3.62 (s, 1H) 6.66 (d, J=3.58 Hz, 1H) 7.73 (d, J=3.39 Hz, 1H). LC-MS calcd. for $C_9H_8Cl_2N_3$ [(M+H)$^+$] 228, obsd. 227.9.

Step 2: A mixture of 2,4-dichloro-7-cyclopropyl-7H-pyrrolo[2,3-d]pyrimidine (68 mg, 298 μmol) in a 2N aqueous potassium hydroxide solution (1.67 ml, 3.34 mmol) was heated to 100° C. overnight. At this time, the reaction was cooled to room temperature. The reaction was diluted with water (~50 mL) and then neutralized by the addition of a 2N aqueous hydrochloric acid solution. The product was extracted into a 10% methanol/methylene chloride solution (3×25 mL), dried over sodium sulfate, filtered and concentrated in vacuo to afford 2-chloro-7-cyclopropyl-3,7-dihydro-pyrrolo[2,3-d]pyrimidin-4-one as a light yellow solid (59.9 mg, 95.8%). $^1$H NMR (300 MHz, DMSO-$d_6$) δ ppm 0.78-1.17 (m, 4H) 3.50 (s, 1H) 6.42 (d, J=3.39 Hz, 1H) 7.07 (br. s., 1H) 12.87 (br. s., 1H). LC-MS calcd. for $C_9H_9ClN_3O$ [(M+H)$^+$] 210, obsd. 209.9.

Step 3: A microwave reaction vial was charged with 2-chloro-7-cyclopropyl-3,7-dihydro-pyrrolo[2,3-d]pyrimidin-4-one (57 mg, 272 μmol), 4-(trifluoromethyl)phenylboronic acid (62.0 mg, 326 μmol), a 2M aqueous sodium carbonate solution (408 μL, 816 μmol), and tetrakis (triphenylphosphine)palladium(0) (15.7 mg, 13.6 μmol) in ethanol (1.09 mL). The reaction mixture was heated in a microwave at 150° C. for 8 min. At this time, the reaction was diluted with methylene chloride and was filtered through a pad of Celite®, washing with a 10% methanol/methylene chloride solution. The filtrate was dried over sodium sulfate, filtered, and concentrated in vacuo onto Celite®. Flash chromatography (12 g silica gel column, 25-50% ethyl acetate/hexanes) afforded 7-cyclopropyl-2-(4-trifluoromethyl-phenyl)-3,7-dihydro-pyrrolo[2,3-d]pyrimidin-4-one as a white solid (48.5 mg, 55.9%). $^1$H NMR (300 MHz, DMSO-d$_6$) δ ppm 0.71-1.29 (m, 4H) 3.65 (d, J=4.90 Hz, 1H) 6.49 (d, J=3.58 Hz, 1H) 7.15 (d, J=3.39 Hz, 1H) 7.91 (d, J=8.67 Hz, 2H) 8.35 (d, J=7.91 Hz, 2H) 12.35 (br. s., 1H). LC-MS calcd. for $C_{16}H_{13}F_3N_3O$ [(M+H)$^+$] 320, obsd. 320.0.

Example 60

2-[4-(2-Fluoro-phenyl)-piperazin-1-yl]-7-hydroxymethyl-3,7-dihydro-pyrrolo[2,3-d]pyrimidin-4-one

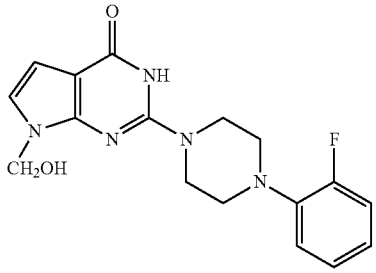 [SMILES: O=c1[nH]c(N2CCN(c3ccccc3F)CC2)nc2c1ccn2CO]

Step 1: A solution of 2,4-dichloro-7H-pyrrolo[2,3-d]pyrimidine (0.30 g, 1.6 mmol) in anhydrous N,N-dimethylformamide (5.5 mL) cooled to 0° C. was treated with a 60% dispersion of sodium hydride in mineral oil (82.5 mg, 2.06 mmol) under nitrogen. The reaction was stirred at 0° C. for 20-25 min. At this time, the reaction was then treated with (2-(chloromethoxy)ethyl)trimethylsilane (340 μL, 1.92 mmol) and was purged with nitrogen. The ice/water bath was removed, and the reaction was allowed to warm to room temperature where it stirred over 3 nights. At this time, the reaction was diluted with water (50 mL) and was extracted with ethyl acetate (2×50 mL). The combined organics were washed with water (50 mL) and a saturated aqueous sodium chloride solution (50 mL), dried over magnesium sulfate, filtered and rinsed with ethyl acetate, and concentrated in vacuo onto Celite®. Flash chromatography (12 g silica gel column, 1-30% ethyl acetate/hexanes) afforded 2,4-dichloro-7-((2-(trimethylsilyl)ethoxy)methyl)-7H-pyrrolo[2,3-d]pyrimidine as a viscous yellow oil (336.5 mg, 66.3%). $^1$H NMR (300 MHz, DMSO-d$_6$) δ ppm −0.26-0.05 (m, 9H) 0.74-0.98 (m, 2H) 3.44-3.65 (m, 2H) 5.60 (s, 2H) 6.78 (d, J=3.77 Hz, 1H) 7.90 (d, J=3.77 Hz, 1H). LC-MS calcd. for $C_{12}H_{18}Cl_2N_3OSi$ [(M+H)$^+$] 318, obsd. 317.9.

Step 2: A solution of 2,4-dichloro-7-((2-(trimethylsilyl)ethoxy)methyl)-7H-pyrrolo[2,3-d]pyrimidine (336.5 mg, 1.06 mmol) in tetrahydrofuran (6 mL) was treated with a 2N aqueous potassium hydroxide solution (6 mL). The reaction was warmed to 80° C. where it stirred overnight. At this time, the reaction was concentrated in vacuo. The resulting mixture was then carefully brought to pH ~7 with a 2N aqueous hydrochloric acid solution, diluted with water (25 mL) and extracted with a 10% methanol/methylene chloride solution (2×25 mL). The combined organics were dried over magnesium sulfate, filtered and rinsed with methylene chloride and concentrated in vacuo onto Celite®. Flash chromatography (40 g silica gel column, 1-50% ethyl acetate/hexanes) afforded 2-chloro-7-((2-(trimethylsilyl)ethoxy)methyl)-3H-pyrrolo[2,3-d]pyrimidin-4(7H)-one as an off-white solid (53.7 mg, 16.9%). $^1$H NMR (300 MHz, DMSO-d$_6$) δ ppm −0.08 (s, 9H) 0.82 (t, J=8.10 Hz, 2H) 3.50 (t, J=8.10 Hz, 2H) 5.42 (s, 2H) 6.53 (d, J=3.20 Hz, 1H) 7.26 (br. s., 1H) 12.98 (br. s., 1H). LC-MS calcd. for $C_{12}H_{19}ClN_3O_2Si$ [(M+H)$^+$] 300, obsd. 300.0.

Step 3: A high pressure reaction vial was charged with 2-chloro-7-((2-(trimethylsilyl)ethoxy)methyl)-3H-pyrrolo[2,3-d]pyrimidin-4(7H)-one (50 mg, 175 μmol) and ethanol (460 μL). The reaction was treated with 1-(2-fluorophenyl)piperazine (63.1 mg, 55.3 μL, 350 μmol) and was sealed. The reaction was then heated to 100° C. where it stirred overnight. At this time, the reaction was allowed to cool to room temperature. It was then diluted with methylene chloride and methanol and concentrated in vacuo onto Celite®. Flash chromatography (12 g silica gel column, 1-10% methylene chloride/methanol) afforded 2-(4-(2-fluorophenyl)piperazin-1-yl)-7-((2-(trimethylsilyl)ethoxy)methyl)-3H-pyrrolo[2,3-d]pyrimidin-4(7H)-one as a purple oil (31.5 mg, 40.6%). $^1$H NMR (400 MHz, DMSO-d$_6$) δ ppm −0.32-0.07 (m, 9H) 0.84 (t, J=8.01 Hz, 2H) 3.07 (br. s., 4H) 3.51 (t, J=8.01 Hz, 2H) 3.73 (br. s., 4H) 5.34 (s, 2H) 6.31 (d, J=3.52 Hz, 1H) 6.89 (d, J=3.52 Hz, 1H) 6.95-7.25 (m, 4H) 10.83-11.10 (m, 1H). LC-MS calcd. for $C_{22}H_{31}FN_5O_2S$ [(M+H)$^+$] 444, obsd. 444.1.

Step 4: A solution of 2-(4-(2-fluorophenyl)piperazin-1-yl)-7-((2-(trimethylsilyl)ethoxy)methyl)-3H-pyrrolo[2,3-d]pyrimidin-4(7H)-one (30 mg, 67.6 μmol) in methylene chloride (3.38 mL) was treated dropwise with trifluoroacetic acid (1.13 mL). The reaction was stirred at room temperature for 2 h, and was then concentrated in vacuo onto Celite®. Flash chromatography (12 g silica gel column, 40-80% ethyl acetate/hexanes) afforded 2-[4-(2-fluoro-phenyl)-piperazin-1-yl]-7-hydroxymethyl-3,7-dihydro-pyrrolo[2,3-d]pyrimidin-4-one as a light grey solid (11.2 mg, 48.2%). $^1$H NMR (400 MHz, DMSO-d$_6$) δ ppm 2.97-3.15 (m, 4H) 3.71 (d, J=5.08 Hz, 4H) 5.32 (d, J=7.42 Hz, 2H) 6.28 (d, J=3.52 Hz, 1H) 6.31-6.39 (m, 1H) 6.85 (d, J=3.52 Hz, 1H) 6.93-7.21 (m, 4H) 10.89 (s, 1H). LC-MS calcd. for $C_{17}H_{19}FN_5O_2$ [(M+H)$^+$] 344, obsd. 344.1.

Example 61

2-(4-(2,6-difluorophenyl)piperazin-1-yl)-7-(2,3-dihydroxypropyl)-3H-pyrrolo[2,3-d]pyrimidin-4(7H)-one

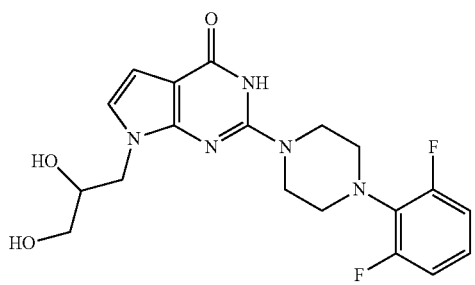 [SMILES: O=c1[nH]c(N2CCN(c3c(F)cccc3F)CC2)nc2c1ccn2CC(O)CO]

Step 1: A mixture of 7-allyl-2-chloro-3,7-dihydro-pyrrolo[2,3-d]pyrimidin-4-one (Intermediate E, 40.8 mg, 195 μmol), 4-methylmorpholine N-oxide (11.4 mg, 97.3 μmol), and potassium osmate(VI) dihydrate (717 μg, 1.95 μmol) in tert-butanol (730 μL) and water (243 μL) cooled to 0° C. was treated with a 50% aqueous hydrogen peroxide solution (20 μL, 292 μmol). The reaction was allowed to warm to room temperature, where it stirred overnight. At this time, the reaction was diluted with methanol and absorbed onto Celite®. Flash chromatography (4 g silica gel column, 2-8% methanol/methylene chloride) afforded 2-chloro-7-(2,3-dihydroxy-propyl)-3,7-dihydro-pyrrolo[2,3-d]pyrimidin-4-one as an off-white solid (16.4 mg, 34.6%). $^1$H NMR (300 MHz, DMSO-$d_6$) δ ppm 3.57 (s, 1H) 3.80 (d, J=9.42 Hz, 1H) 3.85-3.99 (m, 1H) 4.14-4.29 (m, 1H) 4.75 (t, J=5.75 Hz, 1H) 4.98 (d, J=5.46 Hz, 1H) 6.46 (d, J=3.39 Hz, 1H) 7.12 (d, J=3.20 Hz, 1H) 12.80 (s, 1H). LC-MS calcd. for $C_9H_{11}ClN_3O_3$ [(M+H)$^+$] 244, obsd. 243.9.

Step 2: A mixture of 2-chloro-7-(2,3-dihydroxy-propyl)-3,7-dihydro-pyrrolo[2,3-d]pyrimidin-4-one (16 mg, 65.7 μmol) in ethanol (460 μL) was treated with 1-(2,6-difluorophenyl)piperazine trifluoroacetic acid salt (40.9 mg, 131 μmol) and N,N-diisopropylethylamine (36.6 μL, 210 μmol). The reaction was heated to 100° C., where it stirred overnight. At this time, the reaction was allowed to cool to room temperature. The reaction was then diluted with methylene chloride and methanol and concentrated in vacuo onto Celite®. Flash chromatography (4 g silica gel column, 1-4% methanol/methylene chloride) afforded 2-[4-(2,6-difluoro-phenyl)-piperazin-1-yl]-7-(2,3-dihydroxy-propyl)-3,7-dihydro-pyrrolo[2,3-d]pyrimidin-4-one as a purple solid (15.3 mg, 57.5%). $^1$H NMR (400 MHz, DMSO-$d_6$) δ ppm 3.17 (br. s., 4H) 3.23-3.31 (m, 2H) 3.54-3.70 (m, 4H) 3.71-3.93 (m, 2H) 4.09 (dd, J=13.68, 4.39 Hz, 1H) 4.67 (t, J=5.77 Hz, 1H) 4.94 (d, J=5.27 Hz, 1H) 6.24 (d, J=3.51 Hz, 1H) 6.80 (d, J=3.51 Hz, 1H) 6.95-7.24 (m, 3H) 10.85 (br. s., 1H). LC-MS calcd. for $C_{19}H_{22}F_2N_5O_3$ [(M+H)$^+$] 406, obsd. 406.0.

Example 62

7-Methyl-2-phenyl-3,7-dihydro-pyrrolo[2,3-d]pyrimidin-4-one

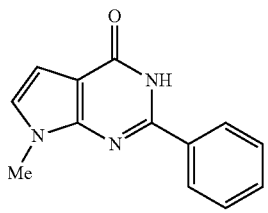 [SMILES: Cn1ccc2c(=O)[nH]c(-c3ccccc3)nc21]

Step 1: A solution of 2-phenyl-3,7-dihydro-pyrrolo[2,3,-d]pyrimidin-4-one (100 mg, 0.47 mmol) and triethylamine (144 mg, 1.42 mmol) in tetrahydrofuran (3 mL) was treated with chlorotriethylsilane (71.4 mg, 0.47 mmol) at room temperature. After stirring at room temperature for 4 h, the reaction mixture was filtered through a pad of Celite® and was washed with diethyl ether. The filtrate was concentrated in vacuo. The resulting residue was partitioned between a saturated aqueous sodium bicarbonate solution and ethyl acetate. The aqueous layer was extracted with ethyl acetate. The combined organics were concentrated in vacuo to afford 2-phenyl-4-triethylsilanyloxy-7-H-pyrrolo[2,3,-d]pyrimidine. The material was used without further purification.

Step 2: A solution of 2-phenyl-4-triethylsilanyloxy-7-H-pyrrolo[2,3,-d]pyrimidine (70 mg, 0.22 mmol) in tetrahydrofuran (2 mL) cooled to 0° C. was treated with a 60% dispersion of sodium hydride in mineral oil (25.8 mg, 1.08 mmol) and iodomethane (61.1 mg, 0.43 mmol). After stirring for 20 min, the reaction mixture was poured onto a saturated aqueous ammonium chloride solution and was extracted with ethyl acetate. The combined organics were washed with a saturated aqueous sodium chloride solution and were concentrated in vacuo. Flash chromatography (40/1 methylene chloride/methanol) afforded 7-methyl-2-phenyl-3,7-dihydropyrrolo[2,3,-d]pyrimidine-4-one (12 mg, 24.8%) as a white solid. $^1$H NMR (400 MHz, DMSO-$d_6$) δ ppm 3.78 (s, 3H) 6.50 (d, J=3.51 Hz, 1H) 7.15 (d, J=3.26 Hz, 1H) 7.41-7.68 (m, 3H) 8.09-8.25 (m, 2H) 12.10 (s, 1H); LC-MS calcd. for $C_{13}H_{12}N_3O$ [(M+H)$^+$] 226, obsd. 225.9.

Example 63

2-[4-[2 6-difluoro-4-(2-methoxyethoxy)phenyl]piperazin-1-yl]-7-(2-hydroxyethyl)-3H-pyrrolo[2,3-d]pyrimidin-4-one

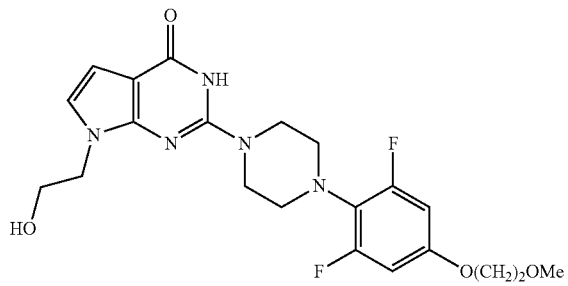

A solution of 2-chloro-7-(2-hydroxyethyl)-3H,4H,7H-pyrrolo[2,3-d]pyrimidin-4-one (150 mg, 0.70 mmol, 1.00 equiv), 1-[2,6-difluoro-4-(2-methoxyethoxy)phenyl]piperazine (192 mg, 0.71 mmol, 1.00 equiv) and DIEA (182 mg, 1.41 mmol, 2.00 equiv) in ethanol (2 mL) was placed in an 8-mL sealed tube. The reaction mixture was irradiated with microwave radiation for 30 min at 140° C. and then cooled back to room temperature. The crude product was collected by filtration then purified by Prep-HPLC with the following conditions (Prep-HPLC-005): Column: XBridge Prep $C_{18}$ OBD Column, 5 um, 19*150 mm; mobile phase: water with 10 mmol NH$_4$HCO$_3$ and MeCN (MeCN 35.0%, MeCN up to 50.0% in 10 min, up to 95.0% in 1 min, hold 95.0% in 1 min, down to 35.0% in 2 min); Detector, UV 254/220 nm to yield 98.3 mg (31%) of 2-[4-[2,6-difluoro-4-(2-methoxyethoxy)phenyl]piperazin-1-yl]-7-(2-hydroxyethyl)-3H,4H,7H-pyrrolo[2,3-d]pyrimidin-4-one as a white solid. $^1$HNMR (400 MHz, DMSO-$d_6$) δ ppm 3.09-3.06 (m, 4H), 3.28 (s, 3H), 3.69-3.61 (m, 8H), 4.02-3.99 (m, 2H), 4.08-4.06 (m, 2H), 4.85 (t, J=5.6 Hz, 1H), 6.23 (d, J=3.2 Hz, 1H), 6.72 (d, J=11.2 Hz, 2H), 6.81 (d, J=3.2 Hz, 1H), 10.81 (s, 1H). LC-MS calcd. for $C_{21}H_{26}F_2N_5O_4$ [(M+H)$^+$] 450, obsd. 450.3.

Example 64

μHTS-TNKS-IWR2TR-FRET Binding Assay (10 μL/well in BD1536-well plate, a single point)
Reagents and Stock Solutions
Tankyrase 1 (TNKS1): 184.3 μM=5.2 mg/mL His6-TNKS1, MW=28.2 KDa (construct: 1088-1327, 1266M) in 20 mM Tris pH 8, 150 mM NaCl, 10% glycerol, and 0.5 mM TCEP Alternatively, in place of His6-TNKS1 can use either His6-tankyrase 2 (construct: 934-1166) (His6-TNKS2) or His6-PARP1 (full length).

Biotin-IWR2: 10 mM Biotin-IWR2 stock in DMSO, stored at −20° C.

Positive control: 10 mM XAV 939 in DMSO, stored at −20° C.

Eu-Streptavidin: 38.1 µM (2.1 mg/mL) Eu-SA (Bio#Eu-2212, Lot#N 18001-BDHO2)

APC-anti-His Ab: 8.50 µM SL-APC, 8.26 µM anti-6His antibody-SureLight APC (Columia Bioscience, Cat#D3-1711, Lot#N01010-AAH04)

Assay plate: BD 1536-well, clear/black plate (Cat#353255)

NP-40: 10% NP-40 solution (PIERCE, Cat#28324, Lot #97101671)

Assay Buffer Preparation

Assay buffer 1a (AB 1a) for TNKS dilution: 50 mM Tris, pH 7.4, 100 mM sodium chloride solution, 1 mM magnesium chloride solution, 1 mM DL-dithiothreitol solution, 0.2 mg/mL bovine serum albumin solution, 0.025% NP-40.

Assay buffer 1b (AB 1b) for Biotin-IWR2 dilution: 50 mM Tris, pH 7.4, 100 mM sodium chloride solution, 1 mM magnesium chloride solution, 1 mM DL-dithiothreitol solution, 0.2 mg/mL bovine serum albumin solution, 0.05% NP-40

Assay buffer 1c (AB 1c) for compound dilution: 50 mM Tris, pH 7.4, 100 mM sodium chloride solution, 1 mM magnesium chloride solution, 1 mM DL-dithiothreitol solution, 0.2 mg/mL bovine serum albumin solution Assay buffer 2 (AB2) for Eu/APC: 50 mM Tris, pH 7.4, 100 mM sodium chloride solution, 1 mM magnesium chloride solution, 0.2 mg/mL bovine serum albumin solution Reagent Stock Solution Preparation Prepare Biotinylated IWR2 stock solution (3.33× stock) for TOTL and cpd wells: 200 nM Biotin-IWR2 in 5% DMSO/AB1b buffer Prepare BLANK well stock solution: 5% DMSO/AB1b buffer Prepare POSITIVE CONTROL well stock solution (3.33× stock): 200 nM XAV939 in 200 nM Biotin-IWR2/5% DMSO/AB1b buffer Prepare TNKS1 stock solution (5× stock): 300 nM TNKS in AB1a buffer (Alternatively, use TNKS2 or PARP1 stock solutions.)

Prepare Eu/APC stock solution (5× stock): 3.5 nM Eu-SA/50 nM APC-His6Ab in AB2 buffer Assay Procedure Compound Preparations:

Add 25 µL/well 1.5% DMSO/AB1c buffer in each compound well to the compound concentration at 74 µM in 8.8% DMSO/AB1c buffer or in the 2 µL DMSO CONTROL wells (BLANK, TOTAL and POSITIVE wells) in the compound plate.

Transfer 3 µL/well above solution (solution 1,2,3) to an empty assay plate (BD1536-well plate) as follows:

TOTL and cpd wells: Solution 1 (Biotin-IWR2):
BLNK wells: Solution 2 (No Biotin-IWR2):
POSITIVE CONTROL wells: Solution 3 (Biotin-IWR2+ XAV939)

Transfer 3 µL/well of the above diluted compound solutions or compound dilution buffer to the above assay plate.

Add 2 µL/well of 300 nM TNKS stock solution (4) to every well in the above assay plate.

Centrifuge the assay plate at 2100 rpm for 2 minutes.
Incubate the assay plate at 26° C. for 30 minutes.
Centrifuge the assay plate at 2100 rpm for 2 minutes.
Incubate the assay plate at 26° C. for 60 minutes.
Read the assay plate immediately at excitation wavelength of 330 nM and emission wavelength of 615 and 665 nM in time resolved fluorescence mode.

Final Assay Conditions
Biotin-IWR2: 60 nM
TNKS: 60 nM
Eu-SA: 0.7 nM
APC-His Ab: 10 nM
XAV939 (+ve control): 60 nM at ~70% Inhibition
General Library compounds: 22.23 µM in 4% DMSO Example 65

TNKS1 NAM Assay

NADase activity of Tankyrase 1 was measured by quantifying released nicotinamide using liquid chromatography mass spectrometry. Varying concentrations of experimental compounds were incubated in 10 µL reactions containing 25 nM recombinant Tankyrase 1, 1 mM NAD+, 5 µM d4-nicotinamide internal standard, 2% DMSO, 50 mM Tris pH 7.5, 5 mM $CaCl_2$, and 0.01% Triton X-100 for 1 h at RT. Reactions were quenched by mixing 2 µL of the reaction mixture with 98 µL of 0.05% formic acid. 1 µL of quenched reaction was loaded onto a reverse phase BEH-Phenyl column (Waters) pre-equilibrated with 1 mM ammonium formate and eluted with a linear gradient to 80% acetonitrile. Compound $IC_{50}$s were determined by four-parameter curve fitting.

Representative compound data for assays are listed below in Table I. Values are in uM.

TABLE I

| Example | TNKS1 $IC_{50}$ (µM) | TNKS2 $IC_{50}$ (µM) | PARP1 $IC_{50}$ (µM) |
| --- | --- | --- | --- |
| 1 | 0.722 | 0.593 | 0.143 |
| 2 | 0.070 | 0.066 | 0.564 |
| 3 | 0.042 | 0.051 | 1.062 |
| 4 | 0.134 | 0.118 | 0.437 |
| 5 | 0.030 | 0.035 | 1.182 |
| 6 | 0.034 | 0.036 | 2.212 |
| 7 | 0.494 | 0.405 | >50 |
| 8 | 0.190 | 0.143 | 0.339 |
| 9 | 0.070 | 0.063 | 0.618 |
| 10 | 0.111 | 0.121 | 0.603 |
| 11 | 0.358 | 0.285 | 0.471 |
| 12 | 1.913 | 1.835 | 1.722 |
| 13 | 0.112 | 0.126 | 0.604 |
| 14 | 0.466 | 0.427 | 0.229 |
| 15 | 0.348 | 0.192 | 3.457 |
| 16 | 0.915 | 1.067 | 1.258 |
| 17 | 0.027 | 0.032 | 1.083 |
| 18 | 0.059 | 0.059 | 0.758 |
| 19 | 0.043 | 0.034 | 1.052 |
| 20 | 0.031 | 0.036 | 1.217 |
| 21 | 0.081 | 0.090 | 0.612 |
| 22 | 0.097 | 0.074 | 0.453 |
| 23 | 0.028 | 0.031 | 42.13 |
| 24 | 0.035 | 0.047 | 1.283 |
| 25 | 0.292 | 0.200 | 0.557 |
| 26 | 0.204 | 0.153 | 1.254 |
| 27 | 5.667 | 6.786 | >50 |
| 28 | 0.040 | 0.080 | 3.283 |
| 29 | 0.043 | 0.045 | 0.732 |
| 30 | 0.031 | 0.033 | 1.401 |
| 31 | 0.155 | 0.133 | 0.318 |
| 32 | 0.129 | 0.090 | 0.229 |
| 33 | 6.177 | 6.084 | 1.119 |

TABLE I-continued

| Example | TNKS1 IC$_{50}$ (μM) | TNKS2 IC$_{50}$ (μM) | PARP1 IC$_{50}$ (μM) |
|---|---|---|---|
| 34 | 0.025 | 0.024 | 1.366 |
| 35 | 0.051 | 0.059 | 1.629 |
| 36 | 0.273 | 0.251 | 21.05 |
| 37 | 0.110 | 0.217 | 1.127 |
| 38 | 0.038 | 0.045 | 0.785 |
| 39 | 0.054 | 0.058 | 0.854 |
| 40 | 0.117 | 0.109 | 0.289 |
| 41 | 0.764 | 0.568 | 0.307 |
| 42 | 0.228 | 0.235 | 0.166 |
| 43 | 0.110 | 0.143 | 1.184 |
| 44 | 0.088 | 0.084 | 0.0933 |
| 45 | 0.040 | 0.039 | 0.842 |
| 46 | 0.123 | 0.132 | >50 |
| 47 | 0.164 | 0.135 | 0.292 |
| 48 | 0.043 | 0.043 | 4.7 |
| 49 | 1.283 | 1.361 | >50 |
| 50 | 0.176 | 0.163 | >50 |
| 51 | 0.535 | 0.640. | >50 |
| 52 | 0.750 | 0.730 | >50 |
| 53 | 0.240 | 0.168 | 2.383 |
| 54 | 0.425 | 0.237 | 13.46 |
| 55 | 0.037 | 0.040 | 0.449 |
| 56 | 7.803 | 9.158 | >50 |
| 57 | 0.048 | 0.065 | 1.877 |
| 58 | 0.108 | 0.100 | 1.313 |
| 59 | 0.545 | 0.619 | >50 |
| 60 | 0.033 | 0.055 | 10.61 |
| 61 | 0.034 | 0.028 | 14.79 |
| 62 | 0.117 | 0.154 | 3.915 |
| 63 | 0.00967[2] | | |

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound of the formula (I)

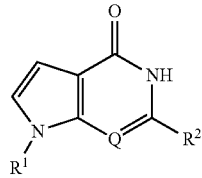

(I)

wherein
Q and X are independently in each occurrence N;
$R^1$ is selected from the group consisting of $C_{1-6}$ alkyl, $C_{1-6}$ alkenyl, $C_{1-6}$ hydroxyalkyl, $C_{1-6}$-dihydroxyalkyl, $C_{3-7}$ cycloalkyl;
$R^2$ is

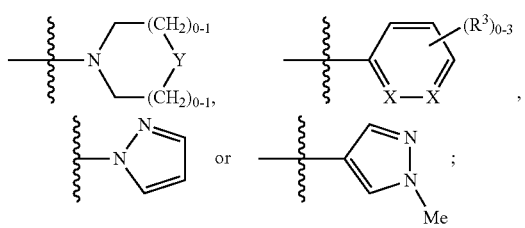

Y is selected from the group consisting of $CR^4R^5$, $NR^4$ or —O— wherein $R^5$ is hydrogen, $C_{1-6}$ alkyl;
$R_4$ is $C_{1-6}$ alkyl, $C_{1-6}$ alkylsulfonyl, $C_{1-6}$ acyl, phenyl or heteroaryl said heteroaryl selected from pyridinyl, pyrazinyl or pyrimidinyl and said phenyl and said heteroaryl optionally substituted by one to three substituents independently selected from the group consisting of halogen, CN, $C_{1-6}$ alkylsulfonyl, $C_{1-6}$ haloalkyl, $C_{1-6}$ hydroxyalkyl, $C_{1-3}$ alkoxy-$C_{1-3}$ alkyl, $C_{1-6}$ alkoxycarbonyl, carboxy, $CONR_{4b}R_{4c}$ wherein $R_{4b}$ and $R_{4c}$ are independently in each occurrence hydrogen or $C_{1-3}$ alkyl and $OR_{4a}$ wherein $R_{4a}$ is selected from the group consisting of (i) hydrogen, (ii) $C_{1-6}$ alkyl, (iii) $C_{1-3}$ alkoxy-$C_{1-3}$ alkyl, (iv) $C_{1-6}$ hydroxyalkyl and (v) $C_{1-6}$ dihydroxyalkyl;
$R_6$ is halogen or hydrogen,
$R_3$ is selected from the group consisting of hydrogen, $C_{1-6}$ alkyl, substituted alkyl, $C_{1-6}$ haloalkyl, $C_{1-6}$ hydroxyalkyl, $C_{1-6}$ dihydroxyalkyl, $C_{1-3}$ alkoxy-$C_{1-3}$ alkyl, halogen, CN, trifluoromethyl, $C_{1-6}$alkoxycarbonyl, $C_{1-6}$ alkylsulfonyl, $CONR_{4b}R_{4c}$ wherein $R_{4b}$ and $R_{4c}$ are independently in each occurrence hydrogen or $C_{1-3}$ alkyl, and $OR_{3a}$ wherein $R_{3a}$ is selected from the group consisting of (i) hydrogen, (ii) $C_{1-6}$ alkyl, (iii) $C_{1-3}$ alkoxy-$C_{1-3}$ alkyl, (iv) $C_{1-6}$ hydroxyalkyl and (v) $C_{1-6}$ dihydroxyalkyl; or, a pharmaceutically acceptable salt thereof.

2. The compound of claim 1 wherein:
$R_1$ is selected from hydrogen or alkyl,
$R^2$ is

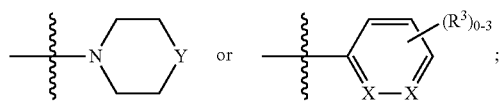

$R_4$ is phenyl or heteroaryl said heteroaryl selected from pyridinyl, pyrazinyl or pyrimidinyl and said phenyl and said heteroaryl optionally substituted by one to three substituents independently selected from the group consisting of halogen, CN, $C_{1-6}$ alkylsulfonyl, $C_{1-6}$ haloalkyl, $C_{1-6}$ hydroxyalkyl, $C_{1-3}$ alkoxy-$C_{1-3}$ alkyl, $C_{1-6}$ alkoxycarbonyl, carboxy, $CONR_{4b}R_{4c}$ wherein $R_{4b}$ and $R_{4c}$ are independently in each occurrence hydrogen or $C_{1-3}$ alkyl and $OR_{4a}$ wherein $R_{4a}$ is selected from the group consisting of (i) $C_{1-6}$ alkyl, (ii) $C_{1-3}$ alkoxy-$C_{1-3}$ alkyl, (iii) $C_{1-6}$ hydroxyalkyl and (iv) $C_{1-6}$ dihydroxyalkyl.

3. The compound of claim 1 selected from the group consisting of:
- 7-Methyl-2-(4-pyridin-4-yl-piperazin-1-yl)-3,7-dihydropyrrolo[2,3-d]pyrimidin-4-one,
- 4-[4-(7-Methyl-4-oxo-4,7-dihydro-3H-pyrrolo[2,3-d]pyrimidin-2-yl)-piperazin-1-yl]-benzoic acid ethyl ester,
- 2-[4-(4-Chloro-phenyl)-piperazin-1-yl]-7-methyl-3,7-dihydro-pyrrolo[2,3-d]pyrimidin-4-one,
- 7-Methyl-2-(4-pyridin-2-yl-piperazin-1-yl)-3,7-dihydropyrrolo[2,3-d]pyrimidin-4-one,
- 2-[4-(4-Fluoro-2-methanesulfonyl-phenyl)-piperazin-1-yl]-7-methyl-3,7-dihydro-pyrrolo[2,3-d]pyrimidin-4-one,
- 7-Methyl-2-[4-(3-trifluoromethyl-pyridin-2-yl)-piperazin-1-yl]-3,7-dihydro-pyrrolo[2,3-d]pyrimidin-4-one,
- 2-[4-(3,5-Dichloro-phenyl)-piperazin-1-yl]-7-methyl-3,7-dihydro-pyrrolo[2,3-d]pyrimidin-4-one,
- 7-Methyl-2-(4-pyrimidin-2-yl-piperazin-1-yl)-3,7-dihydro-pyrrolo[2,3-d]pyrimidin-4-one,
- 2-[4-(7-Methyl-4-oxo-4,7-dihydro-3H-pyrrolo[2,3-d]pyrimidin-2-yl)-piperazin-1-yl]-nicotinonitrile,
- 4-(7-Methyl-4-oxo-4,7-dihydro-3H-pyrrolo[2,3-d]pyrimidin-2-yl)-3,4,5,6-tetrahydro-2H-[1,2']bipyrazinyl-3'-carbonitrile, and,
- 7-Methyl-2-(4-methyl-piperazin-1-yl)-3,7-dihydro-pyrrolo[2,3-d]pyrimidin-4-one.

4. The compound of claim 1 selected from the group consisting of
- 7-Methyl-2-morpholin-4-yl-3,7-dihydro-pyrrolo[2,3-d]pyrimidin-4-one,
- 2-(4-Methanesulfonyl-piperazin-1-yl)-7-methyl-3,7-dihydro-pyrrolo[2,3-d]pyrimidin-4-one,
- 2-(4-Acetyl-piperazin-1-yl)-7-methyl-3,7-dihydro-pyrrolo[2,3-d]pyrimidin-4-one,
- 2-[3-(4-Bromo-phenyl)-3-methyl-azetidin-1-yl]-7-methyl-3,7-dihydro-pyrrolo[2,3-d]pyrimidin-4-one,
- 7-Methyl-2-(3-phenyl-pyrrolidin-1-yl)-3,7-dihydro-pyrrolo[2,3-d]pyrimidin-4-one,
- 2-[4-(4-Fluoro-phenyl)-piperazin-1-yl]-7-methyl-3,7-dihydro-pyrrolo[2,3-d]pyrimidin-4-one,
- 2-[4-(3-Fluoro-phenyl)-piperazin-1-yl]-7-methyl-3,7-dihydro-pyrrolo[2,3-d]pyrimidin-4-one,
- 2-[4-(7-Methyl-4-oxo-4,7-dihydro-3H-pyrrolo[2,3-d]pyrimidin-2-yl)-piperazin-1-yl]-benzonitrile,
- 2-[4-(2,4-Difluoro-phenyl)-piperazin-1-yl]-7-methyl-3,7-dihydro-pyrrolo[2,3-d]pyrimidin-4-one,
- 3-[4-(7-Methyl-4-oxo-4,7-dihydro-3H-pyrrolo[2,3-d]pyrimidin-2-yl)-piperazin-1-yl]-benzonitrile, and,
- 4-[4-(7-Methyl-4-oxo-4,7-dihydro-3H-pyrrolo[2,3-d]pyrimidin-2-yl)-piperazin-1-yl]-benzonitrile.

5. The compound of claim 1 selected from the group consisting of:
- 7-Methyl-2-[4-(2-trifluoromethyl-phenyl)-piperazin-1-yl]-3,7-dihydro-pyrrolo[2,3-d]pyrimidin-4-one,
- 2-[4-(2-Fluoro-4-methanesulfonyl-phenyl)-piperazin-1-yl]-7-methyl-3,7-dihydro-pyrrolo[2,3-d]pyrimidin-4-one,
- 7-Methyl-2-[4-(4-trifluoromethyl-pyridin-2-yl)-piperazin-1-yl]-3,7-dihydro-pyrrolo[2,3-d]pyrimidin-4-one,
- 2-[4-(3,4-Dichloro-phenyl)-piperazin-1-yl]-7-methyl-3,7-dihydro-pyrrolo[2,3-d]pyrimidin-4-one,
- 7-But-3-enyl-2-[4-(2-chloro-phenyl)-piperazin-1-yl]-3,7-dihydro-pyrrolo[2,3-d]pyrimidin-4-one,
- 2-[4-(2-Fluoro-phenyl)-piperazin-1-yl]-7-methyl-3,7-dihydro-pyrrolo[2,3-d]pyrimidin-4-one,
- 7-Methyl-2-(4-phenyl-piperazin-1-yl)-3,7-dihydro-pyrrolo[2,3-d]pyrimidin-4-one,
- 2-[4-(2-Chloro-phenyl)-piperazin-1-yl]-7-methyl-3,7-dihydro-pyrrolo[2,3-d]pyrimidin-4-one,
- 7-Methyl-2-(2,3,5,6-tetrahydro-[1,2']bipyrazinyl-4-yl)-3,7-dihydro-pyrrolo[2,3-d]pyrimidin-4-one,
- 6-[4-(7-Methyl-4-oxo-4,7-dihydro-3H-pyrrolo[2,3-d]pyrimidin-2-yl)-piperazin-1-yl]-nicotinonitrile,
- 2-[(1S,4S)-5-(3-Fluoro-phenyl)-2,5-diaza-bicyclo[2.2.1]hept-2-yl]-7-methyl-3,7-dihydro-pyrrolo[2,3-d]pyrimidin-4-one and
- 2-[4-(3,5-Dichloro-pyridin-4-yl)-piperazin-1-yl]-7-methyl-3,7-dihydro-pyrrolo[2,3-d]pyrimidin-4-one.

6. The compound of claim 1 selected from the group consisting of:
- 2-(4-Trifluoromethyl-phenyl)-3,7-dihydro-pyrrolo[2,3-d]pyrimidin-4-one,
- 7-Methyl-2-(4-trifluoromethyl-phenyl)-3,7-dihydro-pyrrolo[2,3-d]pyrimidin-4-one,
- 2-(4-Methoxy-phenyl)-7-methyl-3,7-dihydro-pyrrolo[2,3-d]pyrimidin-4-one,
- 2-(6-Ethoxy-pyridin-3-yl)-7-methyl-3,7-dihydro-pyrrolo[2,3-d]pyrimidin-4-one,
- 7-Methyl-2-pyridin-3-yl-3,7-dihydro-pyrrolo[2,3-d]pyrimidin-4-one,
- 7-Methyl-2-(6-methyl-pyridin-3-yl)-3,7-dihydro-pyrrolo[2,3-d]pyrimidin-4-one,
- 4-(7-Methyl-4-oxo-4,7-dihydro-3H-pyrrolo[2,3-d]pyrimidin-2-yl)-benzonitrile,
- 7-Methyl-2-(6-trifluoromethyl-pyridin-3-yl)-3,7-dihydro-pyrrolo[2,3-d]pyrimidin-4-one.

7. The compound of claim 1 selected from the group consisting of
- 2-[4-(4-Fluoro-phenyl)-piperidin-1-yl]-7-methyl-3,7-dihydro-pyrrolo[2,3-d]pyrimidin-4-one,
- 7-But-3-enyl-2-(4-trifluoromethyl-phenyl)-3,7-dihydro-pyrrolo[2,3-d]pyrimidin-4-one,
- 7-Ethyl-2-(4-trifluoromethyl-phenyl)-3,7-dihydro-pyrrolo[2,3-d]pyrimidin-4-one,
- 7-Propyl-2-(4-trifluoromethyl-phenyl)-3,7-dihydro-pyrrolo[2,3-d]pyrimidin-4-one,
- 7-Allyl-2-(4-trifluoromethyl-phenyl)-3,7-dihydro-pyrrolo[2,3-d]pyrimidin-4-one,
- 7-(3,4-Dihydroxy-butyl)-2-(4-trifluoromethyl-phenyl)-3,7-dihydro-pyrrolo[2,3-d]pyrimidin-4-one,
- 7-(2,3-Dihydroxy-propyl)-2-(4-trifluoromethyl-phenyl)-3,7-dihydro-pyrrolo[2,3-d]pyrimidin-4-one,
- N-Ethyl-4-[4-(7-methyl-4-oxo-4,7-dihydro-3H-pyrrolo[2,3-d]pyrimidin-2-yl)-piperazin-1-yl]-benzamide,
- 7-Methyl-2-pyrazol-1-yl-3,7-dihydro-pyrrolo[2,3-d]pyrimidin-4-one,
- 7-Hydroxymethyl-2-(4-trifluoromethyl-phenyl)-3,7-dihydro-pyrrolo[2,3-d]pyrimidin-4-one,
- 7-Methyl-2-(3-methyl-3-phenyl-azetidin-1-yl)-3,7-dihydro-pyrrolo[2,3-d]pyrimidin-4-one,
- 7-Cyclopropyl-2-(4-trifluoromethyl-phenyl)-3,7-dihydro-pyrrolo[2,3-d]pyrimidin-4-one,
- 2-[4-(2-Fluoro-phenyl)-piperazin-1-yl]-7-hydroxymethyl-3,7-dihydro-pyrrolo[2,3-d]pyrimidin-4-one, 2-[4-(2,6-Difluoro-phenyl)-piperazin-1-yl]-7-(2,3-dihydroxy-propyl)-3,7-dihydro-pyrrolo[2,3-d]pyrimidin-4-one, and, 7-Methyl-2-phenyl-3,7-dihydro-pyrrolo[2,3-d]pyrimidin-4-one.

8. The compound of claim 1 which compound is 2-[4-[2 6-difluoro-4-(2-methoxyethoxy)phenyl]piperazin-1-yl]-7-(2-hydroxyethyl)-3H-pyrrolo[2,3-d]pyrimidin-4-one.

9. A method of inhibiting tankyrase 1 and/or tankyrase 2 by contacting either or both with a compound of any one of claims 1 to 8.

10. A method for treating colorectal cancer by administering to a patient in need thereof a therapeutically active amount of a compound according to any one of claims 1 to 8.

11. A composition containing a compound according to any one of claims 1 to 8 and at least one pharmaceutically acceptable carrier, diluent or excipient.

* * * * *